(12) United States Patent
Ralston et al.

(10) Patent No.: US 7,964,643 B2
(45) Date of Patent: Jun. 21, 2011

(54) ARYL ALKYL SULFONAMIDES AS THERAPEUTIC AGENTS FOR THE TREATMENT OF BONE CONDITIONS

(75) Inventors: Stuart Hamilton Ralston, Aberdeen (GB); Iain Robert Greig, Aberdeen (GB); Aymen Ibrahim Idris Mohamed, Aberdeen (GB); Robert Jurgen Van 'T Hof, Aberdeen (GB)

(73) Assignee: The University Court of the University of Aberdeen, Aberdeen (GB)

( * ) Notice: Subject to any disclaimer, the term of this patent is extended or adjusted under 35 U.S.C. 154(b) by 1012 days.

(21) Appl. No.: 11/628,084

(22) PCT Filed: May 23, 2005

(86) PCT No.: PCT/GB2005/002043
§ 371 (c)(1),
(2), (4) Date: Jun. 8, 2007

(87) PCT Pub. No.: WO2005/118528
PCT Pub. Date: Dec. 15, 2005

(65) Prior Publication Data
US 2008/0119555 A1      May 22, 2008

(30) Foreign Application Priority Data
Jun. 4, 2004 (GB) .................................. 0412553.0

(51) Int. Cl.
*A61K 31/18* (2006.01)
*C07C 311/00* (2006.01)
(52) U.S. Cl. ............. 514/603; 514/604; 564/84; 564/87
(58) Field of Classification Search .......................... None
See application file for complete search history.

(56) References Cited

U.S. PATENT DOCUMENTS

| | | | |
|---|---|---|---|
| 5,760,028 | A | 6/1998 | Jadhav et al. |
| 6,159,995 | A | 12/2000 | Thorwart et al. |
| 6,451,824 | B1 | 9/2002 | Thorwart et al. |
| 2003/0144292 | A1 | 7/2003 | Natchus et al. |
| 2005/0119305 | A1* | 6/2005 | Naka et al. ..................... 514/317 |

FOREIGN PATENT DOCUMENTS

| | | |
|---|---|---|
| DE | 10 46 220 | 12/1958 |
| EP | 0 877 018 | 11/1998 |
| EP | 0 877 019 | 11/1998 |
| EP | 0 960 882 | 12/1999 |
| EP | 1 491 190 | 1/2004 |
| EP | 1 431 267 | 6/2004 |
| JP | 11-246527 | 9/1999 |
| WO | 96/37492 | 11/1996 |
| WO | 97/16433 | 5/1997 |
| WO | 97/33887 | 9/1997 |
| WO | 98/03166 | 1/1998 |
| WO | 98/23608 | 6/1998 |
| WO | 98/43962 | 10/1998 |
| WO | 98/50342 | 11/1998 |
| WO | 99/37621 | 7/1999 |
| WO | 99/42443 | 8/1999 |
| WO | 01/16137 | 3/2001 |
| WO | 01/90077 | 11/2001 |
| WO | 02/060867 | 8/2002 |
| WO | 02/074298 | 9/2002 |
| WO | 03/037321 | 5/2003 |
| WO | 2004/022561 | 3/2004 |
| WO | 2004/098582 | 11/2004 |

OTHER PUBLICATIONS

Armour K.J., et al., 2001, "Inhibition of bone resorption in vitro and prevention of ovariectomy-induced bone loss in vivo by flurbiprofen nitroxybutylester (HCT1026)," *Arthritis and Rheumatism*, vol. 44, No. 9, pp. 2185-2192.
Augstein, J., et al., 1965, "Some cardiovascular effects of a series of aryloxyalkylamines 1", *J. Med. Chem.*, vol. 8, pp. 356-367.
Coxon, F.P., et al., 2000, "Protein geranylgeranylation is required for osteoclast formation, function, and survival: inhibition by bisphosphonates and GGTI-298," *J.Bone Miner.Res.*, vol. 15, pp. 1467-1476.
Degenhardt, C.R., et al., 1986, "Synthesis of Ethenylidenebis(phosphonic acid) and its Tetraalkyl Esters," *J. Org. Chem.*, vol. 51, pp. 3488-3490.
Eberhard, A., et al., 1965, "Hydrolysis of Phostonates," *J. Amer. Chem. Soc.*, vol. 87, pp. 253-260.
Ha-Duong, N-T, et al, 2001, "Synthesis of sulfaphenazole derivatives and their use as inhibitors and tools for comparing the active sites of human liver cytochromes P450 of the 2C subfamily", *J. Med. Chem.*, vol. 44, pp. 3622-3631. Herczegh, P., et al, 2002, "Osteoadsorptive Bisphosphonate Derivatives of Fluoroquinolone Antibacterials," *J. Med. Chem.*, vol. 45, pp. 2338-2341.
Hughes, D.E., et al., 1997, "Apoptosis in bone physiology and disease," *Molecular Pathology*, vol. 50, pp. 132-137.
Kong, Y.Y., et al., 1999, "OPGL is a key regulator of osteoclastogenesis, lymphocyte development and lymph-node organogenesis," *Nature*, vol. 397, pp. 315-323.
Luckman, et al., 1998, "Heterocycle-containing bisphosphonates cause apoptosis and inhibit bone resorption by preventing protein prenylation: evidence from structure-activity relationships in J774 macrophages," *J. Bone Miner.Res.*, vol. 13, pp. 1668-1678.

(Continued)

*Primary Examiner* — Paul A Zucker
(74) *Attorney, Agent, or Firm* — Nixon & Vanderhye P.C.

(57) ABSTRACT

The present invention pertains to compounds of the following formula (wherein $R^P$, r, q, $R^N$, $R^{alk}$, and Q are as defined herein) and compositions comprising those compounds. The compounds may be used to inhibit osteoclast survival, formation, and/or activity; to inhibit conditions mediated by osteoclasts and/or characterised by bone resorption; in the treatment of bone disorders such as osteoporosis, rheumatoid arthritis, cancer associated bone disease, Paget's disease; and/or in the treatment of conditions associated with inflammation or activation of the immune system.

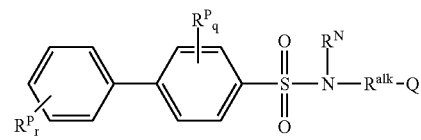

32 Claims, 1 Drawing Sheet

OTHER PUBLICATIONS

MacPherson, H; et al., 1999, "Expression and functional role of nitric oxide synthase isoforms in human osteoblast-like cells," *Bone*, vol. 24, pp. 179-185.

Mundy, G.R., 1996, "Chapter 1: Bone Remodeling", in *Bone Remodeling and its disorders* (2nd edition), London, (Ed. Martin Dunitz), pp. 1-11.

Nociari, M.N., et al., 1998, "A novel one-step, highly sensitive fluorimetric assay to evaluate cell-mediated cytotoxicity," *Journal of Immunological Methods*, vol. 213, pp. 157-167.

Nyormoi, O., et al., 2003, "An MMP-2/MMP-9 inhibitor, 5a, enhances apoptosis induced by ligands of the TNF receptor superfamily in cancer cells", *Cell Death and Differentiation*, vol. 10, pp. 558-569.

Peyman, A., et al., 2001, "$\alpha_v\beta_3$ antagonists based on a central thiophene scaffold", *Bio. & Med. Chem. Letters*, Vo. 11, pp. 2011-2015.

Raisz, L.G., 1988, "Local and systemic factors in the pathogenesis of osteoporosis," *N. Engl. J. Med.*, vol. 318, pp. 818-828.

Ralston, S.H., 1997, "Science, Medicine and the Future: Osteoporosis," *Br. Med. J.*, vol. 315, pp. 469-472.

Rodan, G.A., et al., 1997, "The missing bone," *Cell*, vol. 89, pp. 677-680.

Takahashi, N.; et al., 1988, "Osteoblastic cells are involved in osteoclast formation," *Endocrinology*, vol. 123, pp. 2600-2602.

Takasuka, M., et al., 1991, "FTIR spectral study of intramolecular hydrogen bonding in thromboxane $A_2$ receptor antagonist S-145 and related compounds. 3. Conformation and activity of S-145 analogues", *J. Med. Chem.*, vol. 34, pp. 1885-1891.

van't Hof, R.J., et a;., 1997, "Cytokine-induced nitric oxide inhibits bone resorption by inducing apoptosis of osteoclast progenitors and suppressing osteoclast activity," *J. Bone & Miner. Res.*, vol. 12, pp. 1797-1804.

Yasuda, H., et al, 1998, "Identity of osteoclastogenesis inhibitory factor (OCIF) and osteoprotegerin (OPG): a mechanism by which OPG/OCIF inhibits osteoclastogenesis in vitro", *Endocrinology*, vol. 139, pp. 1329-1337.

\* cited by examiner

US 7,964,643 B2

ARYL ALKYL SULFONAMIDES AS THERAPEUTIC AGENTS FOR THE TREATMENT OF BONE CONDITIONS

RELATED APPLICATION

This application is the US national phase of international application PCT/GB2005/002043 filed 23 May 2005, which designated the U.S. and claims benefit of GB 0412553.0, filed 4 Jun. 2004, the entire contents of each of which are hereby incorporated by reference.

TECHNICAL FIELD

The present invention pertains generally to the field of therapeutic compounds for treating bone conditions etc., and more specifically to certain aryl alkyl sulfonamides and derivatives thereof which, inter alia, inhibit osteoclast survival, formation, and/or activity; and/or inhibit bone resorption. The present invention also pertains to pharmaceutical compositions comprising such compounds, and the use of such compounds and compositions, both in vitro and in vivo, to inhibit osteoclast survival, formation, and/or activity, and to inhibit conditions mediated by osteoclasts and/or characterised by bone resorption, in the treatment of bone disorders such as osteoporosis, rheumatoid arthritis, cancer associated bone disease, Paget's disease, and the like; and/or in the treatment of conditions associated with inflammation or activation of the immune system.

BACKGROUND

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiments.

Functions of Bone

The function of bone is to provide mechanical support for joints, tendons and ligaments, to protect vital organs from damage and to act as a reservoir for calcium and phosphate in the preservation of normal mineral homeostasis. Diseases of bone compromise these functions, leading to clinical problems such as bone pain, bone deformity, fracture and abnormalities of calcium and phosphate homeostasis.

Types of Bone

The normal skeleton contains two types of bone: cortical or compact bone, which makes up most of shafts (diaphysis) of the long bones such as the femur and tibia, and trabecular or spongy bone which makes up most of the vertebral bodies and the ends of the long bones.

Trabecular bone has a greater surface area than cortical bone and because of this is remodeled more rapidly. This means that conditions associated with increased bone turnover tend to affect trabecular bone more quickly and more profoundly than cortical bone. Cortical bone is arranged in so-called Haversian systems which consist of a series of concentric lamellae of collagen fibres surrounding a central canal that contains blood vessels. Nutrients reach the central parts of the bone by an interconnecting system of canaliculi that run between osteocytes buried deep within bone matrix and lining cells on the bone surface. Trabecular bone has a similar structure, but here the lamellae run in parallel to the bone surface, rather than concentrically as in cortical bone.

Bone Composition

The organic component of bone matrix comprises mainly of type I collagen; a fibrillar protein formed from three protein chains, wound together in a triple helix. Collagen type I is laid down by bone forming cells (osteoblasts) in organised parallel sheets (lamellae) and subsequently the collagen chains become cross-linked by specialised covalent bonds which help to give bone its tensile strength. When bone is formed rapidly (for example in Paget's disease, or in bone metastases), the lamellae are laid down in a disorderly fashion giving rise to "woven bone", which is mechanically weak and easily fractured. Bone matrix also contains small amounts of other collagens and several non-collagenous proteins and glycoproteins. Some of these, such as osteocalcin, are specific to bone, whereas others, such as osteopontin and fibronectin and various peptide growth factors are also found in other connective tissues. The function of non-collagenous bone proteins is unclear, but it is thought that they are involved in mediating the attachment of bone cells to bone matrix, and in regulating bone cell activity during the process of bone remodelling. The organic component of bone forms a framework upon which mineralisation occurs. During bone formation, osteoblasts lay down uncalcified bone matrix (osteoid) which contains the components described above and small amounts of other proteins, which are adsorbed from extracellular fluid. After a lag phase of about 10 days, the matrix becomes mineralised, as hydroxyapatite ($Ca_{10}(PO_4)_6(OH)_2$) crystals are deposited in the spaces between collagen fibrils. Mineralisation confers upon bone the property of mechanical rigidity, which complements the tensile strength, and elasticity derived from bone collagen.

Bone Cell Function and Bone Remodelling

The mechanical integrity of the skeleton is maintained by the process of bone remodelling, which occurs throughout life, in order that damaged bone can be replaced by new bone. Remodelling can be divided into four phases; resorption; reversal, formation and quiescence (see, e.g., Raisz, 1988; Mundy, 1996). At any one time approximately 10% of bone surface in the adult skeleton is undergoing active remodelling whereas the remaining 90% is quiescent.

Osteoclast Formation and Differentiation

Remodelling commences with attraction of bone resorbing cells (osteoclasts) to the site, which is to be resorbed. These are multinucleated phagocytic cells, rich in the enzyme tartrate-resistant acid phosphatase, which are formed by fusion of precursors derived from the cells of monocyte/macrophage lineage. Recent work has identified several molecules that are of key importance in the regulation of osteoclast differentiation (see, e.g., Ralston, 1997). The transcription factor PU-1 which is expressed in early osteoclast precursors is necessary for the initial stages of osteoclast and monocyte differentiation, whereas other transcription factors including c-fos and NFkB play an essential role in stimulating differentiation of committed precursors to mature osteoclasts. Osteoclast formation and activation is also dependent on close contact between osteoclast precursors and bone marrow stromal cells. Stromal cells secrete the cytokine M-CSF (macrophage colony stimulating factor), which is essential for differentiation of both osteoclasts and macrophages from a common precursor. Stromal cells also express a molecule called RANK ligand (RANKL) on the cell surface, which interacts with another cell surface receptor present on osteoclast precursors called RANK (Receptor Activator of Nuclear Factor Kappa B) to promote differentiation of osteoclast precursors to mature osteoclasts. The RANK-RANKL interaction is blocked by another molecule called Osteoprotegerin (OPG), which is a "decoy" ligand for RANK and which acts a potent inhibitor of osteoclast formation (see, e.g., Kong et al., 1999; Yasuda et al., 1998). Recent work suggests that many of the factors that promote osteoclast formation and bone resorption do so by regulating expression of these molecules.

Mature osteoclasts form a tight seal over the bone surface and resorb bone by secreting hydrochloric acid and proteolytic enzymes through the "ruffled border" into a space beneath the osteoclast (Howship's lacuna). Formation of this ruffled border is critically dependent on the presence of c-src, a cell membrane associated signalling protein. The hydrochloric acid secreted by osteoclasts dissolves hydroxyapatite and allows proteolytic enzymes (mainly Cathepsin K and matrix metalloproteinases) to degrade collagen and other matrix proteins. Molecules which have been identified as being important in regulating osteoclast activity include; carbonic anhydrase II (Ca-II) which catalyses formation of hydrogen ions within osteoclasts; TCIRG1, which encodes a subunit of the osteoclast proton pump, and Cathepsin K which degrades collagen and other non-collagenous proteins. Deficiency of these proteins causes osteopetrosis, which is a disease associated with increased bone density and osteoclast dysfunction. After resorption is completed osteoclasts undergo programmed cell death (apoptosis), in the so-called reversal phase, which heralds the start of bone formation. It has recently been discovered that many of the drugs, which are used clinically to inhibit bone resorption, such as bisphosphonates and oestrogen do so by promoting osteoclast apoptosis (see, e.g., Hughes et al., 1997).

Osteoblast Formation and Differentiation

Bone formation begins with attraction of osteoblast precursors, which are derived from mesenchymal stem cells in the bone marrow, to the bone surface. Although these cells have the potential to differentiate into many cell types including adipocytes, myocytes, and chondrocytes it is now known that the key trigger for osteoblast differentiation is expression of a regulatory molecule called Cbfa1 in pre-osteoblasts (see, e.g., Rodan et al., 1997). Cbfa1 is a transcription factor that activates co-ordinated expression of genes characteristic of the osteoblast phenotype such as osteocalcin, type I collagen and alkaline phosphatase. In contrast, expression of the transcription factor PPARg promotes the cells towards adipocyte differentiation. It is currently thought that some cases of osteoporosis may occur because there is an imbalance between the rate of osteoblast and adipocyte differentiation in bone. Mature osteoblasts are plump cuboidal cells, which are responsible for the production of bone matrix. They are rich in the enzyme alkaline phosphatase and the protein osteocalcin, which are used clinically as serum markers of osteoblast activity. Osteoblasts lay down bone matrix which is initially unmineralised (osteoid), but which subsequently becomes calcified after about 10 days to form mature bone. During bone formation, some osteoblasts become trapped within the matrix and differentiate into osteocytes, whereas others differentiate into flattened "lining cells" which cover the bone surface. Osteocytes connect with one another and with lining cells on the bone surface by an intricate network of cytoplasmic processes, running through cannaliculi in bone matrix. Osteocytes appear to act as sensors of mechanical strain in the skeleton, and release signalling molecules such as prostaglandins and nitric oxide (NO), which modulate the function of neighbouring bone cells.

Regulation of Bone Remodelling

Bone remodelling is a highly organised process, but the mechanisms which determine where and when remodelling occurs are poorly understood. Mechanical stimuli and areas of micro-damage are likely to be important in determining the sites at which remodelling occurs in the normal skeleton. Increased bone remodelling may result from local or systemic release of inflammatory cytokines like interleukin-1 and tumour necrosis factor in inflammatory diseases. Calciotropic hormones such as parathyroid hormone (PTH) and 1,25-dihydroxyvitamin D, act together to increase bone remodelling on a systemic basis allowing skeletal calcium to be mobilised for maintenance of plasma calcium homeostasis. Bone remodelling is also increased by other hormones such as thyroid hormone and growth hormone, but suppressed by oestrogen, androgens and calcitonin.

Common Bone Diseases

Osteoporosis is a common disease characterized by reduced bone density, deterioration of bone tissue and increase risk of fracture. Many factors contribute to the pathogenesis of osteoporosis including poor diet, lack of exercise, smoking and excessive alcohol intake. Osteoporosis may also arise in association with inflammatory diseases such as rheumatoid arthritis, endocrine diseases such as thyrotoxicosis and with certain drug treatments such as glucocorticoids. However one of the most important factors in the pathogenesis of osteoporosis is heredity.

Paget's disease of bone is a common condition of unknown cause, characterized by increased bone turnover and disorganized bone remodelling, with areas of increased osteoclastic and osteoblast activity. Although Pagetic bone is often denser than normal, the abnormal architecture causes the bone to be mechanically weak, resulting in bone deformity and increased susceptibility to pathological fracture.

Multiple Myeloma is a cancer of plasma cells. In contrast to most other haematological malignancies, the tumour cells do not circulate in the blood, but accumulate in the bone marrow where they give rise to high levels of cytokines that activate osteoclastic bone resorption (e.g., interleukin-6). The disease accounts for approximately 20% of all haematological cancers and is mainly a disease of elderly people.

Bone Resorption Inhibitors

Several common diseases, such as osteoporosis and rheumatoid arthritis, are characterised by bone loss due to excess bone resorption by osteoclasts. At present the most commonly used types of drugs used to suppress osteoclast activity in these diseases are bisphosphonates (BPs) and non-steroidal anti-inflammatory drugs (NSAIDs).

Bisphosphonates (also know as diphosphonates) are an important class of drugs used in the treatment of bone diseases involving excessive bone destruction or resorption, e.g., Paget's disease, tumour-associated osteolysis, and post-menopausal osteoporosis. Bisphosphonates are structural analogues of naturally occurring pyrophosphate. Whereas pyrophosphate consists of two phosphate groups linked by an oxygen atom (P—O—P), bisphosphonates have two phosphate groups linked by a carbon atom (P—C—P). This makes bisphosphonates very stable and resistant to degradation. Furthermore, like pyrophosphate, bisphosphonates have very high affinity for calcium and therefore target to bone mineral in vivo. The carbon atom that links the two phosphate groups has two side chains attached to it, which can be altered in structure. This gives rise to a multitude of bisphosphonate compounds with different anti-resorptive potencies. Bone resorption is mediated by highly specialised, multinucleated osteoclast cells. Bisphosphonate drugs specifically inhibit the activity and survival of these cells. Firstly, after intravenous or oral administration, the bisphosphonates are rapidly cleared from the circulation and bind to bone mineral. As the mineral is then resorbed and dissolved by osteoclasts, it is thought that the drug is released from the bone mineral and is internalised by osteoclasts. Intracellular accumulation of the drugs inhibits the ability of the cells to resorb bone (probably by interfering with signal transduction pathways or cellular metabolism) and causes osteoclast apoptosis.

NSAIDs are widely used in the treatment of inflammatory diseases, but often cause severe gastro-intestinal (GI) side effects. NSAIDs developed by Nicox SA (Sophia Antipolis, France), that contain a nitric oxide (NO)-donor group (NO-NSAID) exhibit anti-inflammatory properties without causing GI side effects. An example of such a compound is HCT 1026, which is a nitrosylated derivative of the NSAID flurbiprofen (see, for example, Armour et al., 2001).

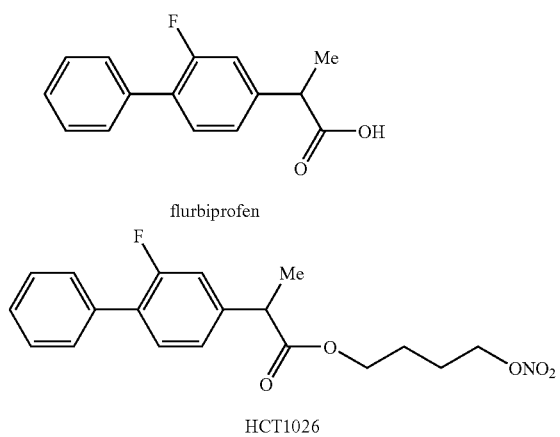

Augstein et al., 1965, describe the following compound, which apparently has cardiovascular activity.

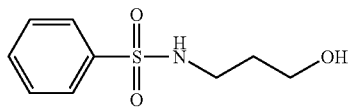

Takasuka et al., 1991, describe the following compound (S-145), which apparently is an antagonist for the thromboxane $A_2$ receptor.

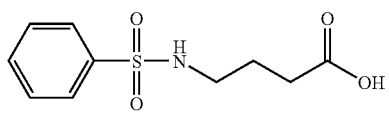

Ralston et al., 2003 and Ralston et al., 2004 describe biphenyl compounds for use in the treatment of bone conditions.

There is a recognized need for more and better treatments for bone-related diseases which offer, for example, one or more the following benefits:

(a) improved activity;
(b) improved efficacy;
(c) improved specificity;
(d) reduced toxicity (e.g., cytotoxicity);
(e) complement the activity of other treatments (e.g., chemotherapeutic agents);
(f) reduced intensity of undesired side-effects;
(g) fewer undesired side-effects;
(h) simpler methods of administration (e.g., route, timing, compliance);
(i) reduction in required dosage amounts;
(j) reduction in required frequency of administration;
(k) increased ease of synthesis, purification, handling, storage, etc.;
(l) reduced cost of synthesis, purification, handling, storage, etc.

Thus, one aim of the present invention is the provision of active compounds which offer one or more of the above benefits.

SUMMARY OF THE INVENTION

One aspect of the invention pertains to active compounds, specifically, certain aryl alkyl sulfonamides and derivatives thereof, as described herein.

Another aspect of the invention pertains to a composition comprising an active compound as described herein and a pharmaceutically acceptable carrier or diluent.

Another aspect of the invention pertains to a method of inhibiting osteoclast survival, formation, and/or activity, in vitro or in vivo, comprising contacting an osteoclast with an effective amount of an active compound, as described herein.

Another aspect of the invention pertains to a method of inhibiting bone resorption, in vitro or in vivo, comprising contacting cells in the bone microenvironment with a therapeutically-effective amount of an active compound, as described herein.

Another aspect of the present invention pertains to a method for the treatment comprising administering to a subject in need of treatment a therapeutically-effective amount of an active compound, as described herein, preferably in the form of a pharmaceutical composition.

Another aspect of the present invention pertains to an active compound as described herein for use in a method of treatment of the human or animal body by therapy.

Another aspect of the present invention pertains to use of an active compound, as described herein, in the manufacture of a medicament for use in treatment.

In one embodiment, the treatment is treatment of a bone disorder, for example, a condition mediated by osteoclasts and/or characterised by bone resorption, as described herein. In one embodiment, the treatment is treatment of a condition mediated by osteoclasts, as described herein. In one embodiment, the treatment is treatment of a condition characterised by bone resorption, as described herein.

In one embodiment, the treatment is treatment of osteoporosis, rheumatoid arthritis, cancer associated bone disease, or Paget's disease.

In one embodiment, the treatment is treatment of a condition associated with inflammation or activation of the immune system, as described herein.

Another aspect of the present invention pertains to a kit comprising (a) an active compound, as described herein, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Figure 1:
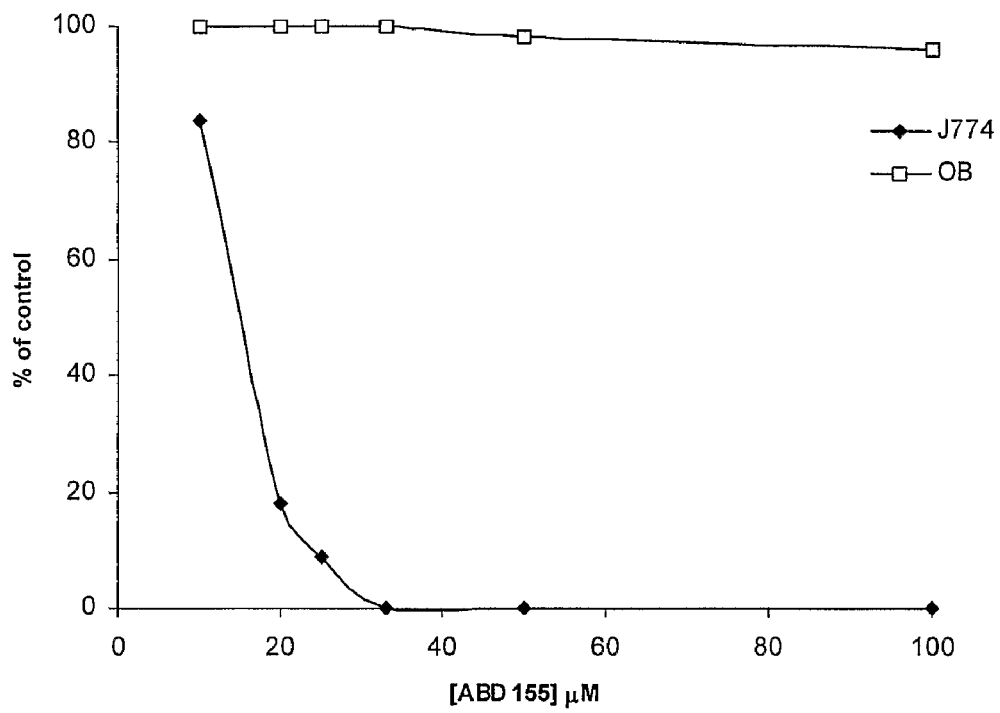
FIG. 1 is a graph of J774 macrophage viability ("J774") (solid diamonds, ♦) as measured by the Alamar Blue macrophage J774 viability assay; and osteoblast survival ("OB") (open squares, □) as measured by the Alamar Blue mouse osteoblast assay; expressed as percent (%) of control, after 72 hours exposure to biphenyl-4-sulfonic acid-(4-hydroxybutyl)-amide (ABD-155) as a function of compound concentration.

One aspect of the present invention pertains to compounds which may be described as "aryl alkyl sulfonamides and derivatives thereof", and their surprising and unexpected osteoclast-inhibitory and resorption-inhibitory effects.

One aspect of the present invention pertains to compounds of the following formula, and pharmaceutically acceptable salts, solvates, amides, esters, ethers, chemically protected forms, or prodrugs thereof:

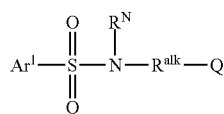
(1)

The Group $Ar^1$

The group $Ar^1$ is independently a $C_{5-20}$aryl group, and is optionally substituted (e.g., with one or more groups, e.g., as defined for $R^P$).

In one embodiment, $Ar^1$ is independently phenyl, naphthyl, phenanthryl, fluorenyl, anthracenyl; furanyl, thienyl, pyrrolyl, imidazolyl, pyrazolyl, oxazolyl, thiazolyl; pyridyl, pyrazinyl, pyrimidinyl, pyridazinyl; indolyl; benzimidazolyl, benzothiofuranyl; quinolinyl; acridinyl, or carbazolyl; and is optionally substituted.

In one embodiment, $Ar^1$ is independently a $C_{5-6}$aryl group, and is optionally substituted.

In one embodiment, $Ar^1$ is independently phenyl, furanyl, thienyl, pyrrolyl, imidazolyl, pyrazolyl, oxazolyl, thiazolyl; pyridyl, pyrazinyl, pyrimidinyl, or pyridazinyl; and is optionally substituted.

In one embodiment, $Ar^1$ is independently a $C_{5-20}$carboaryl group, and is optionally substituted.

In one embodiment, $Ar^1$ is as described herein, but with the proviso that it is not unsubstituted phenyl.

The Group $Ar^1$: Optionally Substituted Phenyl

In one embodiment, $Ar^1$ is independently phenyl, and is optionally substituted.

In one embodiment, $Ar^1$ is independently substituted phenyl.

In one embodiment, $Ar^1$ is independently an optionally substituted phenyl group of the following formula:

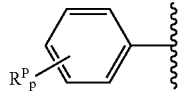

wherein each $R^P$ is independently a phenyl substituent; and p is independently an integer from 0 to 5.

In one embodiment, p is independently an integer from 0 to 4; 0 to 3; 0 to 2; 0 or 1; 0.

In one embodiment, p is independently an integer from 1 to 4; 1 to 3; 1 or 2; 1.

The Group $Ar^1$: Optionally Substituted Biphenyl, Phenanthryl, Fluorenyl, Carbazolyl In one embodiment, $Ar^1$ is independently biphenyl, phenanthyl, fluorenyl, or carbazolyl (e.g., derived from biphenyl, phenanthrene, fluorene, or carbazole, respectively), and is optionally substituted.

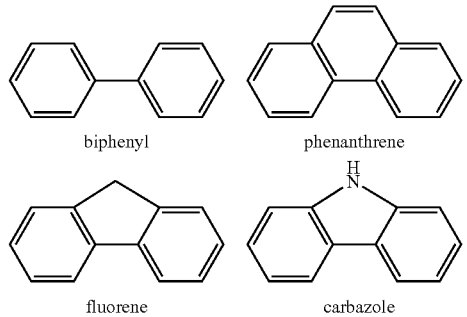

biphenyl    phenanthrene fluorene    carbazole

The Group $Ar^1$: Optionally Substituted Biphenyl

In one embodiment, $Ar^1$ is independently biphenyl, and is optionally substituted.

In one embodiment, $Ar^1$ is independently an optionally substituted biphenyl group of the following formula:

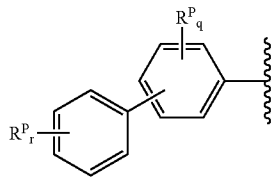

wherein:
each $R^P$ is independently a phenyl substituent;
q is independently an integer from 0 to 4; and
r is independently an integer from 0 to 5.

In one embodiment, q is independently an integer from 0 to 4; 0 to 3; 0 to 2; 0 or 1; 0.

In one embodiment, q is independently an integer from 1 to 4; 1 to 3; 1 or 2; 1.

In one embodiment, r is independently an integer from 0 to 5; 0 to 4; 0 to 3; 0 to 2; 0 or 1; 0.

In one embodiment, r is independently an integer from 1 to 5; 1 to 4; 1 to 3; 1 or 2; 1.

In one embodiment, q is 0, and $Ar^1$ is an optionally substituted biphenyl group of the following formula (e.g., biphenyl-2-yl, biphenyl-3-yl, biphenyl-4-yl):

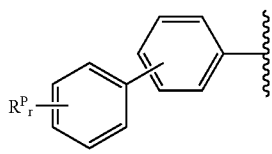

The Group $Ar^1$: Optionally Substituted Biphenyl-4-yl

In one embodiment, $Ar^1$ is independently an optionally substituted biphenyl-4-yl group of the following formula:

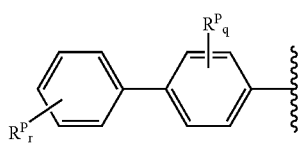

In one embodiment, $Ar^1$ is independently is an optionally substituted biphenyl-4-yl group of the following formula:

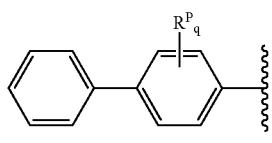

In one embodiment, $Ar^1$ is independently an optionally substituted biphenyl-4-yl group of the following formula:

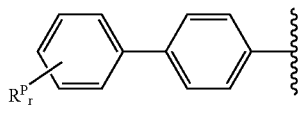

The Group $Ar^1$: 4'-Substituted Biphenyl-4-yl

In one embodiment, $Ar^1$ is independently a 4'-substituted biphenyl-4-yl group of the following formula:

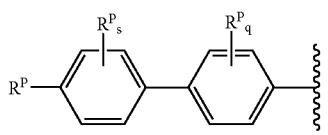

wherein s is independently an integer from 0 to 4.

In one embodiment, s is independently an integer from 0 to 4; 0 to 3; 0 to 2; 0 or 1; 0.

In one embodiment, s is independently an integer from 1 to 4; 1 to 3; 1 to 2; 1.

In one embodiment, $Ar^1$ is independently a 4'-substituted biphenyl-4-yl group of the following formula:

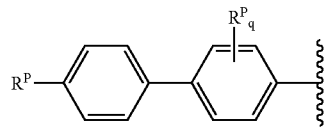

In one embodiment, $Ar^1$ is independently a 4'-substituted biphenyl-4-yl group of the following formula:

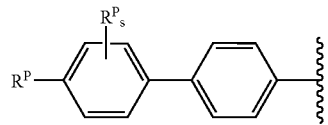

In one embodiment, $Ar^1$ is independently a 4'-substituted biphenyl-4-yl group of the following formula:

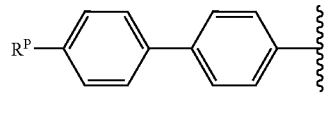

The Group $Ar^1$: 3'-Substituted Biphenyl-4-yl

In one embodiment, $Ar^1$ is independently a 3'-substituted biphenyl-4-yl group of the following formula:

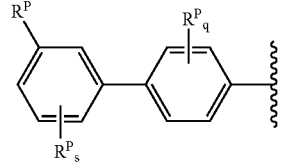

In one embodiment, $Ar^1$ is independently a 3'-substituted biphenyl-4-yl group of the following formula:

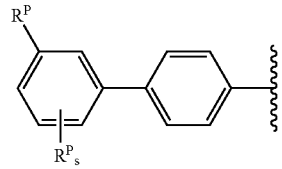

In one embodiment, $Ar^1$ is independently a 3'-substituted biphenyl-4-yl group of the following formula:

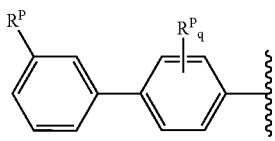

In one embodiment, $Ar^1$ is independently a 3'-substituted biphenyl-4-yl group of the following formula:

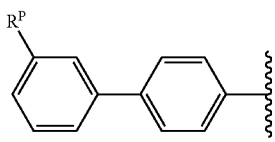

The Group $Ar^1$: 3',4'-Disubstituted Biphenyl-4-yl

In one embodiment, $Ar^1$ is independently a 3',4'-disubstituted biphenyl-4-yl group of the following formula:

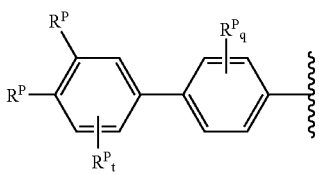

wherein t is independently an integer from 0 to 3.

In one embodiment, t is independently an integer from 0 to 3; 0 to 2; 0 or 1; 0.

In one embodiment, t is independently an integer from 1 to 3; 1 or 2; 1.

In one embodiment, $Ar^1$ is independently a 3',4'-disubstituted biphenyl-4-yl group of the following formula:

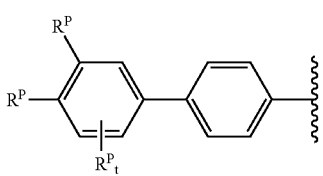

In one embodiment, $Ar^1$ is independently a 3',4'-disubstituted biphenyl-4-yl group of the following formula:

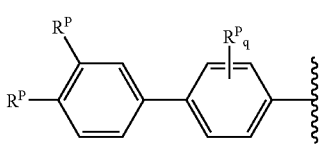

In one embodiment, $Ar^1$ is independently a 3',4'-disubstituted biphenyl-4-yl group of the following formula:

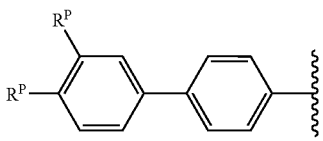

The Group $Ar^1$: 2'-Substituted Biphenyl-4-yl

In one embodiment, $Ar^1$ is independently a 2'-substituted biphenyl-4-yl group of the following formula:

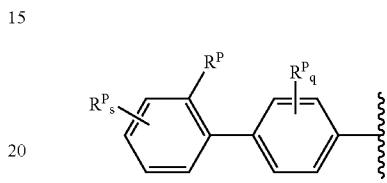

In one embodiment, $Ar^1$ is independently a 2'-substituted biphenyl-4-yl group of the following formula:

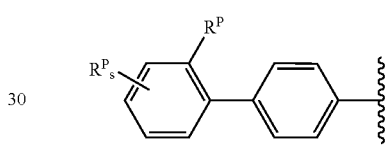

In one embodiment, $Ar^1$ is independently a 2'-substituted biphenyl-4-yl group of the following formula:

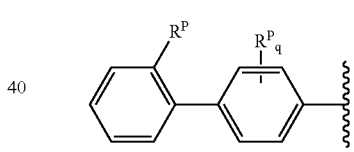

In one embodiment, $Ar^1$ is independently a 2'-substituted biphenyl-4-yl group of the following formula:

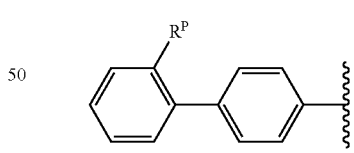

The Group $Ar^1$: 2',4'-Disubstituted Biphenyl-4-yl

In one embodiment, $Ar^1$ is independently a 2',4'-disubstituted biphenyl-4-yl group of the following formula:

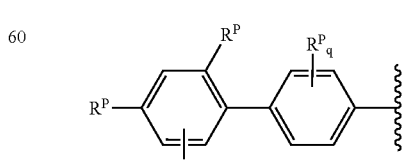

In one embodiment, Ar¹ is independently a 2',4'-disubstituted biphenyl-4-yl group of the following formula:

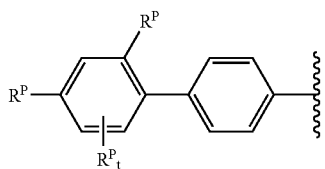

In one embodiment, Ar¹ is independently a 2',4'-disubstituted biphenyl-4-yl group of the following formula:

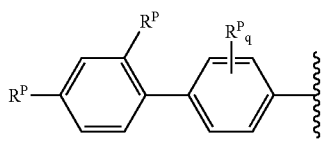

In one embodiment, Ar¹ is independently a 2',4'-disubstituted biphenyl-4-yl group of the following formula:

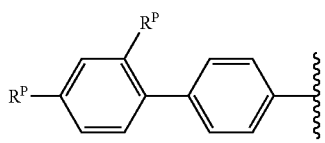

The Group Ar¹: Unsubstituted Biphenyl-4-yl
In one embodiment, Ar¹ is independently an unsubstituted biphenyl-4-yl group of the following formula:

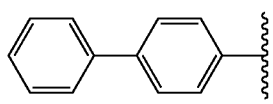

The Group Ar¹: Optionally Substituted Phenanthryl
In one embodiment, Ar¹ is independently phenanthyl (e.g., phenanthr-2-yl), and is optionally substituted.
In one embodiment, Ar¹ is independently an optionally substituted phenanthyl group of the following formula:

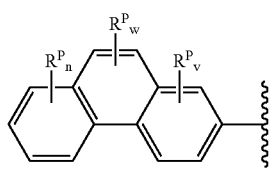

wherein:
each $R^P$ is independently a phenanthyl substituent (as defined herein for phenyl substituents);
u is independently an integer from 0 to 4;
v is independently an integer from 0 to 3; and
w is independently an integer from 0 to 2.
In one embodiment, w is independently an integer from 0 to 2; 0 or 1; 0.
In one embodiment, w is independently an integer from 1 or 2; 1.

The Group Ar¹: Optionally Substituted Fluorenyl
In one embodiment, Ar¹ is independently fluorenyl (e.g., fluoren-2-yl), and is optionally substituted.
In one embodiment, Ar¹ is independently an optionally substituted fluorenyl group of the following formula:

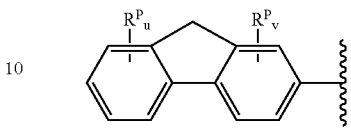

wherein:
each $R^P$ is independently a fluorenyl substituent (as defined herein for phenyl substituents);
u is independently an integer from 0 to 4; and
v is independently an integer from 0 to 3.
In one embodiment, u is independently an integer from 0 to 4; 0 to 3; 0 to 2; 0 or 1; 0.
In one embodiment, u is independently an integer from 1 to 4; 1 to 3; 1 or 2; 1.
In one embodiment, v is independently an integer from 0 to 3; 0 to 2; 0 or 1; 0.
In one embodiment, v is independently an integer from 1 to 3; 1 or 2; 1.

The Group Ar¹: Optionally Substituted Carbazolyl
In one embodiment, Ar¹ is independently carbazolyl (e.g., carbazol-2-yl), and is optionally substituted.
In one embodiment, Ar¹ is independently an optionally substituted carbazolyl group of the following formula:

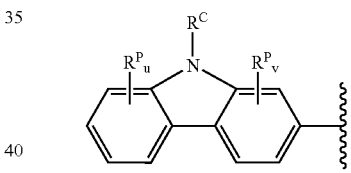

wherein:
each $R^P$ is independently a carbazolyl substituent (as defined herein for phenyl substituents);
u is independently an integer from 0 to 4;
v is independently an integer from 0 to 3; and
$R^C$ is independently —H or as defined in (4), (17), (20), (21), (22) or (23) below.
In one embodiment, u is independently an integer from 0 to 4; 0 to 3; 0 to 2; 0 or 1; 0.
In one embodiment, u is independently an integer from 1 to 4; 1 to 3; 1 or 2; 1.
In one embodiment, v is independently an integer from 0 to 3; 0 to 2; 0 or 1; 0.
In one embodiment, v is independently an integer from 1 to 3; 1 or 2; 1.

Phenyl Substituents, $R^P$
Examples of phenyl substituents, $R^P$, include, but are not limited to, those described below under the heading "substituents."
In one embodiment, each of the substituents (e.g., $R^P$) is independently selected from: (1) carboxylic acid; (2) ester; (3) amido; (4) acyl; (5) halo; (6) cyano; (7) nitro; (8) hydroxy; (9) ether; (10) thiol; (11) thioether; (12) acyloxy; (13) amino; (14) acylamino; (15) aminoacylamino; (16) sulfonamino; (17) sulfonyl; (18) sulfonate; (19) sulfonamido; (20)

$C_{5-20}$aryl-$C_{1-7}$alkyl; (21) $C_{5-20}$aryl; (22) $C_{3-20}$heterocyclyl; (23) $C_{1-7}$alkyl; (24) oxo; (25) imino; (26) hydroxyimino; (27) phosphate.

In one embodiment, each of the substituents (e.g., $R^P$) is independently selected from:

(1) —C(=O)OH;
(2) —C(=O)OR$^1$, wherein R$^1$ is independently as defined in (20), (21), (22) or (23);
(3) —C(=O)NR$^2$R$^3$ or —C(=S)NR$^2$R$^3$, wherein each of R$^2$ and R$^3$ is independently —H; or as defined in (20), (21), (22) or (23); or R$^2$ and R$^3$ taken together with the nitrogen atom to which they are attached form a ring having from 3 to 7 ring atoms;
(4) —C(=O)R$^4$, wherein R$^4$ is independently as defined in (20), (21), (22) or (23);
(5) —F, —Cl, —Br, —I;
(6) —CN;
(7) —NO$_2$;
(8) —OH;
(9) —OR$^5$, wherein R$^5$ is independently as defined in (20), (21), (22) or (23);
(10) —SH;
(11) —SR$^6$, wherein R$^6$ is independently as defined in (20), (21), (22) or (23);
(12) —OC(=O)R$^7$, wherein R$^7$ is independently as defined in (20), (21), (22) or (23);
(13) —NR$^8$R$^9$, wherein each of R$^8$ and R$^9$ is independently —H; or as defined in (20), (21), (22) or (23); or R$^8$ and R$^9$ taken together with the nitrogen atom to which they are attached form a ring having from 3 to 7 ring atoms;
(14) —NR$^{10}$C(=O)R$^{11}$ or —NR$^{10}$C(=S)R$^{11}$, wherein R$^{10}$ is independently —H; or as defined in (20), (21), (22) or (23); and R$^{11}$ is independently —H, or as defined in (20), (21), (22) or (23);
(15) —NR$^{12}$C(=O)NR$^{13}$R$^{14}$ or —NR$^{12}$C(=S)NR$^{13}$R$^{14}$, wherein R$^{12}$ is independently —H; or as defined in (20), (21), (22) or (23); and each of R$^{13}$ and R$^{14}$ is independently —H; or as defined in (20), (21), (22) or (23); or R$^{13}$ and R$^{14}$ taken together with the nitrogen atom to which they are attached form a ring having from 3 to 7 ring atoms;
(16) —NR$^{15}$SO$_2$R$^{16}$, wherein R$^{15}$ is independently —H; or as defined in (20), (21), (22) or (23); and R$^{16}$ is independently —H, or as defined in (20), (21), (22) or (23);
(17) —SO$_2$R$^{17}$, wherein R$^{17}$ is independently as defined in (20), (21), (22) or (23);
(18) —OSO$_2$R$^{18}$ and wherein R$^{18}$ is independently as defined in (20), (21), (22) or (23);
(19) —SO$_2$NR$^{19}$R$^{20}$, wherein each of R$^{19}$ and R$^{20}$ is independently —H; or as defined in (20), (21), (22) or (23); or R$^{19}$ and R$^{20}$ taken together with the nitrogen atom to which they are attached form a ring having from 3 to 7 ring atoms;
(20) $C_{5-20}$aryl-$C_{1-7}$alkyl, for example, wherein $C_{5-20}$aryl is as defined in (21); unsubstituted or substituted with one or more groups as defined in (1) to (27);
(21) $C_{5-20}$aryl, including $C_{6-20}$carboaryl and $C_{5-20}$heteroaryl; unsubstituted or substituted with one or more groups as defined in (1) to (27);
(22) $C_{3-20}$heterocyclyl; unsubstituted or substituted with one or more groups as defined in (1) to (27);
(23) $C_{1-17}$alkyl, including:
 unsaturated $C_{1-7}$alkyl, e.g., $C_{2-7}$alkenyl and $C_{2-7}$alkynyl;
 cyclic $C_{1-7}$alkyl, e.g., $C_{3-7}$cycloalkyl $C_{3-7}$cycloalkenyl, $C_{3-7}$cycloalkynyl;
 $C_{1-7}$alkyl substituted with one or more groups as defined in (1) to (22) and (24) to (27),
 e.g., halo-$C_{1-7}$alkyl;
 e.g., amino-$C_{1-7}$alkyl (e.g., —(CH$_2$)$_w$-amino, w is 1, 2, 3, or 4);
 e.g., carboxy-$C_{1-7}$alkyl (e.g., —(CH$_2$)W—COOH, w is 1, 2, 3, or 4);
 e.g., hydroxy-$C_{1-7}$alkyl (e.g., —(CH$_2$)$_w$—OH, w is 1, 2, 3, or 4);
 e.g., $C_{1-7}$alkoxy-$C_{1-7}$alkyl (e.g., —(CH$_2$)$_w$—O—$C_{1-7}$alkyl, w is 1, 2, 3, or 4);
(24) =O;
(25) =NR$^{21}$, wherein R$^{21}$ is independently —H; or as defined in (20), (21), (22) or (23);
(26) =NOH;
(27) —P(=O)(OR$^{22}$)$_2$ and —OP(=O)(OR$^{22}$)$_2$, wherein R$^{22}$ is independently —H; or as defined in (20), (21), (22) or (23).

In one embodiment, each of the substituents (e.g., $R^A$) is independently selected from:

(1) —C(=O)OH;
(2) —C(=O)OMe, —C(=O)OEt, —C(=O)O(iPr), —C(=O)O(tBu); —C(=O)O(cPr); —C(=O)OCH$_2$CH$_2$OH, —C(=O)OCH$_2$CH$_2$OMe, —C(=O)OCH$_2$CH$_2$OEt; —C(=O)OPh, —C(=O)OCH$_2$Ph;
(3) —(C=O)NH$_2$, —(C=O)NMe$_2$, —(C=O)NEt$_2$, —(C=O)N(iPr)$_2$, —(C=O)N(CH$_2$CH$_2$OH)$_2$; —(C=O)-morpholino, —(C=O)NHPh, —(C=O)NHCH$_2$Ph;
(4) —(C=O)Me, —(C=O)Et, —(C=O)(tBu), —(C=O)-cHex, —(C=O)Ph; —(C=O)CH$_2$Ph;
(5) —F, —Cl, —Br, —I;
(6) —CN;
(7) —NO$_2$;
(8) —OH;
(9) —OMe, —OEt, —O(iPr), —O(tBu), —OPh, —OCH$_2$Ph; —OCF$_3$, —OCH$_2$CF$_3$;
 —OCH$_2$CH$_2$OH, —OCH$_2$CH$_2$OMe, —OCH$_2$CH$_2$OEt;
 —OCH$_2$CH$_2$NH$_2$, —OCH$_2$CH$_2$NMe$_2$, —OCH$_2$CH$_2$N(iPr)$_2$;
 —OPh-Me, —OPh-OH, —OPh-OMe, —OPh-F, —OPh-Cl, —OPh-Br, —OPh-I;
(10) —SH;
(11) —SMe, —SEt, —SPh, —SCH$_2$Ph;
(12) —OC(=O)Me, —OC(=O)Et, —OC(=O)(iPr), —OC(=O)(tBu); —OC(=O)(cPr); —OC(=O)CH$_2$CH$_2$OH, —OC(=O)CH$_2$CH$_2$OMe, —OC(=O)CH$_2$CH$_2$OEt; —OC(=O)Ph, —OC(=O)CH$_2$Ph;
(13) —NH$_2$, —NHMe, —NHEt, —NH(iPr), —NMe$_2$, —NEt$_2$, —N(iPr)$_2$, —N(CH$_2$CH$_2$OH)$_2$; —NHPh, —NHCH$_2$Ph; piperidino, piperazino, morpholino;
(14) —NH(C=O)Me, —NH(C=O)Et, —NH(C=O)Ph, —NHC(=O)CH$_2$Ph; —NMe(C=O)Me, —NMe(C=O)Et, —NMe(C=O)Ph, —NMeC(=O)CH$_2$Ph;
(15) —NH(C=O)NH$_2$, —NH(C=O)NHMe, —NH(C=O)NHEt, —NH(C=O)NPh, —NH(C=O)NHCH$_2$Ph; —NH(C=S)NH$_2$, —NH(C=S)NHMe, —NH(C=S)NHEt, —NH(C=S)NPh, —NH(C=S)NHCH$_2$Ph;
(16) —NHSO$_2$Me, —NHSO$_2$Et, —NHSO$_2$Ph, —NHSO$_2$PhMe, —NHSO$_2$CH$_2$Ph;
 —NMeSO$_2$Me, —NMeSO$_2$Et, —NMeSO$_2$Ph, —NMeSO$_2$PhMe, —NMeSO$_2$CH$_2$Ph;
(17) —SO$_2$Me, —SO$_2$CF$_3$, —SO$_2$Et, —SO$_2$Ph, —SO$_2$PhMe, —SO$_2$CH$_2$Ph;
(18) —OSO$_2$Me, —OSO$_2$CF$_3$, —OSO$_2$Et, —OSO$_2$Ph, —OSO$_2$PhMe, —OSO$_2$CH$_2$Ph;
(19) —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph;

(20) —CH₂Ph, —CH₂Ph-Me, —CH₂Ph-OH, —CH₂Ph-F, —CH₂Ph-Cl;
(21) -Ph, -Ph-Me, -Ph-OH, -Ph-OMe, -Ph-F, -Ph-Cl, -Ph-Br, -Ph-I;
pyridyl, pyrazinyl, pyrimidinyl, pyridazinyl; furanyl, thiophenyl, pyrrolyl, imidazolyl, pyrazolyl, oxazolyl, thiazolyl;
(22) pyrrolidinyl, piperidinyl, azepinyl, tetrahydropyranyl, morpholinyl, azetidinyl,
piperazinyl, imidazolinyl, piperazinedionyl, and oxazolinonyl;
(23) -Me, -Et, -nPr, -iPr, -nBu, -iBu, -sBu, -tBu, -nPe;
-cPr, -cHex; —CH=CH₂, —CH₂—CH=CH₂;
—CF₃, —CHF₂, —CH₂F, —CCl₃, —CBr₃, —CH₂CH₂F, —CH₂CHF₂, and —CH₂CF₃;
—CH₂OH, —CH₂OMe, —CH₂OEt, —CH₂NH₂, —CH₂NMe₂;
—CH₂CH₂OH, —CH₂CH₂OMe, —CH₂CH₂OEt, —CH₂CH₂CH₂NH₂, —CH₂CH₂NMe₂;
(24) =O;
(25) =NH, =NMe; =NEt;
(26) =NOH;
(27) —OP(=O)(OH)₂, —P(=O)(OH)₂, —OP(=O)(OMe)₂, —P(=O)(OMe)₂.

In one embodiment, each of the substituents (e.g., $R^P$) is independently selected from:
(1) —C(=O)OH;
(2) —C(=O)OMe, —C(=O)OEt, —C(=O)O(tBu), —C(=O)OPh;
(3) —C(=O)NH₂, —C(=O)NHMe, —C(=O)NMe₂, —C(=O)NHPh;
(4) —C(=O)Me;
(5) —F, —Cl, —Br, —I;
(6) —CN;
(7) —NO₂;
(8) —OH;
(9) —OMe, —OEt, —O(iPr), —O(nPr), —O(tBu), —OPh, —OBn;
(11) —SMe;
(12) —OC(C=O)Me, —OC(C=O)Et, —OC(C=O)(tBu), —OC(C=O)Ph;
(13) —NH₂, —NHMe, —NMe₂, —NHEt, —NEt₂;
(14) —NHC(=O)Me, —NHC(=O)Et, —NHC(=O)Ph;
(17) —S(=O)₂Me, —S(=O)₂Et, —S(=O)₂Ph.
(19) —SO₂NH₂,
(21) -Ph;
(23) -Me, -Et, -iPr, -nPr, -cPr, -tBu, —CF₃;
(27) —P(=O)(OMe)₂.

In one embodiment, each of the substituents (e.g., $R^P$) is independently selected from:
(1) —C(=O)OH;
(2) —C(=O)OMe, —C(=O)OEt, —C(=O)O(tBu), —C(=O)OPh;
(3) —C(=O)NH₂, —C(=O)NHMe, —C(=O)NMe₂, —C(=O)NHPh;
(4) —C(=O)Me;
(5) —F, —Cl, —Br, —I;
(6) —CN;
(7) —NO₂;
(8) —OH;
(9) —OMe, —OEt, —O(iPr), —O(nPr), —O(tBu), —OPh, —OBn, —OCF₃;
(11) —SMe;
(12) —OC(C=O)Me, —OC(C=O)Et, —OC(C=O)(tBu), —OC(C=O)Ph;
(13) —NH₂, —NHMe, —NMe₂, —NHEt, —NEt₂;
(14) —NHC(=O)Me, —NHC(=O)Et, —NHC(=O)Ph;
(17) —S(=O)₂Me, —S(=O)₂Et, —S(=O)₂Ph.
(19) —SO₂NH₂,
(21) -Ph;
(23) -Me, -Et, -iPr, -nPr, -cPr, -tBu, —CF₃;
(27) —P(=O)(OMe)₂.

In one embodiment, each of the substituents (e.g., $R^P$) is independently selected from: -Me, —F, —Cl, —Br, —I, —OH, —OMe, —NH₂, —NMe₂, —NO₂, —CN, —CF₃, —OCF₃, —C(=O)Me, —C(=O)OH, -Ph, —OEt, —SMe.

In one embodiment, each of the substituents (e.g., $R^P$) is independently selected from: -Me, —F, —Cl, —Br, —I, —OH, —OMe, —NH₂, —NMe₂, —NO₂, —CN, —CF₃, and —OCF₃.

In one embodiment, each of the substituents (e.g., $R^P$) is independently selected from: -Me, —F, —Cl, —Br, —I, —OH, —OMe, —NH₂, —NMe₂, —NO₂, and —CN.

In one embodiment, each of the substituents (e.g., $R^P$) is independently selected from: -Me, —F, —Cl, —OH, —OMe, —NH₂, —NMe₂, —NO₂, and —CN.

In one embodiment, each of the substituents (e.g., $R^P$) is independently selected from: —F, —Cl, —Br, —I, —NO₂, and —OH.

In one embodiment, each of the substituents (e.g., $R^P$) is independently selected from: —F, —Cl, —Br, and —I, —NO₂.

In one embodiment, each of the substituents (e.g., $R^P$) is independently selected from: —F, —Cl, —Br, —I.

In one embodiment, each of the substituents (e.g., $R^P$) is independently selected from: —F and —Br.

In one embodiment, each of the substituents (e.g., $R^P$) is: —F.

Examples of Some Preferred Fluoro-Substituted Phenyl Ar¹ Groups

Some examples of substituted phenyl groups, suitable as Ar¹, include the following:

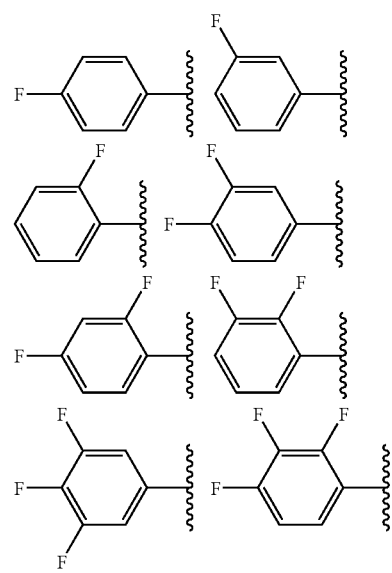

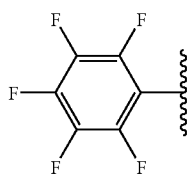
One especially preferred substituted phenyl group, suitable as Ar¹, is:
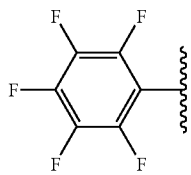
Examples of Some Preferred Substituted Biphenyl-4-yl Ar¹ Groups
Some examples of substituted biphenyl-4-yl groups, suitable as Ar¹, include the following:
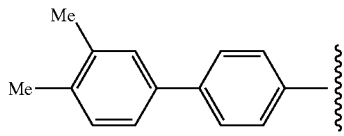
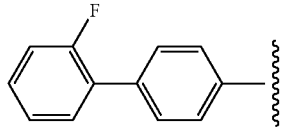
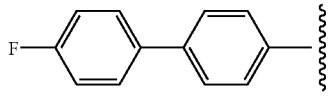
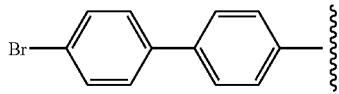
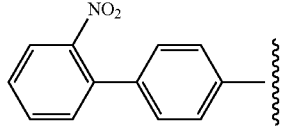
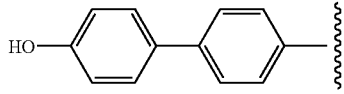
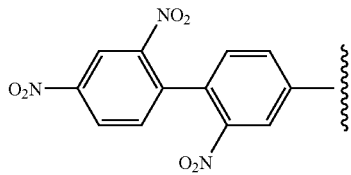
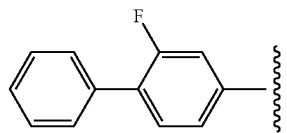
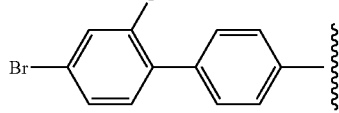
Some additional examples of substituted biphenyl-4-yl groups, suitable as Ar¹, include the following:
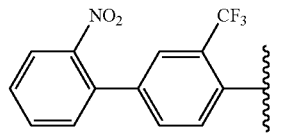
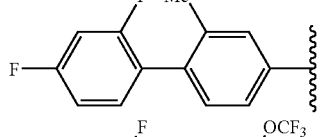
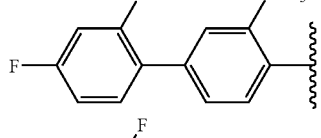
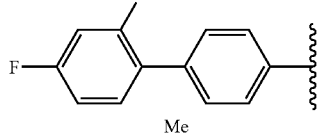
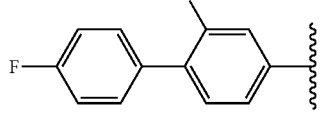
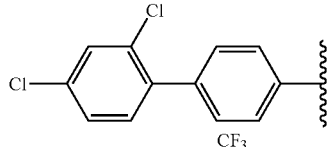
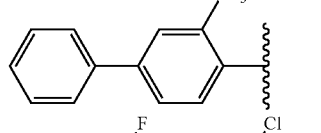
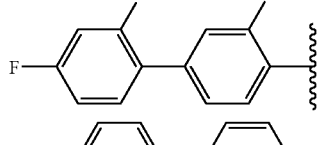
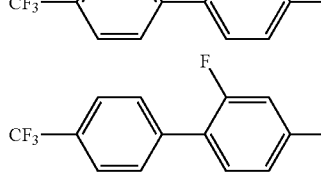

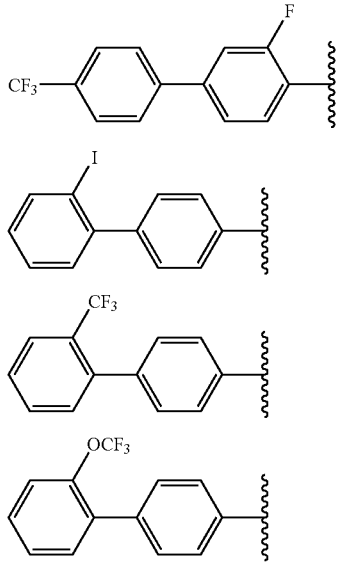
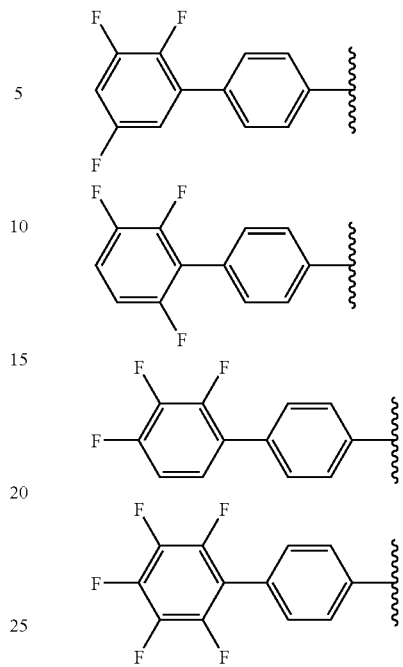
Examples of Some Preferred Fluoro-Substituted Biphenyl-4-yl Ar¹ Groups
Some examples of substituted biphenyl-4-yl groups, suitable as Ar¹, include the following:
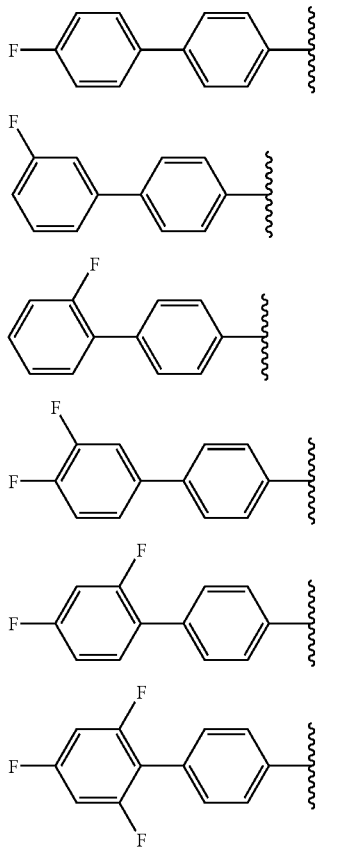
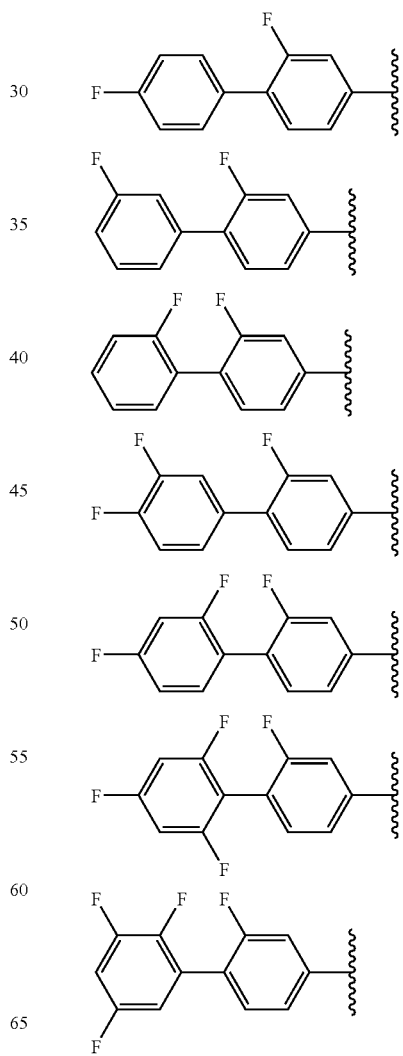

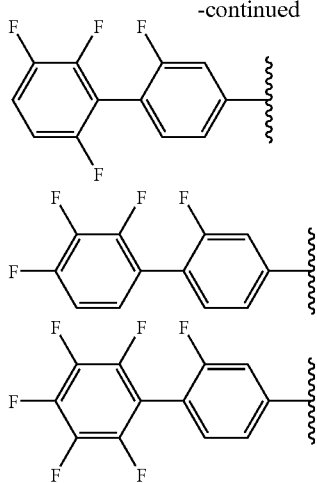

Additional examples of biphenyl-4-yl groups, suitable as Ar$^1$, appear in the "Examples of Specific Embodiments" below.

The Group R$^N$

The sulfonamide nitrogen substituent, R$^N$, is independently-H, acyl (e.g., C$_{1-7}$alkyl-acyl; C$_{5-20}$aryl-acyl; C$_{5-20}$aryl-C$_{1-7}$alkyl-acyl), C$_{5-20}$aryl-C$_{1-7}$alkyl, C$_{3-20}$heterocyclyl, or C$_{1-7}$alkyl, and is optionally substituted, for example, with one or more substituents described under the heading "Phenyl Substituents, R$^P$" above.

In one embodiment, R$^N$ is independently —H, or as defined in (4), (20), (21), (22), or (23).

In one embodiment, R$^N$ is independently unsubstituted.

In one embodiment, R$^N$ is independently substituted.

In one embodiment, R$^N$ is independently —H or C$_{1-7}$alkyl, and is optionally substituted.

In one embodiment, R$^N$ is independently —H or unsubstituted C$_{1-7}$alkyl.

In one embodiment, R$^N$ is independently —H or -Me.

In one embodiment, R$^N$ is independently —H.

The Group R$^{alk}$

The alkylene group, R$^{alk}$, is a C$_{2-10}$alkylene group, and is optionally substituted.

The term "C$_{2-10}$alkylene," as used herein, pertains to a bidentate moiety obtained by removing two hydrogen atoms, either both from the same carbon atom, or one from each of two different carbon atoms, of a hydrocarbon compound having from 2 to 10 carbon atoms, which may be aliphatic or alicyclic, or a combination thereof, and which may be saturated, partially unsaturated, or fully unsaturated. The prefix (i.e., "C$_{2-10}$") denotes the number of carbon atoms in the moiety.

In one embodiment, R$^{alk}$ is C$_{3-10}$alkylene; C$_{4-10}$alkylene;

In one embodiment, R$^{alk}$ is C$_{2-8}$alkylene; C$_{3-8}$alkylene; C$_{4-8}$alkylene.

In one embodiment, R$^{alk}$ is C$_{2-7}$alkylene; C$_{3-7}$alkylene; C$_{4-7}$alkylene.

In one embodiment, R$^{alk}$ is C$_{2-6}$alkylene; C$_{3-6}$alkylene; C$_{4-6}$alkylene.

In one embodiment, R$^{alk}$ is C$_3$alkylene; C$_4$alkylene; C$_5$alkylene; C$_6$alkylene.

In one embodiment, R$^{alk}$ is an aliphatic group.

In one embodiment, R$^{alk}$ is a branched group.

In one embodiment, R$^{alk}$ is a linear group.

In one embodiment, R$^{alk}$ is a partially unsaturated aliphatic group.

In one embodiment, R$^{alk}$ is a fully saturated aliphatic group.

In one embodiment, R$^{alk}$ is a partially unsaturated branched group.

Examples of such groups include, but are not limited to, the following:
—C(Me)=CH—, —CH=C(Me)—, —C(Me)=C(Me)—, —C(Et)=CH—, —CH=C(Et)-, —C(Et)=C(Et)-, —C(Me)=CH—CH$_2$—, —CH=C(Me)-CH$_2$—, —CH=CH—CH(Me)—, —C(Et)=CH—CH$_2$—, —CH=C(Et)-CH$_2$—, —CH=CH—CH(Et)-, —C(Me)=CH—CH$_2$CH$_2$—, —CH=C(Me)-CH$_2$CH$_2$—, —CH=CH—CH(Me)CH$_2$—, —C(Et)=CH—CH$_2$CH$_2$—, —CH=C(Et)-CH$_2$CH$_2$—, and —CH=CH—CH(Et)CH$_2$—.

In one embodiment, R$^{alk}$ is a fully saturated branched group.

Examples of such groups include, but are not limited to, the following:
—CH(Me)—, —CH(Et)-, —CH(Me)CH$_2$—, —CH(Et)CH$_2$—, —CH$_2$CH(Me)—, —CH$_2$CH(Et)-, —CH(Me)CH$_2$CH$_2$—, —CH$_2$CH(Me)CH$_2$—, —CH$_2$CH$_2$CH(Me)—, —CH(Et)CH$_2$CH$_2$—, —CH$_2$CH(Et)CH$_2$—, —CH$_2$CH$_2$CH(Et)-, —CH(Me)CH$_2$CH$_2$CH$_2$—, —CH$_2$CH(Me)CH$_2$CH$_2$—, —CH(Et)CH$_2$CH$_2$CH$_2$—, and —CH$_2$CH(Et)CH$_2$CH$_2$—.

In one embodiment, R$^{alk}$ is a partially unsaturated linear group.

Examples of such groups include, but are not limited to, the following:
—CH=CH— (vinylene), —CH=CH—CH$_2$—, —CH$_2$—CH=CH—, —CH=CH—CH$_2$—CH$_2$—, —CH$_2$—CH—CH=CH—, —CH=CH—CH=CH—, —CH=CH—CH$_2$—CH$_2$—CH$_2$—, —CH=CH—CH=CH—CH$_2$—, —CH=CH—CH$_2$—CH=CH—, —CH=CH—CH=CH—CH$_2$—CH$_2$—, and —CH=CH—CH$_2$—CH$_2$—CH=CH—.

In one embodiment, R$^{alk}$ is a fully saturated linear group.

Examples of such groups include —(CH$_2$)$_2$— (ethylene), —(CH$_2$)$_3$— (propylene), —(CH$_2$)$_4$-(butylene), —(CH$_2$)$_5$— (pentylene), —(CH$_2$)$_6$— (hexylene), —(CH$_2$)$_7$— (heptylene), —(CH$_2$)$_8$-(octylene), —(CH$_2$)$_9$— (nonylene), and —(CH$_2$)$_{10}$— (decylene).

In one embodiment, R$^{alk}$ is —(CH$_2$)$_n$— where n is an integer from 2 to 10.

In one embodiment, n is from 2 to 10; from 3 to 10; from 4 to 10.

In one embodiment, n is from 2 to 8; from 3 to 8; from 4 to 8.

In one embodiment, n is from 2 to 7; from 3 to 7; from 4 to 7.

In one embodiment, n is from 2 to 6; from 3 to 6; from 4 to 6.

In one embodiment, R$^{alk}$ is —(CH$_2$)$_4$—, —(CH$_2$)$_5$—, or —(CH$_2$)$_6$—.

In one embodiment, R$^{alk}$ is —(CH$_2$)$_4$— or —(CH$_2$)$_5$—.

In one embodiment, R$^{alk}$ is —(CH$_2$)$_3$—. In one embodiment, R$^{alk}$ is —(CH$_2$)$_4$—.

In one embodiment, R$^{alk}$ is —(CH$_2$)$_5$—. In one embodiment, R$^{alk}$ is —(CH$_2$)$_6$—.

In one embodiment, R$^{alk}$ is optionally substituted (i.e., unsubstituted or substituted).

In one embodiment, R$^{alk}$ is unsubstituted.

In one embodiment, R$^{alk}$ is substituted.

In one embodiment, $R^{alk}$ is optionally substituted with one or more substituents selected from: halogen, hydroxy, ether (e.g., $C_{1-7}$alkoxy), amino, and amido.

In one embodiment, $R^{alk}$ is optionally substituted with one or more substituents selected from: —F, —Cl, —Br, and —I.

In one embodiment, $R^{alk}$ is optionally substituted with one or more —F groups.

In one embodiment, $R^{alk}$ is:

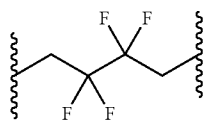

Substitutions in the Backbone of $R^{alk}$

In one embodiment, one or more carbon atoms of the backbone chain of $R^{alk}$ is replaced with a moiety selected from: —O—, —S—, —S(=O)—, —S(=O)$_2$—, and —NH—. In one embodiment, only one carbon atom is replaced.

In one embodiment, $R^{alk}$ is —(CH$_2$)$_n$— where n is as defined above (e.g., an integer from 2 to 10); and one or more —CH$_2$— groups is replaced with a moiety selected from: —O—, —S—, —S(=O)—, —S(=O)$_2$—, and —NH— (e.g., e.g., —CH$_2$—O—CH$_2$—). In one embodiment, only one —CH$_2$—group is replaced.

In one embodiment, the replaced carbon atom, or replaced —CH$_2$— group, is not at a terminal position within $R^{alk}$ (e.g., —CH$_2$—O—CH$_2$— but not —O—CH$_2$—CH$_2$— or —CH$_2$—CH$_2$—O—).

The Group Q

In one embodiment, Q is independently —H or an organic group (i.e., a group having at least carbon and hydrogen atoms) having from 1 to 30 atoms selected from carbon, nitrogen, oxygen, sulfur, phosphorus, fluorine, chlorine, bromine, and iodine.

In one embodiment, Q is independently an organic group having from 1 to 30 atoms selected from carbon, nitrogen, oxygen, sulfur, phosphorus, fluorine, chlorine, bromine, and iodine.

In one embodiment, Q is independently an organic group having from 1 to 30 atoms selected from carbon, nitrogen, oxygen, sulfur, phosphorus, fluorine, chlorine, bromine, and iodine, which is linked via an oxygen atom (e.g., oxy-type groups).

In one embodiment, Q is independently an organic group having from 1 to 30 atoms selected from carbon, nitrogen, oxygen, sulfur, phosphorus, fluorine, chlorine, bromine, and iodine, which is linked via an nitrogen atom (e.g., amine-type groups).

The Group Q: Oxy-Type Groups

In one embodiment, Q is independently —OH or —OR$^{OT}$.

In one embodiment, Q is independently —OH.

In one embodiment, $R^{OT}$, if present, is independently an organic group (i.e., a group having at least carbon and hydrogen atoms) having from 1 to 30 atoms selected from carbon, nitrogen, oxygen, sulfur, phosphorus, fluorine, chlorine, bromine, and iodine.

In one embodiment, the group —OR$^{OT}$, if present, is independently selected from:

—O—R$^{E1}$;
—O—C(=O)—R$^{E2}$;
—O—C(=O)—O—R$^{E3}$;
—O—C(=O)—O—SO$_3$R$^{E4}$;
—O—C(=O)—O—(CH$_2$)$_n$—COOR$^{E5}$;
—O—C(=O)—(CH$_2$)$_n$—NR$^{NE1}$R$^{NE2}$;
—O—C(=O)—(CH$_2$)$_n$—NR$^{NE3}$—C(=O)R$^{E6}$;
—O—C(=O)—(CH$_2$)$_n$—C(=O)—NR$^{NE4}$R$^{NE5}$;
—O—P(=O)(OR$^{E7}$)(OR$^{E8}$);
—O—R$^{PA}$;

wherein:

each of R$^{E1}$, R$^{E2}$, R$^{E3}$, R$^{E4}$, R$^{E5}$, R$^{E6}$, R$^{E7}$, R$^{E8}$, and R$^{NE3}$, if present, is independently as defined in (20), (21), (22) or (23) above (e.g., $C_{5-20}$aryl-$C_{1-7}$alkyl, $C_{5-20}$aryl, $C_{3-20}$heterocyclyl, or $C_{1-7}$alkyl, and is optionally substituted);

each of R$^{E2}$, R$^{E4}$, R$^{E5}$, R$^{E7}$, R$^{E8}$ and R$^{NE3}$, if present, may additionally be —H; and each of —NR$^{NE1}$R$^{NE2}$ and —NR$^{NE4}$R$^{NE5}$, if present, is independently as defined for —NR$^8$R$^9$ (e.g., —NR$^8$R$^9$, wherein each of R$^8$ and R$^9$ is independently —H or $C_{5-20}$aryl-$C_{1-7}$alkyl, $C_{5-20}$aryl, $C_{3-20}$heterocyclyl, or $C_{1-7}$alkyl, and is optionally substituted, or R$^8$ and R$^9$ taken together with the nitrogen atom to which they are attached form a ring having from 3 to 7 ring atoms).

In one embodiment:

one or more or each of R$^{E1}$, R$^{E2}$, R$^{E3}$, R$^{E4}$, R$^{E5}$, R$^{E6}$, R$^{E7}$, R$^{E8}$, and R$^{NE3}$, if present, is independently as defined in (23) above (e.g., $C_{1-7}$alkyl, and is optionally substituted).

In one embodiment, R$^{NE3}$, if present, is independently —H.

The Group Q: Amino-Type Groups

In one embodiment, Q is independently selected from:

—NR$^{NF1}$R$^{NF2}$.
—NR$^{NF3}$—C(=O)—R$^{F1}$;
—NR$^{NF4}$C(=O)—NR$^{NF5}$R$^{NF6}$;
—NR$^{NF7}$C(=S)—NR$^{NF8}$R$^{NF9}$;
—NR$^{NF10}$C(=NR$^{NF11}$)—NR$^{NF12}$R$^{NF13}$;
—NR$^{NF14}$S(=O)$_2$R$^{F2}$;
—NR$^{NF15}$C(=NR$^{NF16}$)—R$^{F3}$;
—NR$^{NF17}$C(=NR$^{NF18}$)—S—R$^{F4}$;
—NR$^{NF19}$CN;

wherein:

each of R$^{F1}$, R$^{F2}$, R$^{F3}$, R$^{F4}$, R$^{NF3}$, R$^{NF4}$, R$^{NF7}$, R$^{NF10}$, R$^{NF11}$, R$^{NF14}$, R$^{NF15}$, R$^{NF16}$, R$^{NF17}$, R$^{NF18}$, and R$^{NF19}$, if present, is independently as defined in (20), (21), (22) or (23) above (e.g., $C_{5-20}$aryl-$C_{1-7}$alkyl, $C_{5-20}$aryl, $C_{3-20}$heterocyclyl, or $C_{1-7}$alkyl, and is optionally substituted);

each of R$^{F3}$, R$^{F4}$, R$^{NF3}$, R$^{NF4}$, R$^{NF7}$, R$^{NF10}$, R$^{NF11}$, R$^{NF14}$, R$^{NF15}$, R$^{NF16}$, R$^{NF17}$, R$^{NF18}$, and R$^{NF19}$, if present, may additionally be —H; and each of —NR$^{NF1}$R$^{NF2}$, —NR$^{NF5}$R$^{NF6}$, —NR$^{NF8}$R$^{NF9}$, and NR$^{NF12}$R$^{NF13}$, if present, is independently as defined for —NR$^8$R$^9$ (e.g., —NR$^8$R$^9$, wherein each of R$^8$ and R$^9$ is independently —H or $C_{5-20}$aryl-$C_{1-7}$alkyl, $C_{5-20}$aryl, $C_{3-20}$heterocyclyl, or $C_{1-7}$alkyl, and is optionally substituted, or R$^8$ and R$^9$ taken together with the nitrogen atom to which they are attached form a ring having from 3 to 7 ring atoms).

In one embodiment:

one or more or each of R$^{F1}$, R$^{F2}$, R$^{F3}$, R$^{F4}$, R$^{NF3}$, R$^{NF7}$, R$^{NF10}$, R$^{NF11}$, R$^{NF14}$, R$^{NF15}$, R$^{NF16}$, R$^{NF17}$, R$^{NF18}$, and R$^{NF19}$, if present, is independently as defined in (23) (e.g., $C_{1-7}$alkyl, and is optionally substituted).

In one embodiment, one or more or each of R$^{NF3}$, R$^{NF4}$, R$^{NF7}$, R$^{NF10}$, R$^{NF11}$, R$^{NF14}$, R$^{NF15}$, R$^{NF16}$, R$^{NF17}$, R$^{NF18}$, and R$^{NF19}$, if present, is independently —H.

The Group Q: Other Groups

In one embodiment, Q is independently selected from:

—H;
—C(=O)—OH;
—C(=O)—OR$^{G1}$;
—C(=O)—R$^{G2}$;
—S—C(=NR$^{NG1}$)—R$^{G3}$;

—S—C(=NR$^{NG2}$)—S—R$^{G4}$;
—S—C(=NR$^{NG3}$)—NR$^{NG4}$R$^{NG5}$;
—CH(CN)$_2$;
—P(=O)(OR$^{G5}$)(OR$^{G6}$);
—R$^{PA}$;
wherein:

each of R$^{G1}$, R$^{G2}$, R$^{G3}$, R$^{G4}$, R$^{G5}$, R$^{G6}$, R$^{NG1}$, R$^{NG2}$, and R$^{NG3}$, if present, is independently as defined in (20), (21), (22) or (23) above (e.g., C$_{5-20}$aryl-C$_{1-7}$alkyl, C$_{5-20}$aryl, C$_{3-20}$heterocyclyl, or C$_{1-7}$alkyl, and is optionally substituted); and each of R$^{G3}$, R$^{G4}$, R$^{G5}$, R$^{G6}$, R$^{NG1}$, R$^{NG2}$, and R$^{NG3}$, if present, may additionally be —H; and —NR$^{NG4}$R$^{NG5}$, if present, is independently as defined for —NR$^8$R$^9$ (e.g., —NR$^8$R$^9$, wherein each of R$^8$ and R$^9$ is independently —H or C$_{5-20}$aryl-C$_{1-7}$alkyl, C$_{5-20}$aryl, C$_{3-20}$heterocyclyl, or C$_{1-7}$alkyl, and is optionally substituted, or R$^8$ and R$^9$ taken together with the nitrogen atom to which they are attached form a ring having from 3 to 7 ring atoms).

In one embodiment:
one or more or each of R$^{G1}$, R$^{G2}$, R$^{G3}$, R$^{G4}$, R$^{G5}$, R$^{G6}$, R$^{NG1}$, R$^{NG2}$, and R$^{NG3}$, if present, is independently as defined in (23) above (e.g., C$_{1-7}$alkyl, and is optionally substituted).

In one embodiment, one or more or each of R$^{NG1}$, R$^{NG2}$, and R$^{NG3}$, if present, is independently —H.

The Group R$^{PA}$

The group R$^{PA}$, if present, is an organic group incorporating a phosphonic acid group.

Without wishing to be bound by any particular theory, it is believed that phosphonic acid groups act as bone targeting moieties, and improve delivery of the compound to the bone environment.

Examples of bisphosphonate compounds currently in use for the treatment of osteoporosis, Paget's disease, and cancer associated bone disease include the following:

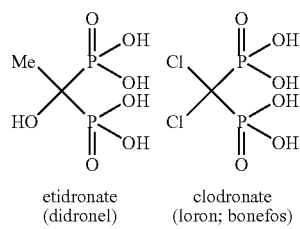

etidronate (didronel)   clodronate (loron; bonefos)

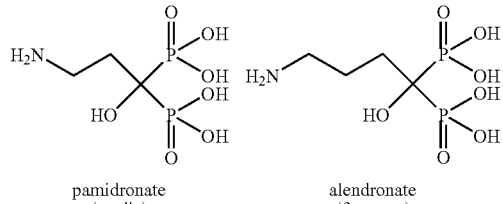

pamidronate (aredia)   alendronate (fosamax)

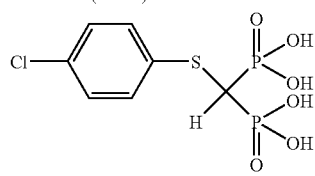

tiludronate (skelid)

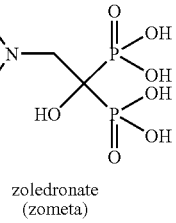

risedronate (actonel)   zoledronate (zometa)

Examples of bisphosphonate compounds currently in development include the following:

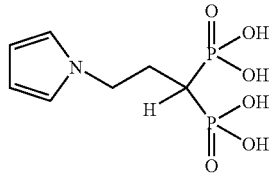

medronate   olpadronate

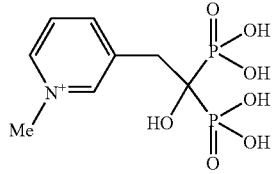

ibandronate

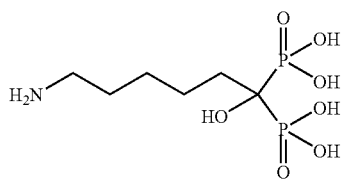

EB-1053

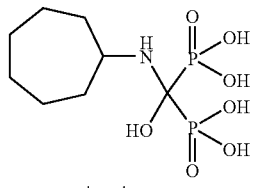

methyl pyridinium analogue neridronate

incadronate

In one embodiment, Q is independently —R$^{PA}$ or —OR$^{PA}$, wherein R$^{PA}$ is an organic group incorporating a phosphonic acid group.

The term "phosphonic acid group," as used herein, pertains to phosphonic acid, and groups derived therefrom, for example: phosphonic acid, and salts (e.g. phosphonates) and esters (e.g., phosphonate esters) thereof.

Examples of such groups are shown below. For the phosphonate esters, the groups R$^1$ and R$^2$ are independently C$_{1-7}$alkyl, C$_{3-20}$heterocyclyl, or C$_{5-20}$aryl, preferably C$_{1-7}$alkyl, e.g., ethyl.

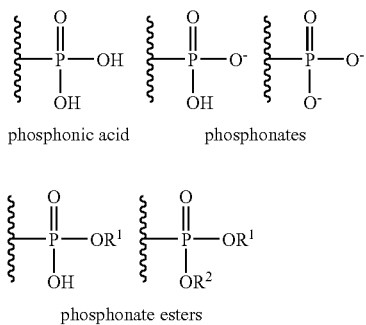

Where the group is a phosphonate bearing a charge of (−1) or (−2), it will be associated with a suitable number of cation or cations of suitable charge. Examples of suitable cations are discussed below.

In one embodiment, R$^{PA}$, if present, is an organic group (i.e., a group comprising at least carbon and hydrogen) having from 5 to 40 atoms, preferably from 5 to 30 atoms, preferably from 5 to 20 atoms, selected from carbon, nitrogen, oxygen, sulfur, phosphorus, fluorine, chloride, bromine, and iodine (and excluding hydrogen), preferably selected from carbon, nitrogen, oxygen, sulfur, and phosphorus, preferably selected from carbon, oxygen, and phosphorus; and incorporates a phosphonic acid group.

In one embodiment, R$^{PA}$, if present, independently incorporates one phosphonic acid group.

In one embodiment, R$^{PA}$, if present, independently incorporates two phosphonic acid groups.

In one embodiment, R$^{PA}$, if present, independently incorporates the following group, or a salt or ester thereof:

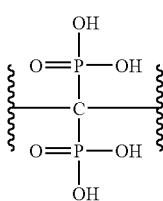

In one embodiment, R$^{PA}$, if present, is the following group, or a salt or ester thereof:

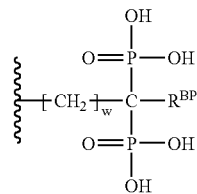

wherein:

w is an integer from 0 to 5; and

R$^{BP}$ is —H, —OH, halo, or C$_{1-7}$alkyl (e.g., as defined in (23) above).

In one embodiment, w is an integer from 0 to 3.

In one embodiment, w is 0, 1, or 2.

In one embodiment, R$^{BP}$ is —H. For example (here the group R$^{PA}$ has 9, 10, and 11 atoms, respectively, selected from carbon, oxygen, and phosphorus):

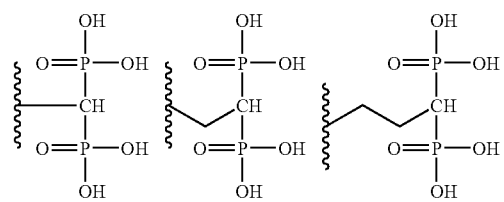

In one embodiment, R$^{BP}$ is —OH. For example (here the group R$^{PA}$ has 12 atoms selected from carbon, oxygen, and phosphorus):

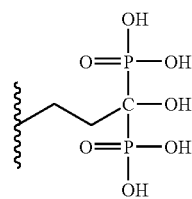

In one embodiment, R$^{BP}$ is —CH$_2$CH$_2$COOH. For example (here the group R$^{PA}$ has 16 atoms selected from carbon, oxygen, and phosphorus):

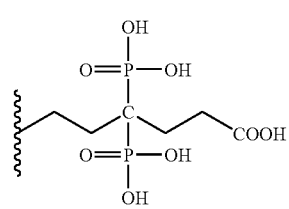

Examples of Specific Embodiments
Some individual embodiments of the present invention include the following compounds (e.g., "sulfonamides" with Q as oxy-type groups, specifically —OH):
ABD-155
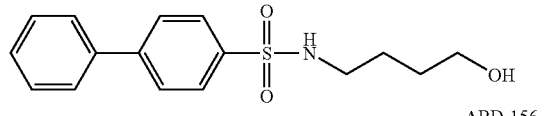
ABD-156
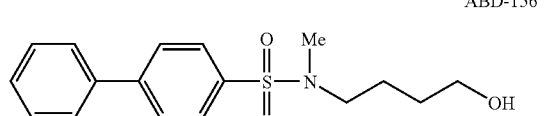
ABD-164
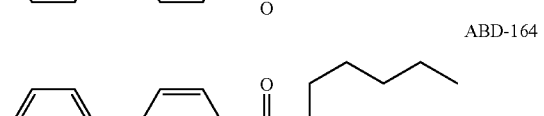
ABD-176
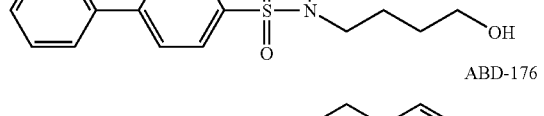
ABD-178
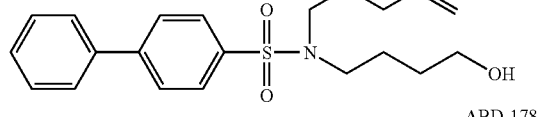
ABD-179
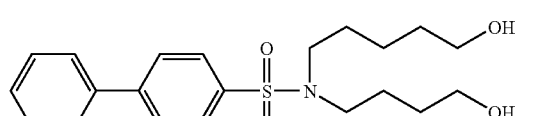
ABD-180
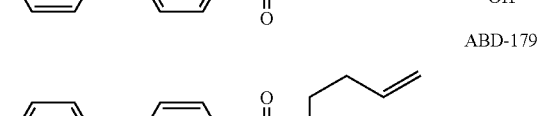
ABD-185
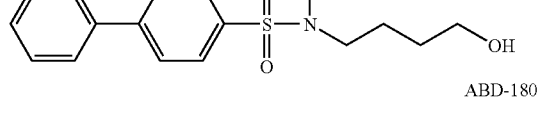
ABD-186
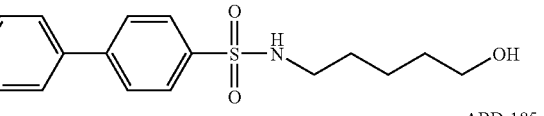
ABD-187
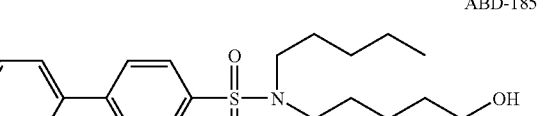
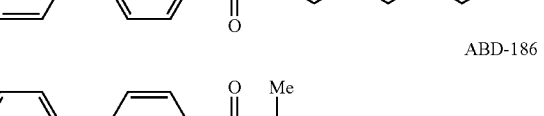
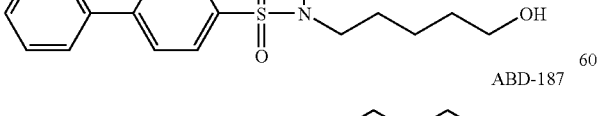
-continued
ABD-188
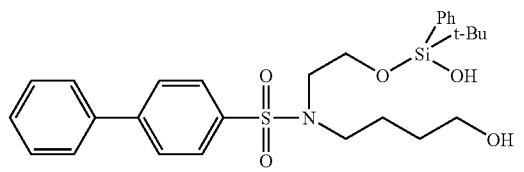
ABD-189
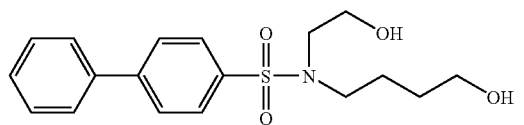
ABD-199
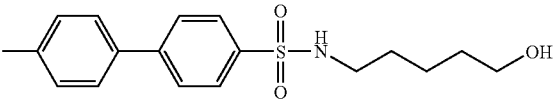
ABD-200
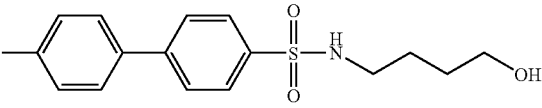
ABD-201
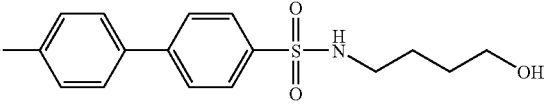
ABD-203
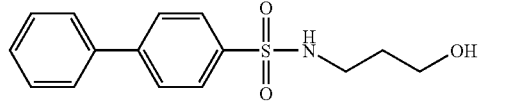
ABD-205
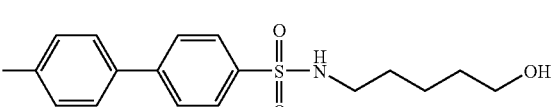
ABD-226
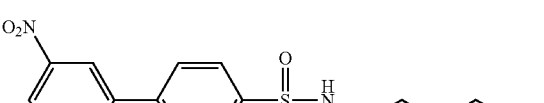
ABD-227
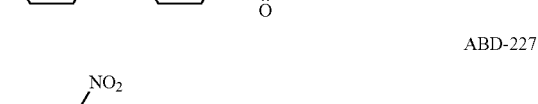
ABD-234
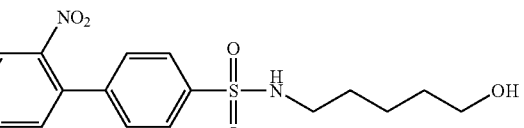

ABD-246
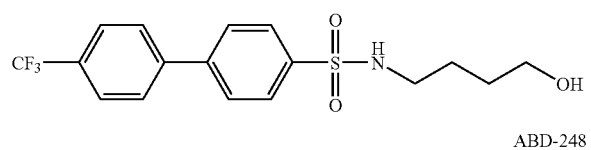
ABD-248
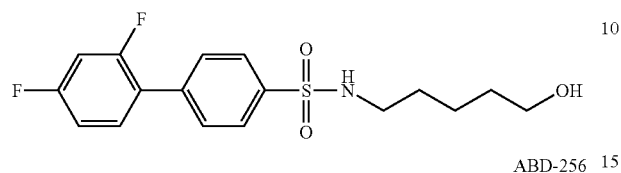
ABD-256
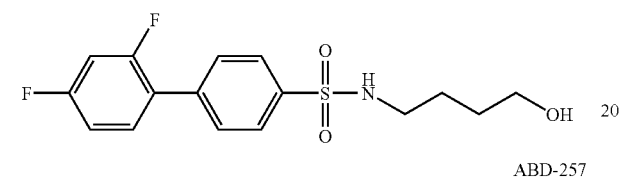
ABD-257
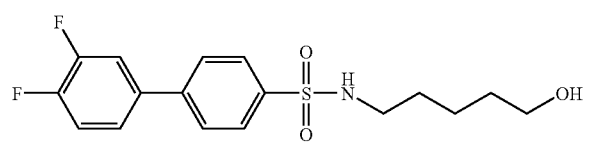
ABD-258
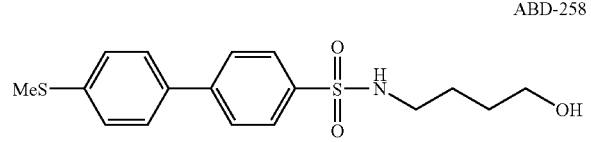
ABD-259
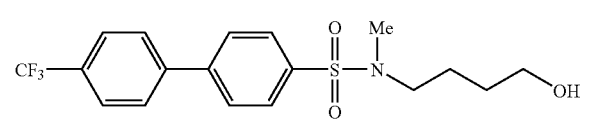
ABD-260
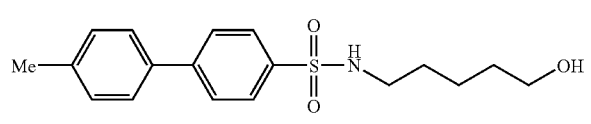
ABD-261
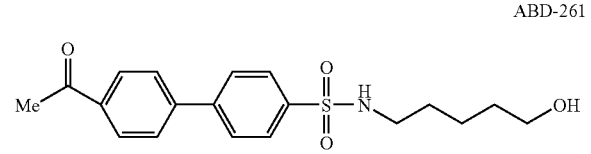
ABD-262
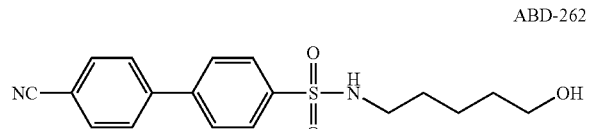
ABD-263
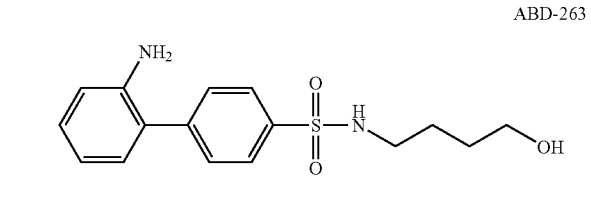
ABD-265
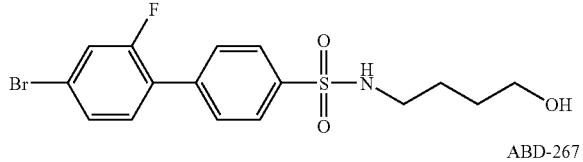
ABD-267
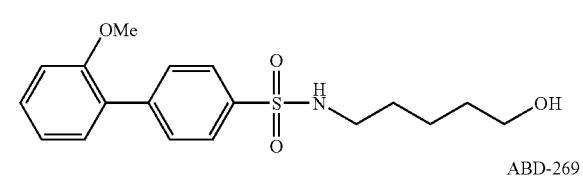
ABD-269
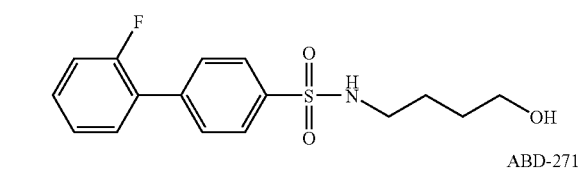
ABD-271
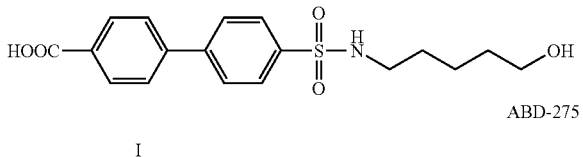
ABD-275
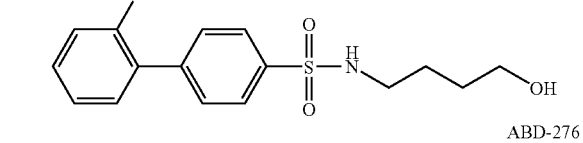
ABD-276
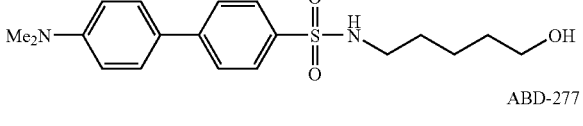
ABD-277
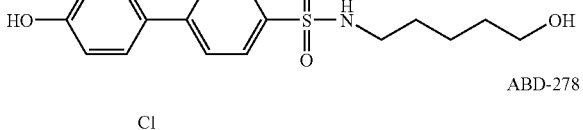
ABD-278
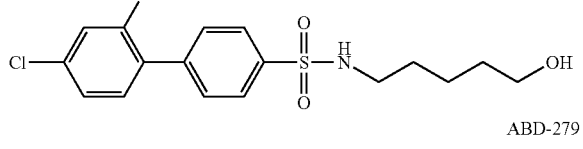
ABD-279
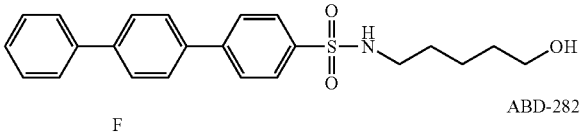
ABD-282
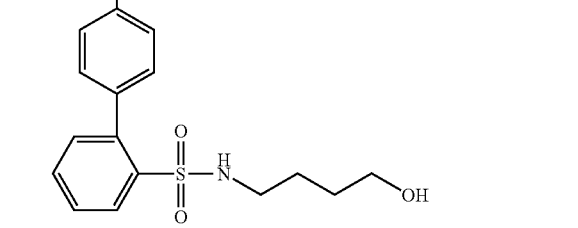

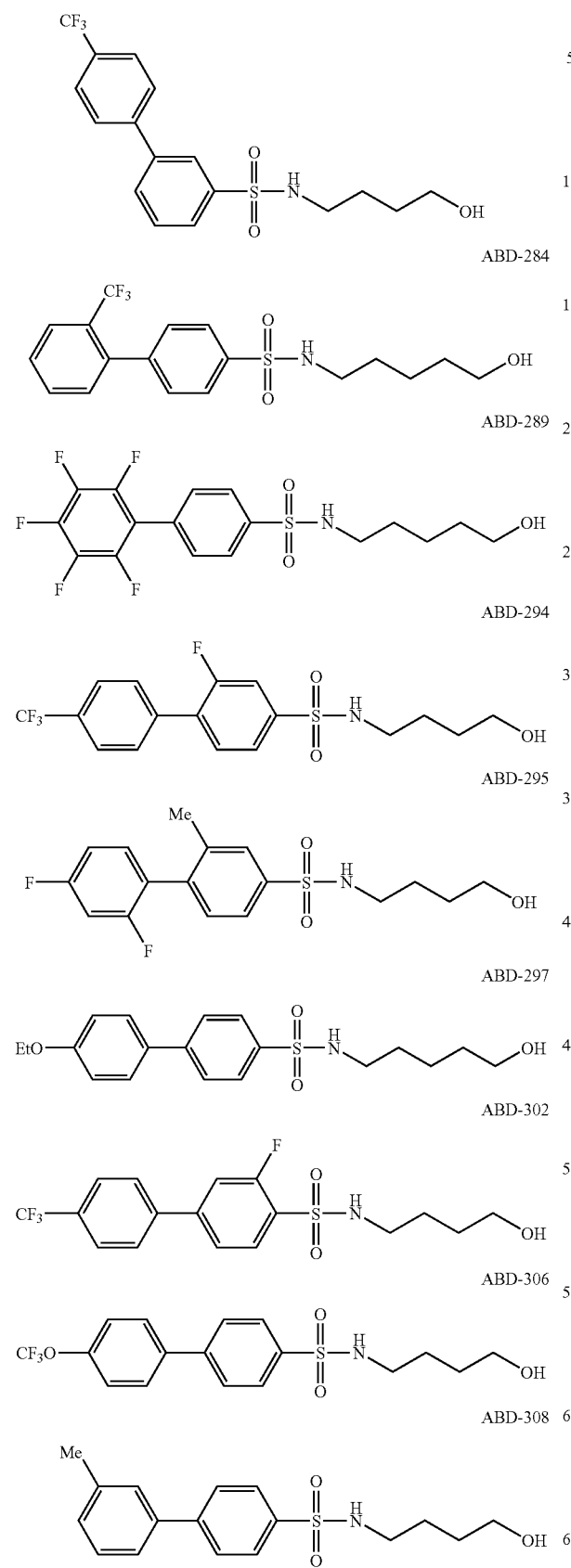
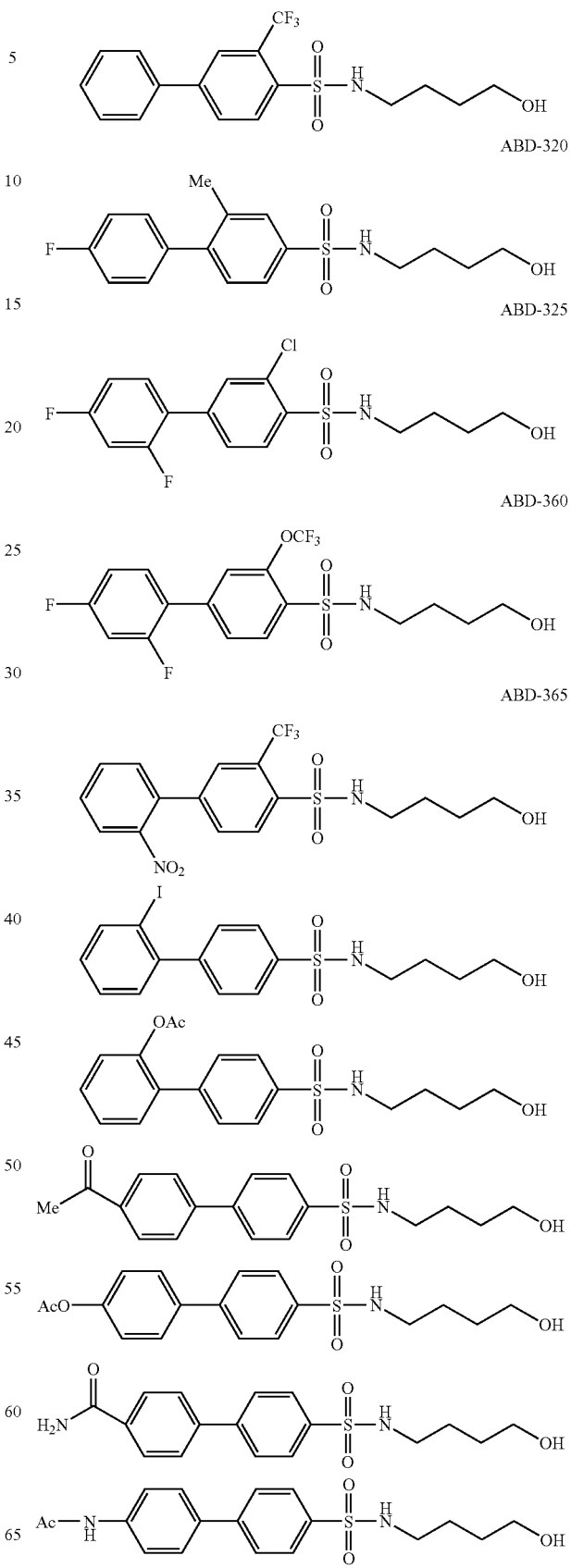

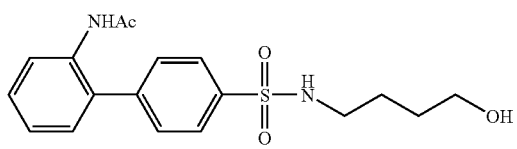

Some individual embodiments of the present invention include the following compounds (e.g., "sulfonamides" with Q as oxy-type groups, specifically —OR$^{OT}$:

ABD-192

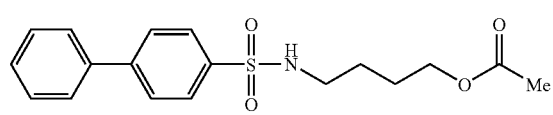

ABD-266

Some individual embodiments of the present invention include the following compounds (e.g., "sulfonamides" with Q as amine-type groups).

ABD-250

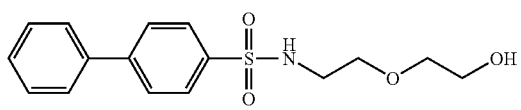

ABD-251

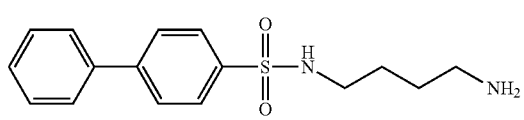

ABD-252

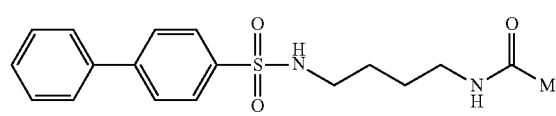

ABD-255

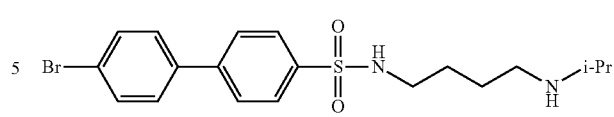

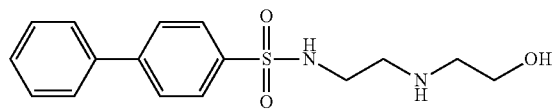

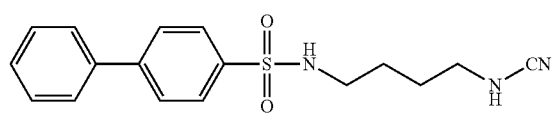

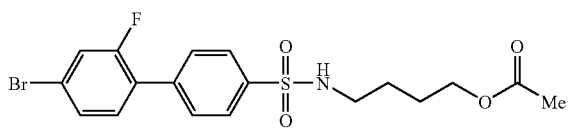

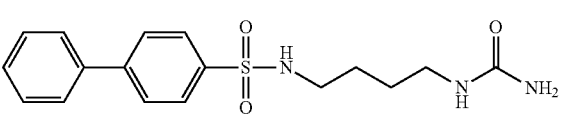

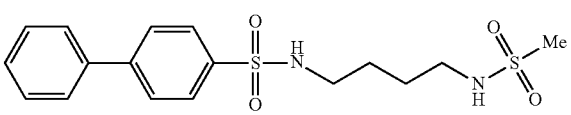

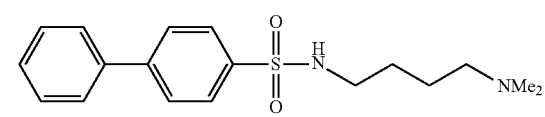

Some individual embodiments of the present invention include the following compounds (e.g., "sulfonamides" with other Q groups).

ABD-222

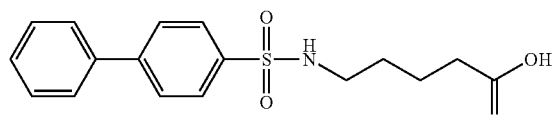

ABD-230

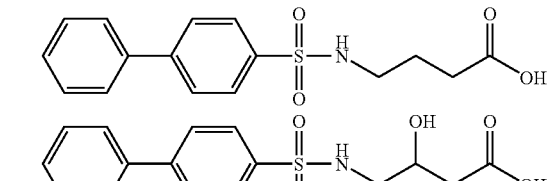

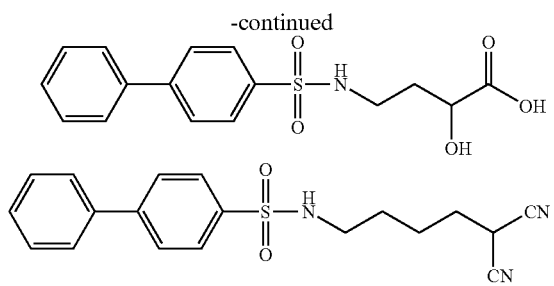

Chemical Terms

The term "carbo," "carbyl," "hydrocarbon" and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked atoms, more preferably 3 to 8 covalently linked atoms, yet more preferably 5 to 6 covalently linked atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene), bridged (e.g., as in norbornane), spiro (e.g., as in spiro[3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The term "monodentate substituents," as used herein, pertains to substituents which have one point of covalent attachment.

The term "monovalent monodentate substituents," as used herein, pertains to substituents which have one point of covalent attachment, via a single bond. Examples of such substituents include halo, hydroxy, and alkyl.

The term "multivalent monodentate substituents," as used herein, pertains to substituents which have one point of covalent attachment, but through a double bond or triple bond. Examples of such substituents include oxo, imino, alkylidene, and alklidyne.

The term "bidentate substituents," as used herein, pertains to substituents which have two points of covalent attachment, and which act as a linking group between two other moieties. Examples of such substituents include alkylene and arylene.

Substituents

The phrase "optionally substituted," as used herein, pertains to a parent group which may be unsubstituted or which may be substituted.

Unless otherwise specified, the term "substituted," as used herein, pertains to a parent group which bears one or more substitutents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

The substituents are described in more detail below.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated, partially unsaturated, or fully unsaturated. Thus, the term "alkyl" includes the sub-classes alkenyl, alkynyl, cycloalkyl, etc., discussed below.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), n-undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Cycloalkyl: The term "cycloalkyl," as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 20 ring atoms (unless otherwise specified). Preferably, each ring has from 3 to 7 ring atoms.

Examples of (unsubstituted) saturated cylcoalkyl groups include, but are not limited to, those derived from: cyclopropane ($C_3$), cyclobutane ($C_4$), cyclopentane ($C_5$), cyclohexane ($C_6$), cycloheptane ($C_7$), norbornane ($C_7$), norpinane ($C_7$), adamantane ($C_{10}$), and decalin (decahydronaphthalene) ($C_{10}$).

Examples of (substituted) saturated cycloalkyl groups, which are also referred to herein as "alkyl-cycloalkyl" groups, include, but are not limited to, methylcyclopropyl, dimethylcyclopropyl, methylcyclobutyl, dimethylcyclobutyl, methylcyclopentyl, dimethylcyclopentyl, methylcyclohexyl, and dimethylcyclohexyl.

Examples of (substituted) unsaturated cyclic alkenyl groups, which are also referred to herein as "alkyl-cycloalkenyl" groups, include, but are not limited to, methylcyclopropenyl, dimethylcyclopropenyl, methylcyclobutenyl, dimethylcyclobutenyl, methylcyclopentenyl, dimethylcyclopentenyl, methylcyclohexenyl, and dimethylcyclohexenyl.

Examples of (substituted) cycloalkyl groups, with one or more other rings fused to the parent cycloalkyl group, include, but are not limited to, those derived from: indene ($C_9$), indan (e.g., 2,3-dihydro-1H-indene) ($C_9$), tetraline (1,2,3,4-tetrahydronaphthalene ($C_{10}$), fluorene ($C_{13}$), phenalene ($C_{13}$). For example, 2H-inden-2-yl is a $C_5$cycloalkyl group with a substituent (phenyl) fused thereto.

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, $—CH=CH_2$), 1-propenyl ($—CH=CH—CH_3$), 2-propenyl (allyl, $—CH—CH=CH_2$), isopropenyl ($—C(CH_3)=CH_2$), butenyl ($C_4$), pentenyl ($C_5$), and hexenyl ($C_6$).

Examples of (unsubstituted) unsaturated cyclic alkenyl groups, which are also referred to herein as "cycloalkenyl" groups, include, but are not limited to, cyclopropenyl ($C_3$), cyclobutenyl ($C_4$), cyclopentenyl ($C_5$), and cyclohexenyl ($C_6$).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, $—C≡CH$) and 2-propynyl (propargyl, $—CH_2—C≡CH$).

Alkylidene: The term "alkylidene," as used herein, pertains to a divalent monodentate moiety obtained by removing two hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidene groups include $C_{1-4}$alkylidene, $C_{1-7}$alkylidene, $C_{1-20}$alkylidene.

Examples of alkylidene groups include, but are not limited to, methylidene ($=CH_2$), ethylidene ($=CH—CH_3$), vinylidene ($=C=CH_2$), and isopropylidene ($=C(CH_3)_2$).

Alkylidyne: The term "alkylidyne," as used herein, pertains to a trivalent monodentate moiety obtained by removing three hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidyne groups include $C_{1-4}$alkylidyne, $C_{1-7}$alkylidyne, $C_{1-20}$alkylidyne.

Examples of alkylidyne groups include, but are not limited to, methylidyne ($≡CH$) and ethylidyne ($≡C—CH_3$).

Carbocyclyl: The term "carbocyclyl," as used herein, pertains to a monovalent moiety obtained by removing a hydrogen atom from a ring atom of a carbocyclic compound, which moiety has from 3 to 20 ring atoms (unless otherwise specified). Preferably, each ring has from 3 to 7 ring atoms.

In this context, the prefixes (e.g., $C_{3-20}$, $C_{3-7}$, $C_{5-6}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$carbocyclyl, $C_{5-10}$carbocyclyl, $C_{3-7}$carbocyclyl, and $C_{5-7}$carbocyclyl.

Examples of carbocyclic groups include, but are not limited to, those described above as cycloalkyl groups; those described below as carboaryl groups.

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{3-7}$heterocyclyl, $C_{5-7}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{3-12}$aryl, $C_{5-12}$aryl, $C_{5-7}$aryl, and $C_{5-6}$aryl.

The ring atoms may be all carbon atoms, as in "carboaryl groups" (e.g., $C_{5-20}$carboaryl).

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$):

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, as in "heteroaryl groups" (e.g., $C_{5-20}$heteroaryl, $C_{5-12}$heteroaryl, $C_{5-7}$heteroaryl, $C_{5-6}$heteroaryl).

Examples of monocyclic heteroaryl groups include, but are not limited to, those derived from:
$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heterocyclic groups (some of which are also heteroaryl groups) which comprise fused rings, include, but are not limited to:
$C_9$heterocyclic groups (with 2 fused rings) derived from benzofuran ($O_1$), isobenzofuran ($O_1$), indole ($N_1$), isoindole ($N_1$), purine ($N_4$) (e.g., adenine, guanine), benzimidazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);
$C_{10}$heterocyclic groups (with 2 fused rings) derived from benzodioxan ($O_2$), quinoline ($N_1$), isoquinoline ($N_1$), benzoxazine ($N_1O_1$), benzodiazine ($N_2$), pyridopyridine ($N_2$), quinoxaline ($N_2$), quinazoline ($N_2$), phthalazine ($N_2$), pteridine ($N_4$);
$C_{13}$heterocyclic groups (with 3 fused rings) derived from carbazole ($N_1$), dibenzofuran ($O_1$), dibenzothiophene ($S_1$); and,
$C_{14}$heterocyclic groups (with 3 fused rings) derived from acridine ($N_1$), xanthene ($O_1$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N═ group may be substituted in the form of an N-oxide, that is, as —N(→O)═ (also denoted —N$^+$(→O$^-$)═). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (═O) groups on ring carbon atoms. Monocyclic examples of such groups include, but are not limited to, those derived from:
$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:
$C_9$: indenedione;
$C_{10}$: tetralone, decalone;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$);
$N_4$: purinone ($C_9$) (e.g., guanine).

Still more examples of cyclic groups which bear one or more oxo (═O) groups on ring carbon atoms include, but are not limited to, those derived from:
cyclic anhydrides (—C(═O)—O—C(═O)— in a ring), including but not limited to maleic anhydride ($C_5$), succinic anhydride ($C_5$), and glutaric anhydride ($C_6$);
cyclic carbonates (—O—C(═O)—O— in a ring), such as ethylene carbonate ($C_5$) and 1,2-propylene carbonate ($C_5$);
imides (—C(═O)—NR—C(═O)— in a ring), including but not limited to, succinimide ($C_5$), maleimide ($C_5$), phthalimide, and glutarimide ($C_6$);
lactones (cyclic esters, —O—C(═O)— in a ring), including, but not limited to, β-propiolactone, γ-butyrolactone, δ-valerolactone (2-piperidone), and ε-caprolactone;
lactams (cyclic amides, —NR—C(═O)— in a ring), including, but not limited to, β-propiolactam ($C_4$), γ-butyrolactam (2-pyrrolidone) ($C_5$), δ-valerolactam ($C_6$), and ε-caprolactam ($C_7$);
cyclic carbamates (—O—C(═O)—NR— in a ring), such as 2-oxazolidone ($C_5$);
cyclic ureas (—NR—C(═O)—NR— in a ring), such as 2-imidazolidone ($C_5$) and pyrimidine-2,4-dione (e.g., thymine, uracil) ($C_6$).

The above alkyl, alkylidene, alkylidyne, heterocyclyl, and aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$alkyl group, a $C_{3-20}$heterocyclyl group, or a $C_{5-20}$aryl group, preferably a $C_{1-7}$alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$alkyl group, a $C_{3-20}$heterocyclyl group, or a $C_{5-20}$aryl group, preferably a $C_{1-7}$alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and R$^2$ is an acyl substituent, for example, a $C_{1-7}$alkyl group, a $C_{3-20}$heterocyclyl group, or a $C_{5-20}$aryl group, preferably hydrogen or a $C_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

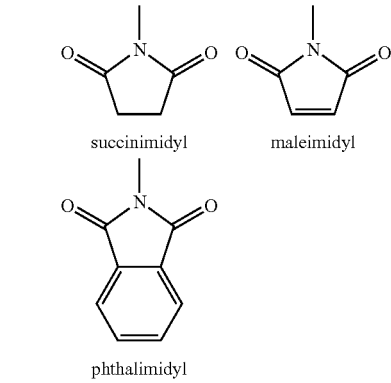

succinimidyl   maleimidyl phthalimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Ureido: —N(R¹)CONR²R³ wherein R² and R³ are independently amino substituents, as defined for amino groups, and R1 is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCONH₂, —NHCONHMe, —NHCONHEt, —NHCONMe₂, —NHCONEt₂, —NMeCONH₂, —NMeCONHMe, —NMeCONHEt, —NMeCONMe₂, and —NMeCONEt₂.

Guanidino: —NH—C(=NH)NH₂.

Tetrazolyl: a five membered aromatic ring having four nitrogen atoms and one carbon atom,

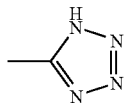

Amino: —NR¹R², wherein R¹ and R² are independently amino substituents, for example, hydrogen, a $C_{1-7}$alkyl group (also referred to as $C_{1-7}$alkylamino or di-$C_{1-17}$alkylamino), a $C_{3-20}$heterocyclyl group, or a $C_{5-20}$aryl group, preferably H or a $C_{1-7}$alkyl group, or, in the case of a "cyclic" amino group, R¹ and R², taken together with the nitrogen atom to which they are attached, form a heterocyclic ring having from 4 to 8 ring atoms. Amino groups may be primary (—NH₂), secondary (—NHR¹), or tertiary (—NHR¹R²), and in cationic form, may be quaternary (—⁺NR¹R²R³). Examples of amino groups include, but are not limited to, —NH₂, —NHCH₃, —NHC(CH₃)₂, —N(CH₃)₂, —N(CH₂CH₃)₂, and —NHPh. Examples of cyclic amino groups include, but are not limited to, aziridino, azetidino, pyrrolidino, piperidino, piperazino, morpholino, and thiomorpholino.

Amidine (amidino): —C(=NR)NR₂, wherein each R is an amidine substituent, for example, hydrogen, a $C_{1-7}$alkyl group, a $C_{3-20}$heterocyclyl group, or a $C_{5-20}$aryl group, preferably H or a $C_{1-7}$alkyl group. Examples of amidine groups include, but are not limited to, —C(=NH)NH₂, —C(=NH)NMe₂, and —C(=NMe)NMe₂.

Nitro: —NO₂.

Nitroso: —NO.

Azido: —N₃.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, preferably a $C_{1-7}$alkyl group. Examples of $C_{1-7}$alkylthio groups include, but are not limited to, —SCH₃ and —SCH₂CH₃.

Disulfide: —SS—R, wherein R is a disulfide substituent, for example, a $C_{1-7}$alkyl group, a $C_{3-20}$heterocyclyl group, or a $C_{5-20}$aryl group, preferably a $C_{1-7}$alkyl group (also referred to herein as $C_{1-7}$alkyl disulfide). Examples of $C_{1-7}$alkyl disulfide groups include, but are not limited to, —SSCH₃ and —SSCH₂CH₃.

Sulfonic acid (sulfo): —S(=O)₂OH, —SO₃H.

Sulfonate (sulfonic acid ester): —S(=O)₂OR, wherein R is a sulfonate substituent, for example, a $C_{1-7}$alkyl group, a $C_{3-20}$heterocyclyl group, or a $C_{5-20}$aryl group, preferably a $C_{1-7}$alkyl group. Examples of sulfonate groups include, but are not limited to, —S(=O)₂OCH₃ and —S(=O)₂OCH₂CH₃.

Sulfinic acid: —S(=O)OH, —SO₂H.

Sulfinate (sulfinic acid ester): —S(=O)OR; wherein R is a sulfinate substituent, for example, a $C_{1-7}$alkyl group, a $C_{3-20}$heterocyclyl group, or a $C_{5-20}$aryl group, preferably a $C_{1-7}$alkyl group. Examples of sulfinate groups include, but are not limited to, —S(=O)OCH₃ and —S(=O)OCH₂CH₃.

Sulfate: —OS(=O)₂OR; wherein R is a sulfate substituent, for example, a $C_{1-7}$alkyl group, a $C_{3-20}$heterocyclyl group, or a $C_{5-20}$aryl group, preferably a $C_{1-7}$alkyl group. Examples of sulfate groups include, but are not limited to, —OS(=O)₂OCH₃ and —SO(=O)₂OCH₂CH₃.

Sulfone (sulfonyl): —S(=O)₂R, wherein R is a sulfone substituent, for example, a $C_{1-7}$alkyl group, a $C_{3-20}$heterocyclyl group, or a $C_{5-20}$aryl group, preferably a $C_{1-7}$alkyl group, for example, a fluorinated or perfluorinated $C_{1-7}$alkyl group. Examples of sulfone groups include, but are not limited to, —S(=O)₂CH₃ (methanesulfonyl, mesyl), —S(=O)₂CF₃ (triflyl), —S(=O)₂CH₂CH₃ (esyl), —S(=O)₂C₄F₉ (nonaflyl), —S(=O)₂CH₂CF₃ (tresyl), —S(=O)₂Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfine (sulfinyl, sulfoxide): —S(=O)R, wherein R is a sulfine substituent, for example, a $C_{1-7}$alkyl group, a $C_{3-20}$heterocyclyl group, or a $C_{5-20}$aryl group, preferably a $C_{1-7}$alkyl group. Examples of sulfine groups include, but are not limited to, —S(=O)CH₃ and —S(=O)CH₂CH₃.

Sulfonyloxy: —OS(=O)₂R, wherein R is a sulfonyloxy substituent, for example, a $C_{1-7}$alkyl group, a $C_{3-20}$heterocyclyl group, or a $C_{5-20}$aryl group, preferably a $C_{1-7}$alkyl group. Examples of sulfonyloxy groups include, but are not limited to, —OS(=O)₂CH₃ (mesylate) and —OS(=O)₂CH₂CH₃ (esylate).

Sulfinyloxy: —OS(=O)R, wherein R is a sulfinyloxy substituent, for example, a $C_{1-7}$alkyl group, a $C_{3-20}$heterocyclyl group, or a $C_{5-20}$aryl group, preferably a $C_{1-7}$alkyl group. Examples of sulfinyloxy groups include, but are not limited to, —OS(=O)CH₃ and —OS(=O)CH₂CH₃.

Sulfamino: —NR¹S(=O)₂OH, wherein R¹ is an amino substituent, as defined for amino groups. Examples of sulfamino groups include, but are not limited to, —NHS(=O)₂OH and —N(CH₃)S(=O)₂OH.

Sulfonamino: —NR¹S(=O)₂R, wherein R¹ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)₂CH₃ and —N(CH₃)S(=O)₂C₆H₅.

Sulfinamino: —NR¹S(=O)R, wherein R¹ is an amino substituent, as defined for amino groups, and R is a sulfinamino substituent, for example, a $C_{1-7}$alkyl group, a $C_{3-20}$heterocyclyl group, or a $C_{5-20}$aryl group, preferably a $C_{1-7}$alkyl group. Examples of sulfinamino groups include, but are not limited to, —NHS(=O)CH₃ and —N(CH₃)S(=O)C₆H₅.

Sulfamyl: —S(=O)NR¹R², wherein R¹ and R² are independently amino substituents, as defined for amino groups. Examples of sulfamyl groups include, but are not limited to, —S(=O)NH₂, —S(=O)NH(CH₃), —S(=O)N(CH₃)₂, —S(=O)NH(CH₂CH₃), —S(=O)N(CH₂CH₃)₂, and —S(=O)NHPh.

Sulfonamido: —S(=O)₂NR¹R², wherein R¹ and R² are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Phosphino (phosphine): —PR$_2$, wherein R is a phosphino substituent, for example, —H, a C$_{1-7}$alkyl group, a C$_{3-20}$heterocyclyl group, or a C$_{5-20}$aryl group, preferably —H, a C$_{1-7}$alkyl group, or a C$_{5-20}$aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a C$_{1-7}$alkyl group, a C$_{3-20}$heterocyclyl group, or a C$_{5-20}$aryl group, preferably a C$_{1-7}$alkyl group or a C$_{5-20}$aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$alkyl group, a C$_{3-20}$heterocyclyl group, or a C$_{5-20}$aryl group, preferably —H, a C$_{1-7}$alkyl group, or a C$_{5-20}$aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$alkyl group, a C$_{3-20}$heterocyclyl group, or a C$_{5-20}$aryl group, preferably —H, a C$_{1-7}$alkyl group, or a C$_{5-20}$aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$alkyl group, a C$_{3-20}$heterocyclyl group, or a C$_{5-20}$aryl group, preferably —H, a C$_{1-7}$alkyl group, or a C$_{5-20}$aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) C$_{1-7}$alkyl group, a C$_{3-20}$heterocyclyl group, or a C$_{5-20}$aryl group, preferably —H, a C$_{1-7}$alkyl group, or a C$_{5-20}$aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) C$_{1-7}$alkyl group, a C$_{3-20}$heterocyclyl group, or a C$_{5-20}$aryl group, preferably —H, a C$_{1-7}$alkyl group, or a C$_{5-20}$aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

In many cases, substituents may themselves be substituted. For example, a C$_{1-7}$alkyl group may be substituted with, for example, hydroxy (also referred to as a C$_{1-7}$hydroxyalkyl group), C$_{1-7}$alkoxy (also referred to as a C$_{1-7}$alkoxyalkyl group), amino (also referred to as a C$_{1-7}$-aminoalkyl group), halo (also referred to as a C$_{1-7}$haloalkyl group), carboxy (also referred to as a C$_{1-7}$carboxyalkyl group), and C$_{5-20}$aryl (also referred to as a C$_{5-20}$aryl-C$_{1-7}$alkyl group).

Similarly, a C$_{5-20}$aryl group may be substituted with, for example, hydroxy (also referred to as a C$_{5-20}$hydroxyaryl group), halo (also referred to as a C$_{5-20}$haloaryl group), amino (also referred to as a C$_{5-20}$-aminoaryl group, e.g., as in aniline), C$_{1-7}$alkyl (also referred to as a C$_{1-7}$alkyl-C$_{5-20}$aryl group, e.g., as in toluene), and C$_{1-7}$alkoxy (also referred to as a C$_{1-7}$alkoxy-C$_{5-20}$aryl group, e.g., as in anisole).

These and other specific examples of such substituted-substituents are described below.

C$_{1-7}$haloalkyl group: The term "C$_{1-7}$haloalkyl group," as used herein, pertains to a C$_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a C$_{1-7}$ perhaloalkyl group." Examples of C$_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

C$_{1-7}$haloalkoxy: —OR, wherein R is a C$_{1-7}$haloalkyl group. Examples of C$_{1-7}$haloalkoxy groups include, but are not limited to, —OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$.

C$_{1-7}$hydroxyalkyl: The term "C$_{1-7}$hydroxyalkyl group," as used herein, pertains to a C$_{1-7}$alkyl group in which at least one hydrogen atom has been replaced with a hydroxy group. Examples of C$_{1-7}$hydroxyalkyl groups include, but are not limited to, —CH$_2$OH, —CH$_2$CH$_2$OH, and —CH(OH)CH$_2$OH.

C$_{1-7}$carboxyalkyl: The term "C$_{1-7}$carboxyalkyl group," as used herein, pertains to a C$_{1-7}$alkyl group in which at least one hydrogen atom has been replaced with a carboxy group. Examples of C$_{1-7}$carboxyalkyl groups include, but are not limited to, —CH$_2$COOH and —CH$_2$CH$_2$COOH.

C$_{1-7}$aminoalkyl: The term "C$_{1-7}$aminoalkyl group," as used herein, pertains to a C$_{1-7}$alkyl group in which at least one hydrogen atom has been replaced with an amino group. Examples of C$_{1-7}$aminoalkyl groups include, but are not limited to, —CH$_2$NH$_2$, —CH$_2$CH$_2$NH$_2$, and —CH$_2$CH$_2$N(CH$_3$)$_2$.

C$_{1-7}$aminoalkylamino: The term "C$_{1-7}$aminoalkylamino," as used herein, pertains to an amino group, —NR$^1$R$^2$, in which one of the substituents, R$^1$ or R$^2$, is itself a C$_{1-7}$aminoalkyl group (—C$_{1-7}$alkyl-NR$^1$R$^2$). The C$_{1-7}$aminoalkylamino may be represented, for example, by the formula —NR$^1$—C$_{1-7}$alkyl-NR$^1$R$^2$. Examples of amino-C$_{1-7}$alkylamino groups include, but are not limited to, groups of the formula —NR$^1$(CH$_2$)$_n$NR$^1$R$^2$, where n is 1 to 6, for example, —NHCH$_2$NH$_2$, —NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), and —NH(CH$_2$)$_6$NH(Et).

C$_{3-7}$cycloalkyl-C$_{1-7}$alkyl: The term "," as used herein, describes certain C$_{1-7}$alkyl groups which have been substituted with a C$_{3-7}$cycloalkyl group. Examples of such groups include, but are not limited to, cyclopropylmethyl, cyclobutylmethyl, cyclopentylmethyl, and cyclohexylmethyl.

C$_{3-7}$cycloalkenyl-C$_{1-7}$alkyl: The term "," as used herein, describes certain C$_{1-7}$alkyl groups which have been substituted with a C$_{3-7}$cycloalkenyl group. Examples of such groups include, but are not limited to, cyclopropenylmethyl and cyclohexenylmethyl.

C$_{1-7}$alkyl-C$_{5-20}$aryl: The term "C$_{1-7}$alkyl-C$_{5-20}$aryl," as used herein, describes certain C$_{5-20}$aryl groups which have been substituted with a C$_{1-7}$alkyl group. Examples of such groups include, but are not limited to, tolyl (as in toluene), xylyl (as in xylene), mesityl (as in mesitylene), styryl (as in styrene), and cumenyl (as in cumene).

$C_{1-7}$alkyl-$C_{5-20}$aryloxy: The term "$C_{1-7}$alkyl-$C_{5-20}$aryloxy," as used herein, describes certain $C_{5-20}$aryloxy groups which have been substituted with a $C_{1-7}$alkyl group. Examples of such groups include, but are not limited to, tolyloxy, xylyloxy, mesityloxy, and cumenyloxy.

$C_{5-20}$aryl-$C_{1-7}$alkyl: The term "$C_{5-20}$aryl-$C_{1-7}$alkyl," as used herein, describers certain $C_{1-7}$alkyl groups which have been substituted with a $C_{5-20}$aryl group. Examples of such groups include, but are not limited to, benzyl (phenylmethyl), tolylmethyl, phenylethyl, triphenylmethyl (trityl), and cinnamyl (3-phenyl-2-propenyl, $C_6H_5$—CH=CH—$CH_2$—).

$C_{5-20}$aryl-$C_{1-7}$alkoxy: The term "$C_{5-20}$aryl-$C_{1-7}$alkoxy," as used herein, describes certain $C_{1-7}$alkoxy groups which have been substituted with a $C_{5-20}$aryl group. Examples of such groups include, but are not limited to, benzyloxy, tolylmethoxy, and phenylethoxy.

$C_{5-20}$haloaryl: The term "$C_{5-20}$haloaryl," as used herein, describes certain $C_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

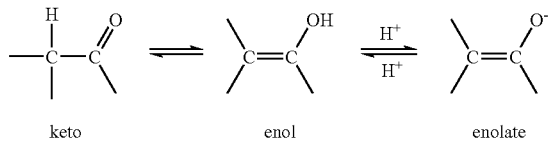

keto      enol      enolate

Note that specifically included in the term "isomer" are compounds with one or more isotopic substitutions. For example, H may be in any isotopic form, including ¹H, ²H (D), and ³H (T); C may be in any isotopic form, including ¹²C, ¹³C, and ¹⁴C; O may be in any isotopic form, including ¹⁶O and ¹⁸O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al⁺³. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
C$_{1-7}$alkyl
(e.g., -Me, -Et, -nPr, -iPr, -nBu, -sBu, -iBu, -tBu);
C$_{1-7}$aminoalkyl
(e.g., aminoethyl; 2-(N,N-diethylamino)ethyl; 2-(4-morpholino)ethyl); and
acyloxy-C$_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy) carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et₂O), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

Chemical Synthesis

Compounds suitable for use in the present invention may be synthesised using known methods. Suitable reagents and intermediates are commercially available. Additionally, several methods for the chemical synthesis of suitable compounds for use in present invention are described herein. These methods may be modified and/or adapted in known ways in order to facilitate the synthesis of additional compounds suitable for use in the present invention.

Examples of some suitable methods for the synthesis of the compounds of the present invention are described below.

In one approach, an appropriate aromatic ring is sulfonylated using chlorosulfonic acid, to give the sulfonic acid. The acid is then reacted with thionyl chloride to give the aryl sulfonyl chloride. Finally the sulfonyl chloride can be coupled with an amine to give the desired sulfonamide. An example of such a method is shown in the following scheme.

Scheme 1

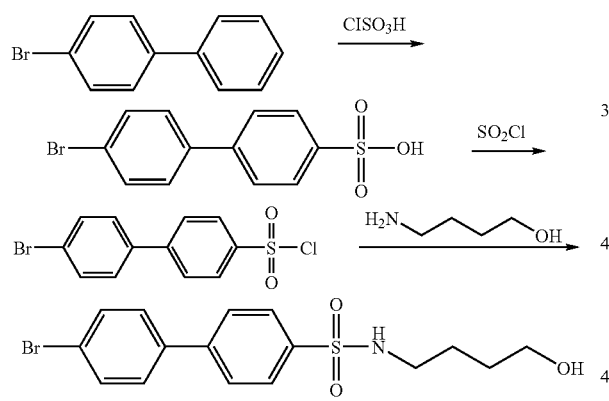

In another approach, the biphenyl can be prepared following the formation of the sulfonamide by a Suzuki-type coupling using the desired boronic acid and bromide, as described by Ha-Duong et al, 2001. An example of such a method is shown in the following scheme.

Scheme 2

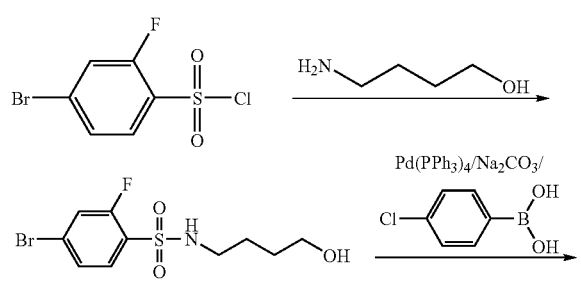

-continued

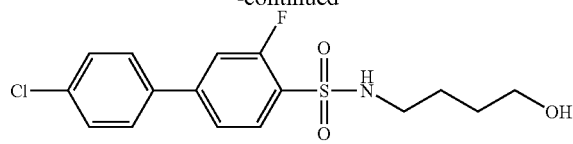

In another approach, the Suzuki coupling procedure may be used to prepare other sulfonamides including the 2-sulfonylamino and 3-sulfonylamino derivatives. An example of such a method is shown in the following scheme.

Scheme 3

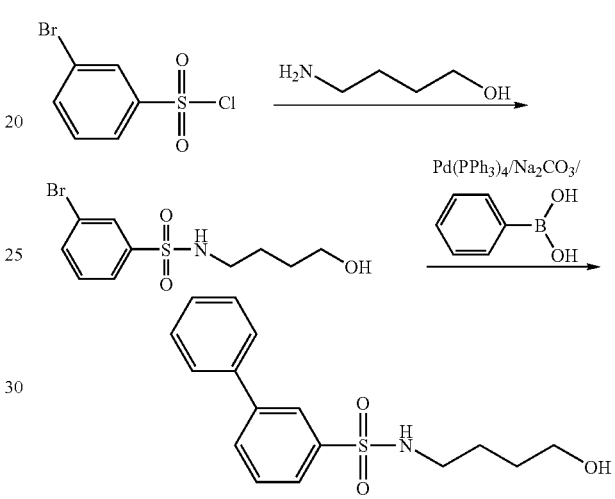

In another approach, the nitrogen atom of the sulfonamide may be further reacted, e.g., with an alkylating agent. An example of such a method is shown in the following scheme.

Scheme 4

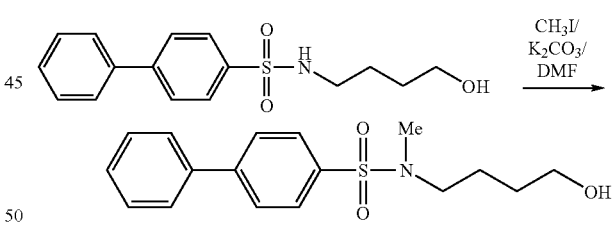

In another approach, a second alcohol group can be introduced by further reaction with a halo-alkene. The alkene is then converted to an alcohol by hydroboration. An example of such a method is shown in the following scheme.

Scheme 5

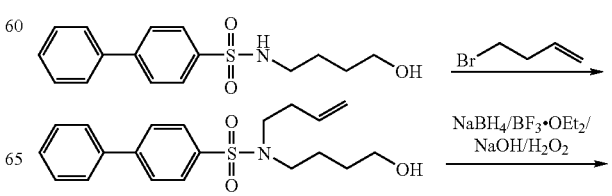

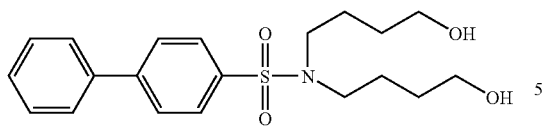

In another approach, the alcohol group can be further reacted, e.g., with an acylating agent. An example of such a method is shown in the following scheme.

Scheme 6

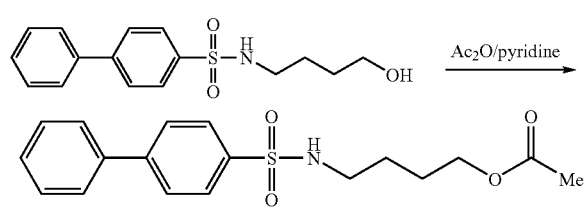

In another approach, where certain electron-donating aryl substituents are present, it may be necessary to add a deactivating group in order to allow addition of the sulfonyl group at the desired position. Such substituents include, for example, hydroxy and amino groups. An example of such a method is shown in the following scheme.

Scheme 7

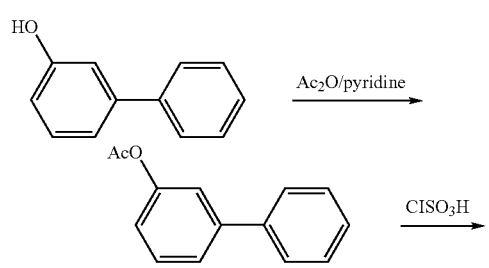

In another approach, the deactivating group can be retained or removed. An example of such a method (removal) is shown in the following scheme.

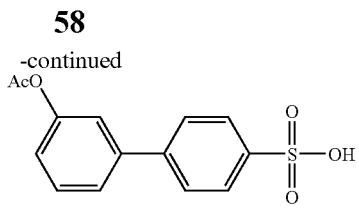

Scheme 8

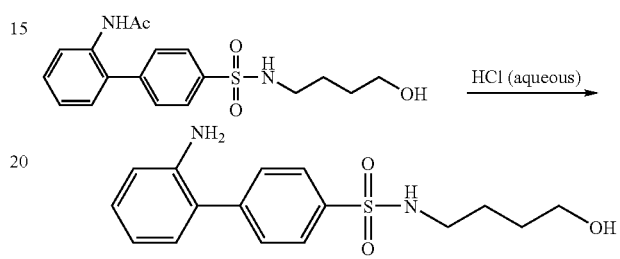

In another approach, derivatives with a terminal amino group may also be prepared by reaction with a suitable diamine. An example of such a method is shown in the following scheme.

Scheme 9

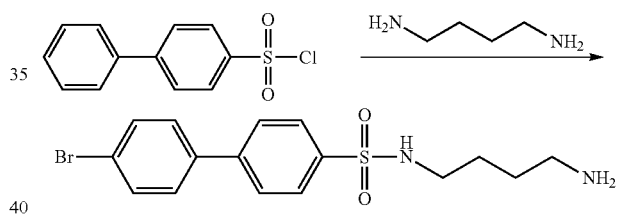

In another approach, a terminal amine is further derivatized. An example of such a method is shown in the following scheme.

Scheme 10

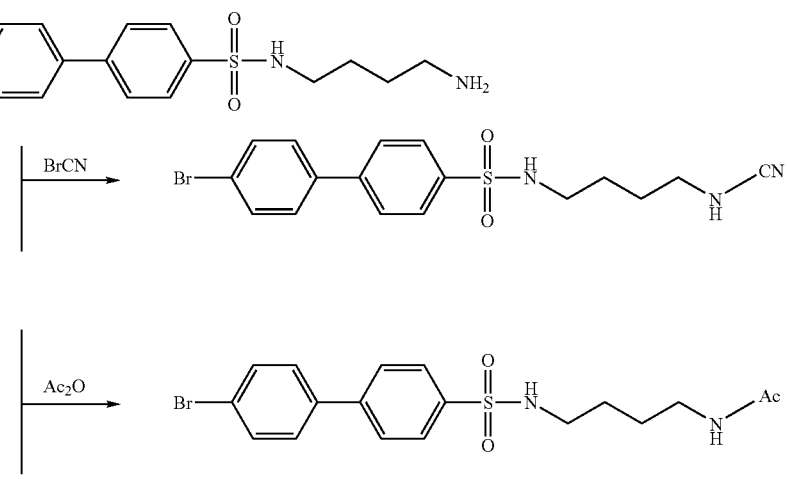

-continued

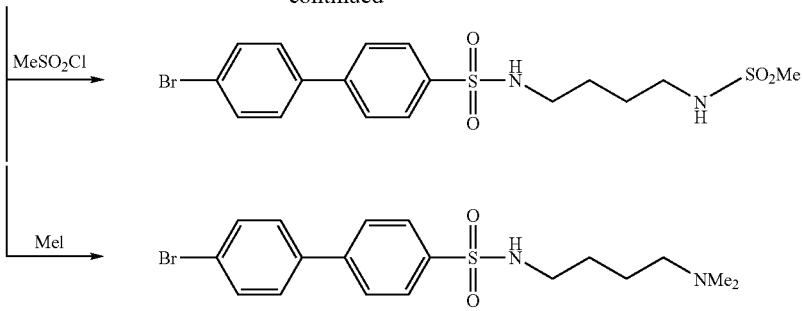

In another example, derivatives with a terminal carboxylic acid group may also be prepared by similar methodology. These may be further reacted with an alkylating agent to give an ester. An example of such a method is shown in the following scheme.

Scheme 11

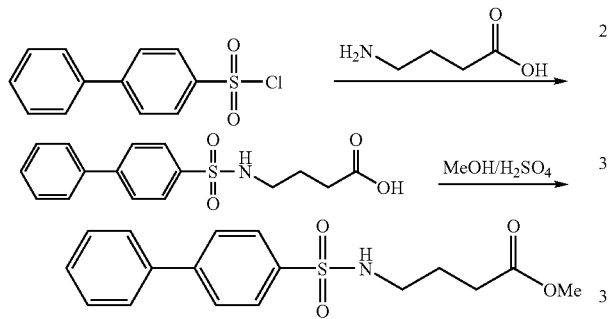

The products may be purified, for example, by column chromatography, trituration with ether, or by crystallisation.

Uses

The present invention provides active compounds, specifically, certain active aryl alkyl sulfonamides and derivatives thereof, as described herein, which, e.g., inhibit osteoclasts, for example, inhibit of the survival, formation, and/or activity of osteoclasts, and/or which inhibit bone resorption. The compounds may therefore be referred to as "osteoclast inhibitors" and/or "bone resorption inhibitors" and are useful in the treatment of bone conditions, bone disorders, conditions mediated by osteoclasts, conditions characterised by bone resorption, etc., as described herein.

The term "active," as used herein, pertains to compounds which are capable of, e.g., inhibiting the survival, formation, and/or activity of osteoclasts, and/or inhibiting bone resorption, and specifically includes both compounds with intrinsic activity (drugs) as well as prodrugs of such compounds, which prodrugs may themselves exhibit little or no intrinsic activity.

One of ordinary skill in the art is readily able to determine whether or not a candidate compound inhibits the survival, formation, and/or activity of osteoclasts and/or inhibits bone resorption. For example, suitable methods which may conveniently be used in order to assess the inhibitory effects offered by a particular compound are described in the examples below.

Use in Methods of Inhibition

One aspect of the invention pertains to a method of inhibiting osteoclast survival, formation, and/or activity, in vitro or in vivo, comprising contacting an osteoclast with an effective amount of an active compound, as described herein.

Another aspect of the invention pertains to a method of inhibiting bone resorption, in vitro or in vivo, comprising contacting cells in the bone microenvironment with a therapeutically-effective amount of an active compound, as described herein.

The term "cells in the bone microenvironment," as used herein, pertains to cells such as osteoblasts, osteoclasts, osteocytes and bone marrow stromal cells, which are located in close proximity to bone (e.g., within one hundred micrometers of the bone surface).

Bone Disorders

The compounds of the present invention are also useful in the treatment of bone disorders, for example, conditions mediated by osteoclasts (as "osteoclast inhibitors"), and/or conditions characterised by bone resorption (as "bone resorption inhibitors").

Examples of such conditions include, but are not limited to, the following diseases of the skeleton, including but not limited to, pathologically low bone mineral density, such as:
osteoporosis (including, e.g., steroid induced osteoporosis);
osteopetrosis;
osteoarthritis;
ectopic bone formation;
Paget's disease of bone (osteitis deformans);
rheumatoid arthritis;
hypercalcaemia caused by conditions associated with increased bone resorption, including, but not limited to: vitamin D intoxication, primary or tertiary hyperparathyroidism, immobilisation, and sarcoidosis;
neoplasia of bones, both as a primary tumour and as metastases, including but not limited to, osteosarcoma and osteoma (Zheng et al., 1998, *J. Cell Biochem.*, Vol. 70, p. 121) and cancer associated bone disease (e.g., hypercalcaemia of malignancy, bone metastases, osteolytic bone metastases, multiple myeloma, breast carcinoma);
aseptic loosening of prosthetic implants (e.g., artificial joints, e.g., knees, hips, etc., can loosen due to osteoclast activity driven by local inflammation) (see, e.g., Childs, L. M., et al., 2001, *Journal of Bone and Mineral Research*, Vol. 16, No. 2, pp. 338-347).

In one embodiment, the bone disorder is osteoporosis, rheumatoid arthritis, cancer associated bone disease, or Paget's disease.

In one embodiment, the bone disorder is osteoporosis (e.g., osteoporosis not associated with inflammation; e.g., osteoporosis associated with a genetic predisposition, sex hormone deficiency, or ageing), cancer associated bone disease, and Paget's disease of bone.

In one embodiment, the bone disorder is osteoporosis (e.g., osteoporosis not associated with inflammation and/or osteoporosis associated with a genetic predisposition, sex hormone deficiency, or ageing).

Inflammation/Immune Disorders

The compounds of the present invention have also macrophage inhibitory effects, and so are useful in the treatment of conditions associated with inflammation or activation of the immune system.

Examples of such conditions include, but are not limited to, the following

Diseases with an inflammatory or autoimmune component, including allergic diseases, such as atopy, allergic rhinitis, atopic dermatitis, anaphylaxis, allergic bronchopulmonary aspergillosis, and hypersensitivity pneumonitis (pigeon breeders disease, farmer's lung disease, humidifier lung disease, malt workers' lung disease); allergies, including flea allergy dermatitis in mammals such as domestic animals, e.g., dogs and cats, contact allergens including mosquito bites or other insect sting allergies, poison ivy, poison oak, poison sumac, or other skin allergens; autoimmune disorders, including, but not limited to, type I diabetes, Crohn's disease, multiple sclerosis, arthritis, rheumatoid arthritis (Ogata et at., 1997, *J. Pathol.*, Vol. 182, p. 106); Gong et al., 1997, *J. Exp. Med.*, Vol 186, p. 131), systemic lupus erythematosus, autoimmune (Hasimoto's) thyroiditis, autoimmune liver diseases such as hepatitis and primary biliary cirrhosis, hyperthyroidism (Graves' disease; thyrotoxicosis), insulin-resistant diabetes, autoimmune adrenal insufficiency (Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, experimental allergic encephalomyelitis, autoimmune polyneuritis, pemphigus and other bullous diseases, rheumatic carditis, Goodpasture's syndrome, postcardiotomy syndrome, Sjogren's syndrome, polymyositis, dermatomyositis, and scleroderma; disease states resulting from inappropriate inflammation, either local or systemic, for example, irritable or inflammatory bowel syndrome (Mazzucchelli et al., 1996, *J. Pathol.*, Vol. 178, p. 201), skin diseases such as psoriasis and lichen planus, delayed type hypersensitivity, chronic pulmonary inflammation, e.g., pulmonary alveolitis and pulmonary granuloma, gingival inflammation or other periodontal disease, and osseous inflammation associated with lesions of endodontic origin (Volejnikova et al., 1997, *Am. J. Pathol.*, Vol. 150, p. 1711), hypersensitivity lung diseases such as hypersensitivity pneumonitis (Sugiyama et al., 1995, *Eur. Respir. J.*, Vol. 8, p. 1084), and inflammation related to histamine release from basophils (Dvorak et al., 1996, *J. Allergy Clin. Immunol.*, Vol. 98, p. 355), such as hay fever, histamine release from mast cells (Galli et al., 1989, *Ciba Foundation Symposium*, Vol. 147, p. 53), or mast cell tumors, types of type 1 hypersensitivity reactions (anaphylaxis, skin allergy, hives, allergic rhinitis, and allergic gastroenteritis); ulcerative colitis.

Use in Methods of Therapy

Another aspect of the present invention pertains to an active compound as described herein for use in a method of treatment of the human or animal body by therapy.

In one embodiment, the treatment is treatment of a bone disorder, for example, a condition mediated by osteoclasts and/or characterised by bone resorption, as described herein.

In one embodiment, the treatment is treatment of a condition mediated by osteoclasts, as described herein.

In one embodiment, the treatment is treatment of a condition characterised by bone resorption, as described herein.

In one embodiment, the treatment is treatment of osteoporosis, rheumatoid arthritis, cancer associated bone disease, or Paget's disease.

In one embodiment, the treatment is treatment of a condition associated with inflammation or activation of the immune system, as described herein.

Use in the Manufacture of Medicaments

Another aspect of the present invention pertains to use of an active compound, as described herein, in the manufacture of a medicament for use in treatment.

In one embodiment, the treatment is treatment of a bone disorder, for example, a condition mediated by osteoclasts and/or characterised by bone resorption, as described herein.

In one embodiment, the treatment is treatment of a condition mediated by osteoclasts, as described herein.

In one embodiment, the treatment is treatment of a condition characterised by bone resorption, as described herein.

In one embodiment, the treatment is treatment of osteoporosis, rheumatoid arthritis, cancer associated bone disease, or Paget's disease.

In one embodiment, the treatment is treatment of a condition associated with inflammation or activation of the immune system, as described herein.

Methods of Treatment

Another aspect of the present invention pertains to a method of treatment comprising administering to a patient in need of treatment a therapeutically effective amount of an active compound as described herein, preferably in the form of a pharmaceutical composition.

In one embodiment, the treatment is treatment of a bone disorder, for example, a condition mediated by osteoclasts and/or characterised by bone resorption, as described herein.

In one embodiment, the treatment is treatment of a condition mediated by osteoclasts, as described herein.

In one embodiment, the treatment is treatment of a condition characterised by bone resorption, as described herein.

In one embodiment, the treatment is treatment of osteoporosis, rheumatoid arthritis, cancer associated bone disease, or Paget's disease.

In one embodiment, the treatment is treatment of a condition associated with inflammation or activation of the immune system, as described herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included. For example, use with perimenopausal women who may not yet have osteoporosis, but who are at risk of osteoporosis, is encompassed by the term "treatment."

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Other Uses

Active compounds may also be used as cell culture additives to inhibit osteoclasts, for example, to inhibit the survival, formation, and/or activity of osteoclasts.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other osteoclast inhibitors, etc.

Kits

One aspect of the invention pertains to a kit comprising (a) an active compound as described herein, or a composition comprising an active compound as described herein, e.g., preferably provided in a suitable container and/or with suitable packaging; and (b) instructions for use, e.g., written instructions on how to administer the active compound or composition.

The written instructions may also include a list of indications for which the active ingredient is a suitable treatment.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject/patient may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a fetus.

In one preferred embodiment, the subject/patient is a human.

Formulations

While it is possible for the active compound to be administered alone, it is preferable to present it as a pharmaceutical formulation (e.g., composition, preparation, medicament) comprising at least one active compound, as defined above, together with one or more other pharmaceutically acceptable ingredients well known to those skilled in the art, including, but not limited to, pharmaceutically acceptable carriers, diluents, excipients, adjuvants, fillers, buffers, preservatives, antioxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active compound is dissolved or suspended in a suitable carrier, especially an aqueous solvent for the active compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the active compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 μg to about 250 mg (more typically about 100 μg to about 25 mg) per kilogram body weight of the subject per day. Where the active compound is a salt, an ester, an amide, a prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

Example 1

Biphenyl-4-sulfonic acid-(4-hydroxybutyl)-amide (ABD-155)

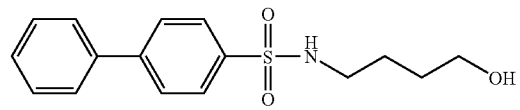

Biphenyl sulfonyl chloride (1 g) and 4-aminobutanol (1 g) were dissolved in dichloromethane containing pyridine (1 mL). The mixture was stirred for 2 hours at room temperature. After washing with water the solvent was evaporated and the title compound obtained as a white solid following trituration with ether. $\delta_C$ (DMSO, 62.9 MHz): 25.9, 29.6, 42.6, 60.2, 127.1, 127.2, 127.6, 128.6, 129.2, 138.6, 139.4 and 143.8. $\delta_H$ (DMSO, 250 MHz): 1.40 (4H, m), 2.75 (2H, m), 3.36 (3H, m), 4.20 (1H, s), 7.43-7.54 (3H, m), 7.75 (2H, d, J 7.0) and 7.88 (4H, m).

Example 2

Biphenyl-4-sulfonic acid-(5-hydroxypentyl)-amide (ABD-180)

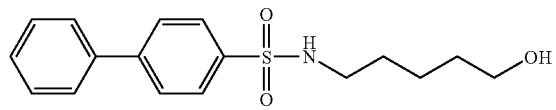

Using a method analogous to that described in Example 1, with biphenyl sulfonyl chloride and 5-aminopentanol, the title compound was obtained as a white powder. $\delta_C$ (DMSO, 62.9 MHz): 22.6, 28.9, 32.0, 42.6, 60.5, 127.1, 127.2, 127.6, 128.6, 129.2, 138.6, 139.3 and 143.8.

Example 3

Biphenyl-4-sulfonic acid-(3-hydroxypropyl)-amide (ABD-203)

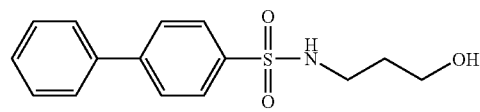

Using a method analogous to that described in Example 1, with biphenyl sulfonyl chloride and 3-aminopropanol, the title compound was obtained as a white powder. $\delta_C$ (DMSO, 62.9 MHz): 32.4, 40.0, 58.1, 127.1, 127.2, 127.6, 128.6, 129.2, 138.6, 139.3 and 143.8.

Example 4

Biphenyl-4-sulfonic acid-(4-hydroxybutyl)-methyl-amide (ABD-156)

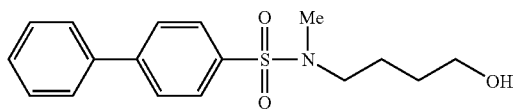

The title compound was prepared from biphenyl-4-sulfonic acid-(4-hydroxybutyl)-amide (0.4 g), methyl iodide (0.2 mL) and $K_2CO_2$ (0.5 g) in dimethylformamide (20 mL). The mixture was stirred at room temperature for 4 hours, poured into water and extracted with diethyl ether. The organic phase was repeatedly washed with water and evaporated to give the title compound as a white solid (80%). $\delta_C$ (DMSO, 62.9 MHz): 23.7, 29.5, 34.5, 49.6, 60.2, 127.1, 127.2, 127.6, 128.6, 129.2, 135.8, 138.4 and 144.3. $\delta_H$ (DMSO, 250 MHz): 1.45 (4H, m), 2.68 (3H, s), 2.97 (2H, t, J 7.0), 3.40 (2H, m), 7.49 (3H, m), 7.75 (2H, d, J 7.0), 7.83 (2H, d, J 8.5) and 7.91 (2H, d, J 8.2).

Example 5

Biphenyl-4-sulfonic acid-(5-hydroxypentyl)-methyl-amide (ABD-186)

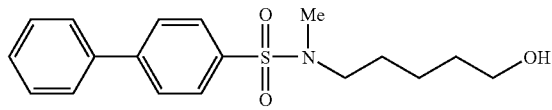

Using a method analogous to that described in Example 4, with biphenyl-4-sulfonic acid-(5-hydroxypentyl)-amide and methyl iodide, the title compound was obtained. $\delta_C$ (CDCl$_3$, 62.9 MHz): 22.7, 27.4, 32.2, 34.7, 50.0, 62.7, 127.4, 127.9, 128.5, 129.1, 136.0, 139.3 and 145.4.

Example 6

Biphenyl-4-sulfonic acid-(4-hydroxybutyl)-pentyl-amide (ABD-164)

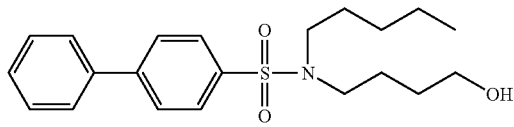

Using a method analogous to that described in Example 4, with biphenyl-4-sulfonic acid-(4-hydroxybutyl)-amide and bromopentane, reacted at 60° C. for 3 hours, the title compound was obtained as an amorphous white solid. $\delta_C$ (CDCl$_3$, 62.9 MHz): 14.0, 22.3, 25.3, 28.4, 29.6, 48.1, 48.4, 62.2, 127.3, 127.6, 128.4, 129.0, 138.5, 139.4 and 145.2. $\delta_H$ (CDCl$_3$, 250 MHz): 0.84 (3H, t, J 7.0), 1.24 (4H, m), 1.50 (6H, m), 2.06 (1H, s), 3.14 (4H, m), 3.62 (2H, t, J 5.95), 7.41 (3H, m), 7.56 (2H, d, J 7.94), 7.67 (2H, d, J 8.55) and 7.83 (2H, d, J 8.24).

Example 7

Biphenyl-4-sulfonic acid-(5-hydroxypentyl)-pentyl-amide (ABD-185)

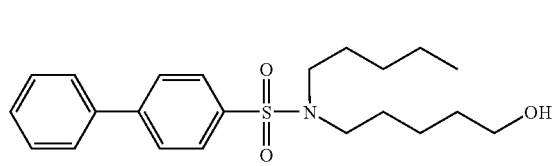

Using a method analogous to that described in Example 4, with biphenyl-4-sulfonic acid-(5-hydroxypentyl)-amide and bromopentane, reacted at 60° C. for 3 hours, the title compound was obtained as an amorphous white solid. $\delta_C$ (CDCl$_3$, 62.9 MHz): 14.0, 22.3, 22.9, 28.4, 28.6, 28.9, 32.2, 48.2, 48.4, 62.7, 127.3, 127.6, 128.4, 129.1, 138.6, 139.4 and 145.2.

Example 8

Biphenyl-4-sulfonic acid-(4-hydroxybutyl)-penten-1-yl-amide (ABD-176)

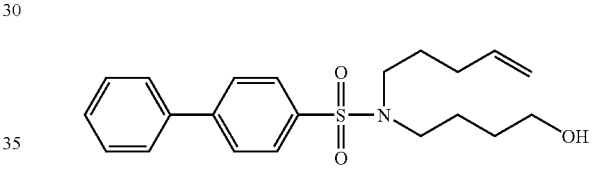

Using a method analogous to that described in Example 4, with biphenyl-4-sulfonic acid-(4-hydroxybutyl)-amide and 5-bromopentene, reacted at 60° C. for 3 hours, the title compound was obtained as a white powder. $\delta_C$ (CDCl$_3$, 62.9 MHz): 25.4, 28.0, 29.6, 30.9, 48.0, 48.3, 62.4, 115.4, 127.3, 127.7, 128.5, 129.1, 137.5, 138.4, 139.4 and 145.3. $\delta_H$ (CDCl$_3$, 250 MHz): 1.56-1.67 (8H, m), 2.03 (2H, m), 3.16 (4H, m), 3.65 (2H, t, J 7.1), 4.94 (2H, m), 5.74 (1H, m), 7.43 (3H, m), 7.59 (2H, d, J 7.0), 7.69 (2H, d, J 8.2) and 7.84 (2H, d, J 8.2).

Example 9

Biphenyl-4-sulfonic acid-(4-hydroxybutyl)-buten-1-yl-amide (ABD-179)

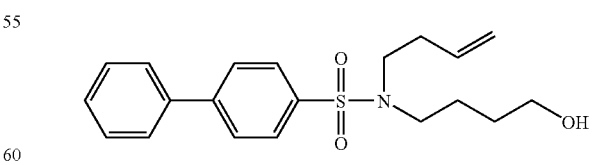

Using a method analogous to that described in Example 4, with biphenyl-4-sulfonic acid-(4-hydroxybutyl)-amide and 4-bromobutene, reacted at 60° C. for 3 hours, the title compound was obtained as a white powder. $\delta_C$ (CDCl$_3$, 62.9 MHz): 25.2, 29.6, 33.4, 47.8, 48.3, 62.4, 117.2, 127.3, 127.6, 127.7, 128.5, 129.1, 134.6, 138.4, 139.3 and 145.3. $\delta_H$ (CDCl$_3$, 250 MHz): 1.58 (4H, m), 2.34 (3H, m), 3.21 (4H, m), 3.66 (2H, t, J 6.1), 5.04 (2H, m), 5.69 (1H, m), 7.46 (3H, m), 7.60 (2H, d, J 7.3), 7.70 (2H, d, J 8.2) and 7.86 (2H, d, J 8.2)

Example 10

Biphenyl-4-sulfonic acid-(4-hydroxybutyl)-(5-hydroxypentyl)-amide (ABD-178)

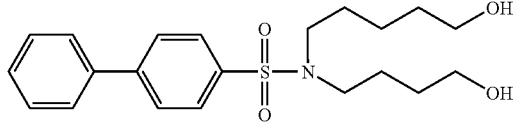

Biphenyl-4-sulfonic acid-(4-hydroxybutyl)-penten-1-yl-amide (1 g) was dissolved in 0.5 M NaBH$_4$ in diglyme (9 mL) and chilled in an ice bath. BF$_3$.OEt$_2$ (1 mL) in diglyme (4 mL) was added with vigorous stirring. Stirring was continued for 1 hour and water (1 mL) was added. 3M NaOH (2 mL) was added followed by 30% H$_2$O$_2$ (3 mL). Anhydrous K$_2$CO$_3$ (5 g) was added and the solvent decanted. The K$_2$CO$_3$ was washed with ethyl acetate and the combined organics dried (Na$_2$SO$_4$) and evaporated. Distillation under vacuum removed most of the remaining diglyme. The residue was purified by column chromatography (ethyl acetate/petrol) to give the title compound as a white powder. $\delta_C$ (DMSO, 62.9 MHz): 22.7, 25.2, 28.3, 29.6, 32.1, 48.0, 60.3, 60.5, 127.1, 127.2, 127.6, 128.6, 129.2, 138.1, 138.4 and 144.1.

Example 11

Biphenyl-4-sulfonic acid-(4-hydroxybutyl)-(4-hydroxybutyl)-amide (ABD-187)

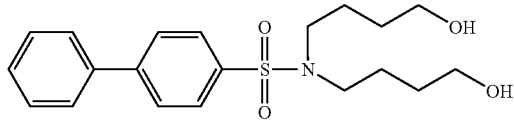

Using a method analogous to that described in Example 10, with biphenyl-4-sulfonic acid-(4-hydroxybutyl)-buten-1-yl-amide, the title compound was obtained as a white powder. $\delta_C$ (DMSO, 62.9 MHz): 25.2, 29.6, 48.1, 60.3, 127.1, 127.2, 127.6, 128.6, 129.2, 138.1, 138.4 and 144.1.

Example 12

Biphenyl-4-sulfonic acid [2-(tert-butyl-diphenyl-silanyloxy)-ethyl]-(4-hydroxy-butyl)-amide (ABD-188)

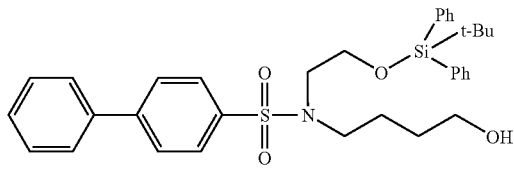

Biphenyl-4-sulfonic acid-(4-hydroxybutyl)-amide (1 g) and tert-butyl-(2-iodo-ethoxy) diphenyl silane (2 g) were heated in DMF (30 mL) for 3 hours at 60° C. The resultant mixture was poured into water and extracted with dichloromethane. Evaporation and column chromatography (petrol/ethyl acetate) gave the title compound as an amorphous solid. $\delta_C$ (CDCl$_3$, 62.9 MHz): 19.2, 25.1, 26.8, 29.5, 49.3, 49.8, 62.4, 62.9, 127.3, 127.6, 127.7, 127.8, 128.5, 129.1, 129.9, 133.2, 135.6, 138.4, 139.4 and 145.3.

Example 13

Biphenyl-4-sulfonic acid-(4-hydroxybutyl)-(2-hydroxyethyl)-amide (ABD-189)

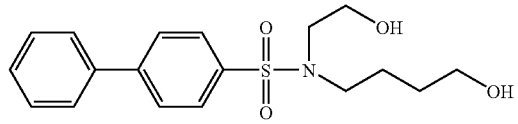

Biphenyl-4-sulfonic acid [2-(tert-butyl-diphenyl-silanyloxy)-ethyl]-(4-hydroxy-butyl)-amide (1 g) was dissolved in tertiarybutylammonium fluoride (15 mL of 1 M in tetrahydrafuran) and stirring for 30 minutes. The solvent was evaporated and the residue dissolved in methylene chloride, washed with water and dried over Na$_2$SO$_4$. The product was purified by column chromatography (ethyl acetate: light petroleum) to give the title compound. $\delta_C$ (DMSO, 62.9 MHz): 25.1, 29.5, 48.9, 51.2, 57.9, 60.3, 127.1, 127.2, 127.6, 128.6, 129.2, 138.1, 138.4 and 144.1.

Example 14

Acetic acid 4-(biphenyl-4-sulfonylamino)-butyl ester (ABD-192)

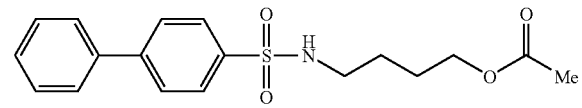

Biphenyl-4-sulfonic acid-(4-hydroxybutyl)-amide (1 g) was dissolved in acetic anhydride (25 mL). Pyridine (5 mL) was added and the mixture stirred for 3 hours at 50° C. The mixture was poured into water (200 mL), extracted with ethyl acetate (100 mL), dried (Na$_2$SO$_4$) and evaporated to give the title compound as an amorphous solid. $\delta_C$ (CDCl$_3$, 62.9 MHz): 21.0, 25.7, 26.3, 42.8, 63.8, 127.3, 127.6, 127.8, 128.0, 129.1, 138.4, 139.3, 145.6 and 171.2.

Example 15

4'-Bromo-biphenyl sulfonic acid

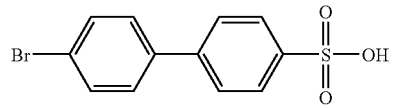

4'-Bromobiphenyl (14 g) was dissolved in chloroform (140 mL) at room temperature. Chlorosulfonic acid (8.4 g) was added dropwise and a precipitate appeared soon after addition was complete. Stirring was continued for a further 4 hours, after which the solid was collected by filtration. Further crops of crystals were collected from the filtrate. The solid was washed with cold chloroform and the washings also allowed to crystallise, to give the title compound.

Example 16

4'-Bromo-biphenyl sulfonyl chloride

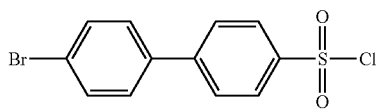

4'-Bromo-biphenyl sulfonic acid (5 g) was refluxed in thionyl chloride (30 mL) with a catalytic quantity of DMF (0.5 mL) for 4 hours. Toluene was added and the solvents evaporated under vacuum. The residue collected was recrystallised from petrol/ethyl acetate to give the title compound as large colourless crystals.

Example 17

4-Bromobiphenyl-4-sulfonic acid-(5-hydroxypentyl)-amide (ABD-199)

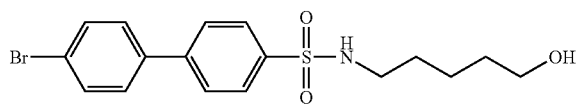

4'-Bromobiphenyl sulfonyl chloride (1 g) and 5-aminopentanol (1 g) were dissolved in dichloromethane (30 mL) containing pyridine (1 mL). The mixture was stirred overnight at room temperature. After washing with water the solvent was evaporated and the title compound obtained as a white crystalline solid following trituration with ether. $\delta_C$ DMSO, 62.9 MHz): 22.6, 28.9, 32.0, 42.6, 60.5, 122.1, 127.2, 127.3, 129.2, 132.0, 137.8, 139.7 and 142.5.

Example 18

4'-Fluorobiphenyl sulfonic acid

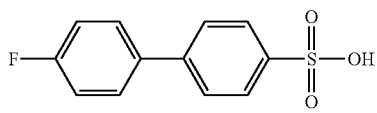

4'-Fluorobiphenyl (5 g) was dissolved in chloroform (100 mL) at room temperature. Chlorosulfonic acid (5 g) was added dropwise and stirring was continued for a further 4 hours, after which the solvent was allowed to slowly evaporate until precipitation was seen. The mixture was left to recrystallised overnight and the solid was collected by filtration. Further crops of crystals were collected from the filtrate.

Example 19

4'-Fluorobiphenyl sulfonyl chloride

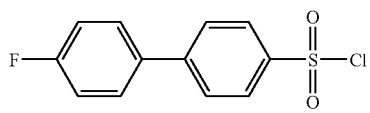

4'-Fluorobiphenyl sulfonic acid (3 g) was refluxed in thionyl chloride (30 mL) with a catalytic quantity of DMF (0.5 mL) for 4 hours. Toluene was added and the solvents evaporated under vacuum to give the title compound as an amorphous solid.

Example 20

4'-Fluorobiphenyl-4-sulfonic acid-(4-hydroxybutyl)-amide (ABD-200)

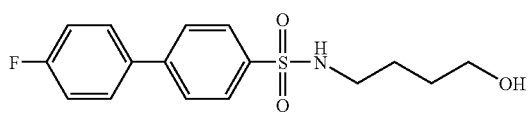

4'-Fluorobiphenyl sulfonyl chloride (1 g) and 4-aminobutanol (1 g) were dissolved in dichloromethane (30 mL) containing pyridine (1 mL). The mixture was stirred overnight at room temperature. After washing with water the solvent was evaporated and the title compound obtained as a white solid following trituration with ether. $\delta_C$ (DMSO, 62.9 MHz): 25.9, 29.6, 42.6, 60.2, 115.9 (d, J22.5), 127.1, 128.9 (d, J8.8), 129.1, 135.0 (d, J 2.9), 139.3, 142.7 and 162.5 (d, J245.1).

Example 21

4'-Bromobiphenyl-4-sulfonic acid-(4-hydroxybutyl)-amide (ABD-201)

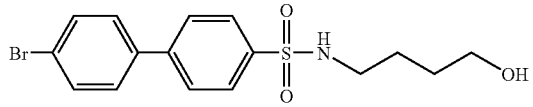

4'-Bromobiphenyl sulfonyl chloride (1 g) and 4-aminobutanol (1 g) were dissolved in dichloromethane (30 mL) containing pyridine (1 mL). The mixture was stirred overnight at room temperature. After washing with water the solvent was evaporated and the title compound obtained as a white crystalline solid following trituration with ether. $\delta_C$ (DMSO, 62.9

Example 22

4'-Fluorobiphenyl-4-sulfonic acid-(5-hydroxypentyl)-amide (ABD-205)

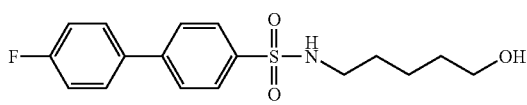

4'-Fluoro-biphenyl sulfonyl chloride (1 g) and 5-aminopentanol (1 g) were dissolved in dichloromethane (30 mL) containing pyridine (1 mL). The mixture was stirred overnight at room temperature. After washing with water the solvent was evaporated and the title compound obtained as a white solid following trituration with ether. $\delta_C$ (DMSO, 62.9 MHz): 22.6, 28.9, 32.0, 42.6, 60.5, 115.9 (d, J22.5), 127.1, 128.9 (d, J8.8), 129.1, 135.0 (d, J2.9), 139.3, 142.7 and 162.5 (d, J245.1).

Example 23

2'-Nitrobiphenyl sulfonic acid

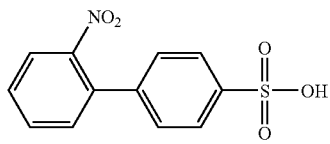

2'-Nitrobiphenyl (5 g) was added slowly to chlorosulfonic acid (25 mL) at room temperature and stirring was continued for 2 hours. The mixture was carefully dripped into ice water and extracted with DCM. The solvent was evaporated and the residue purified by column chromatography (petrol/ethyl acetate) to give the title compound as a yellow oil.

Example 24

2'-Nitrobiphenyl sulfonic acid

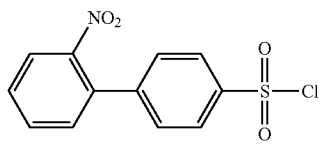

2'-Nitrobiphenyl sulfonic acid (2 g) was refluxed in thionyl chloride (30 mL) with a catalytic quantity of DMF (0.5 mL) for 4 hours. Toluene was added and the solvents evaporated under vacuum to give a yellow oil.

Example 25

2'-Nitrobiphenyl-4-sulfonic acid-(4-hydroxybutyl)-amide (ABD-227)

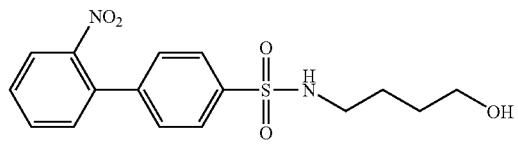

2'-Nitrobiphenyl sulfonyl chloride (1 g) and 4-aminobutanol (1 g) were dissolved in dichloromethane (30 mL) containing pyridine (1 mL). The mixture was stirred overnight at room temperature. After washing with water the solvent was evaporated to give a brown oil. The residue was purified by column chromatography (ethyl acetate/petrol) to give a yellow oil. The oil crystallised upon standing and was washed with ether to give the title compound as a pale yellow solid. $\delta_C$ (DMSO, 62.9 MHz): 25.9, 29.6, 42.6, 60.2, 124.6, 126.7, 128.9, 129.3, 131.9, 133.4, 134.1, 140.3, 141.1 and 148.5.

Example 26

2'-Nitrobiphenyl-4-sulfonic acid-(5-hydroxypentyl)-amide (ABD-234)

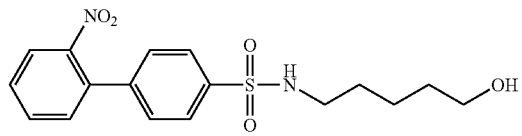

2'-Nitrobiphenyl sulfonyl chloride (0.5 g) and 5-aminopentanol (1 g) were dissolved in dichloromethane (30 mL) containing pyridine (1 mL). The mixture was stirred overnight at room temperature. After washing with water the solvent was evaporated and the title compound obtained as a yellow oil following repeated washing with ether.

Example 27

5-(Biphenyl-4-sulfonylamino)-pentanoic acid (ABD-222)

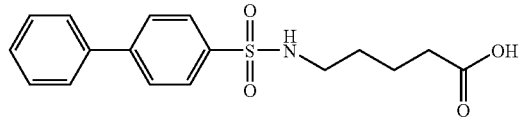

Biphenyl sulfonyl chloride (1 g) and 5-aminovaleric acid (1 g) were dissolved in dichloromethane containing pyridine (1 mL). The mixture was stirred for 2 hours at room temperature. After washing with water the solvent was evaporated and the title compound obtained as a white solid following trituration with ether (90%). $\delta_C$ (DMSO, 62.9 MHz): 21.7, 28.6, 33.1, 42.3, 127.1, 127.2, 127.6, 128.6, 129.2, 138.6, 139.3, 143.8 and 174.3.

Example 28

4-(Biphenyl-4-sulfonylamino)-butanoic acid (ABD-230)

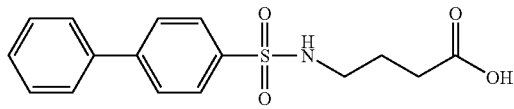

Biphenyl sulfonyl chloride (1 g) and gamma-aminobutyric acid (1 g) were dissolved in dichloromethane containing pyridine (1 mL). The mixture was stirred for 2 hours at room temperature. After washing with water the mixture was repeatedly extracted with ethyl acetate. The solvent was evaporated and the title compound obtained as a white solid.

Example 29

Biphenyl-4-sulfonic acid (4-amino-butyl)amide (ABD-250)

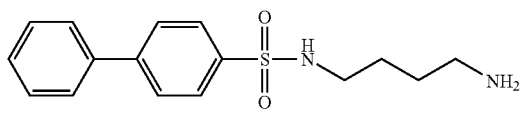

1,4-Diaminobutane (1 g) was dissolved in dichloromethane (30 mL). Biphenyl sulfonyl chloride (1 g) was added, followed by pyridine (1 mL), and the mixture was stirred for 1 hour. The solid was filtered to give the title compound as a white solid.

Example 30

N-(4-(Biphenyl-4-sulfonylamino)-butyl]-acetamide (ABD-251)

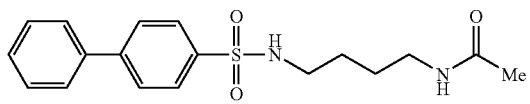

Biphenyl-4-sulfonic acid (4-amino-butyl)amide (1 g) was suspended in a mixture of acetic anhydride (45 mL) and pyridine (15 mL) and stirred at 80° C. for 4 hours. The solution was left to stir overnight and then poured into ice water. The aqueous mixture was extracted with dichloromethane, dried (Na₂SO₄) and evaporated to give a brown oil. The oil was redissolved in dichloromethane and the title compound precipitated as a white solid by addition of a small amount of petrol. $\delta_C$ (CDCl₃, 62.9 MHz): 23.2, 26.6, 26.8, 39.1, 42.9, 127.3, 127.6, 127.8, 128.5, 129.1, 138.4, 139.3, 145.6 and 170.9.

Example 31

4'-Bromobiphenyl-4-sulfonic acid (4-amino-butyl) amide (ABD-252)

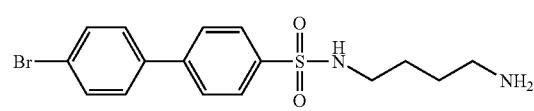

1,4-Diaminobutane (4 g) was dissolved in dichloromethane (30 mL). 4'-Bromobiphenyl sulfonyl chloride (2 g) was added, followed by pyridine (1 mL), and the mixture stirred for 1 hour. The mixture was filtered and the title compound collected as a white solid. Saturated Na₂CO₃ solution was added to the filtrate, which was extracted with ethyl acetate and evaporated to give additional product. $\delta_C$ (DMSO, 62.9 MHz): 26.7, 30.4, 41.2, 42.6, 122.1, 127.2, 127.3, 129.2, 132.0, 137.8, 139.8 and 142.5.

Example 32

3'-Nitrobiphenyl sulfonic acid

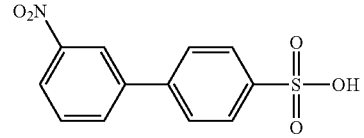

3'-Nitrobiphenyl (10 g) was added slowly to chlorosulfonic acid (20 mL) at room temperature and stirring was continued for 2 hours. The mixture was carefully dripped into ice water and extracted with DCM. The solvent was evaporated to give the title compound as a white powder.

Example 33

3'-Nitrobiphenyl sulfonyl chloride

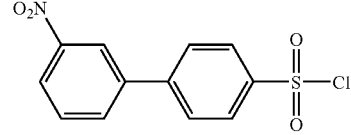

3'-Nitrobiphenyl sulfonic acid (2 g) was refluxed in thionyl chloride (30 mL) with a catalytic quantity of DMF (0.5 mL) for 4 hours. Toluene was added and the solvents evaporated under vacuum. The residue was recrystallised from ethyl acetate/petrol to give the title compound as white crystals.

Example 34

3'-Nitrobiphenyl-4-sulfonic acid-(4-hydroxybutyl)-amide (ABD-226)

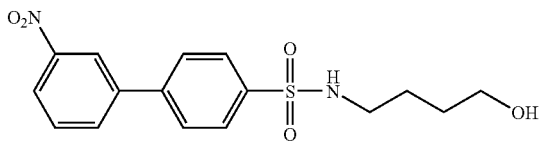

3'-Nitrobiphenyl sulfonyl chloride (1 g) and 4-aminobutanol (1 g) were dissolved in dichloromethane (30 mL) containing pyridine (1 mL). The mixture was stirred overnight at room temperature. After washing with water the solvent was evaporated and the title compound obtained as a yellow oil. The oil was purified by column chromatography (ethyl acetate/petrol) to give the title compound as an oil which eventually solidified to give a white powder. $\delta_C$ (DMSO, 62.9 MHz): 25.9, 29.6, 42.6, 60.2, 121.6, 123.1, 127.4, 127.9, 130.6, 133.5, 140.5, 141.4 and 148.5.

Example 35

4'-Bromo-2'-fluorobiphenyl sulfonic acid

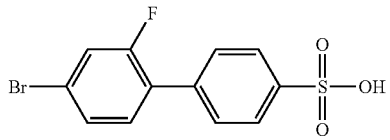

4'-Bromo-2'-fluorobiphenyl (5 g) was dissolved in chloroform (80 mL) at room temperature. Chlorosulfonic acid (5 g) was added dropwise and a precipitate appeared soon after addition was complete. Stirring was continued for a further 4 hours, after which the solid was collected by filtration. Further crops of crystals were collected from the filtrate. The solid was washed with cold chloroform and the washings also allowed to crystallise.

Example 36

4'-Bromo-2'-fluorobiphenyl sulfonyl chloride

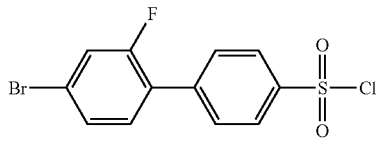

4'-Bromo-2'-fluorobiphenyl sulfonic acid (5 g) was refluxed in thionyl chloride (30 mL) with a catalytic quantity of DMF (0.5 mL) for 4 hours. Toluene was added and the solvents evaporated under vacuum. The residue collected was recrystallised from petrol/ethyl acetate to give white crystals.

Example 37

4'-Bromo-2'-fluorobiphenyl-4-sulfonic acid-(4-hydroxybutyl)-amide (ABD-265)

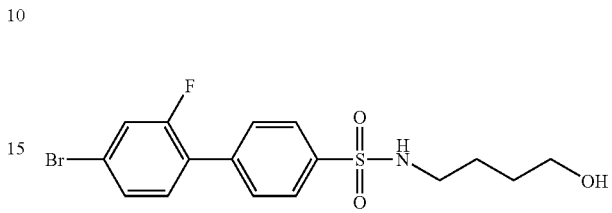

4'-Bromo-2'-fluorobiphenyl sulfonyl chloride (1 g) and 4-aminobutanol (1 g) were dissolved in dichloromethane (30 mL) containing pyridine (1 mL). The mixture was stirred overnight at room temperature. After washing with water the solvent was evaporated and the title compound obtained as a white crystalline solid following trituration with ether. $\delta_C$ (DMSO, 62.9 MHz): 25.9, 29.6, 42.6, 60.2, 119.3, 122.1 (d, J 9.8), 126.3 (d, J 12.7), 126.7 (d J 13.7), 128.2, 129.4, 132.2, 137.8, 140.2 and 158.9 (d, J 252.0).

Example 38

4-Bromophenyl sulfonic acid-(4-hydroxybutyl)-amide

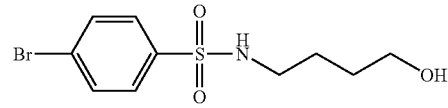

Using a method analogous to that described in Example 1,4-bromophenyl sulphonyl chloride was reacted with 4-aminobutanol, and the title compound obtained as a white solid after recrystallisation from ether/petrol.

Example 39

4-Bromophenyl sulfonic acid-(5-hydroxypentyl)-amide

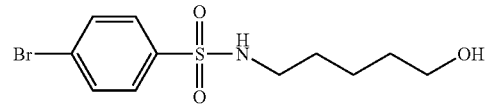

Using a method analogous to that described in Example 1,4-Bromophenyl sulphonyl chloride was reacted with 5-aminopentanol, and the title compound obtained as a white solid after recrystallisation from ether/petrol.

Example 40

4'-Trifluoromethylbiphenyl-4-sulfonic acid-(4-hydroxybutyl)-amide (ABD-246)

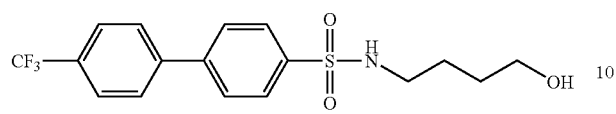

4-Bromophenyl-sulfonic acid-(4-hydroxybutyl)-amide (1 g) was dissolved in ethanol (8 mL) and toluene (8 mL). 4-Trifluoromethylphenyl boronic acid (1 g) was added, followed by 2 M $Na_2CO_3$ (8 mL). Tetrakis(triphenylphosphine)palladium (0.25 g) was added and the mixture heated to reflux under nitrogen for 3 hours with vigorous stirring. The organic solvents were evaporated and the residue dissolved in ethyl acetate (100 mL) and washed with water (100 mL) then saturated NaCl solution (100 mL). The organic phase was dried ($Na_2SO_4$), evaporated and the residue purified by column chromatography (ethyl acetate/petrol) to give the title compound as a white solid. $\delta_C$ (DMSO, 62.9 MHz): 25.9, 29.6, 42.6, 60.2, indistinct m, 140.4, 142.2 and 142.6. $\delta_H$ (DMSO, 250 MHz): 1.41 (4H, m), 2.77 (2H, m), 3.33 (2H, m), 4.39 (1H, t, NH), 7.83-7.94 (6 H, m) and 7.96 (2H, d, J 8.5).

Example 41

2',4'-Difluorobiphenyl-4-sulfonic acid-(5-hydroxypentyl)-amide (ABD-248)

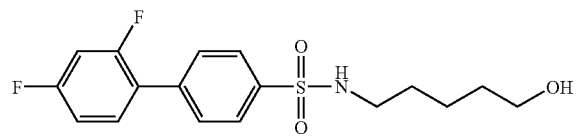

Using a method analogous to that described in Example 40, 4-bromophenyl-sulfonic acid-(5-hydroxypentyl)-amide and 2,4-difluorophenyl boronic acid were reacted to give the title compound as a white solid. $\delta_C$ (CDCl$_3$, 62.9 MHz): 22.7, 29.3, 31.9, 43.1, 62.5, 104.7 (t, J 25.8), 112.0 (dd, J 22.9 and 3.5), 127.3, 129.6, 131.5 (d, J 8.8), 131.5 (d, J 9.8), 139.1, 139.4, 159.8 (dd, J 252.0, 11.7) and 163.0 (dd, J 252.0, 11.7).

Example 42

2',4'-Difluorobiphenyl-4-sulfonic acid-(4-hydroxybutyl)-amide (ABD-256)

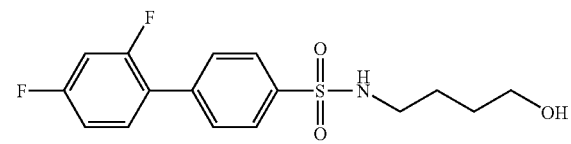

Using a method analogous to that described in Example 40, 4-bromophenyl-sulfonic acid-(4-hydroxybutyl)-amide and 2,4-difluorophenyl boronic acid were reacted to give the title compound as a white solid. $\delta_C$ (CDCl$_3$, 62.9 MHz): 25.9, 29.6, 42.6, 60.2, 104.7 (t, J 25.8), 112.0 (dd, J 22.9 and 3.5), 127.3, 129.6, 131.5 (d, J 8.8), 131.5 (d, J 9.8), 139.1, 139.4, 159.9 (dd, J 252.0, 11.7) and 163.0 (dd, J 252.0, 11.7).

Example 43

3',4'-Difluorobiphenyl-4-sulfonic acid-(5-hydroxypentyl)-amide (ABD-257)

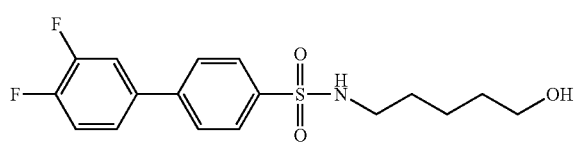

Using a method analogous to that described in Example 40, 4-bromophenyl-sulfonic acid-(5-hydroxypentyl)-amide and 3,4-difluorophenyl boronic acid were reacted to give the title compound as a white solid. $\delta_C$ (CDCl$_3$, 62.9 MHz): 22.7, 29.3, 31.9, 43.1, 62.5, 116.4 (d, J 17.6), 118.0 (d, J 17.6), 123.5 (d, J 4.9), 127.6, 127.8, 136.4 (m), 139.2, 143.3, 150.5 (d, J 250.0) and 150.7 (d, J 250.0).

Example 44

4'-Methylthiobiphenyl-4-sulfonic acid-(4-hydroxybutyl)-amide (ABD-258)

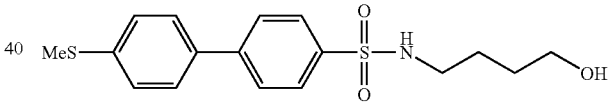

Using a method analogous to that described in Example 40, 4-bromophenyl-sulfonic acid-(4-hydroxybutyl)-amide and 4-methylthiophenyl boronic acid were reacted to give the title compound as a white solid. $\delta_C$ (DMSO, 62.9 MHz): 14.5, 25.9, 29.6, 42.6, 60.2, 125.9 126.2, 127.1, 127.3, 127.5, 134.8, 139.1 and 143.1.

Example 45

4'-Methylbiphenyl-4-sulfonic acid-(5-hydroxypentyl)-amide (ABD-260)

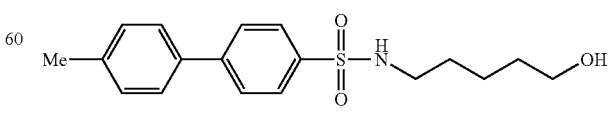

Using a method analogous to that described in Example 40, 4-bromophenyl-sulfonic acid-(5-hydroxypentyl)-amide and 4-methylphenyl boronic acid were reacted to give the title compound as a white solid. $\delta_C$ (DMSO, 62.9 MHz): 20.8, 22.6, 28.9, 32.0, 42.6, 60.5, 126.9, 127.0, 127.3, 129.7, 135.7, 138.0, 139.0 and 143.7.

Example 46

4'-Acetylbiphenyl-4-sulfonic acid-(5-hydroxypentyl)-amide (ABD-261)

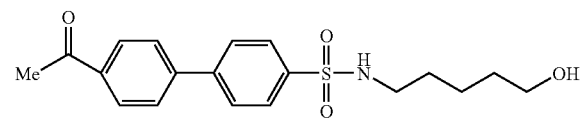

Using a method analogous to that described in Example 40, 4-bromophenyl-sulfonic acid-(5-hydroxypentyl)-amide and 4-acetylphenyl boronic acid were reacted to give the title compound as a white solid. $\delta_C$ (DMSO, 62.9 MHz): 22.6, 26.9, 28.9, 32.0, 42.6, 60.5, 127.0, 127.3, 127.9, 128.9, 136.4, 140.2, 142.5, 142.9 and 197.6.

Example 47

4'-Cyanobiphenyl-4-sulfonic acid-(5-hydroxypentyl)-amide (ABD-262)

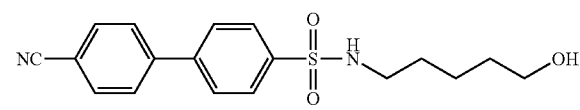

Using a method analogous to that described in Example 40, 4-bromophenyl-sulfonic acid-(5-hydroxypentyl)-amide and 4-cyanophenyl boronic acid were reacted to give the title compound as a white solid. $\delta_C$ (DMSO, 62.9 MHz): 22.6, 28.9, 32.0, 42.6, 60.5, 111.0, 118.7, 127.3 127.0, 127.9, 128.1, 133.0, 140.6, 141.9 and 143.1.

Example 48

2'-Aminobiphenyl-4-sulfonic acid-(4-hydroxybutyl)-amide (ABD-263)

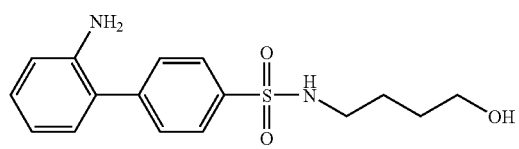

2'-Nitrobiphenyl-4-sulfonic acid-(4-hydroxybutyl)-amide (0.5 g) was dissolved in methanol (50 mL). 10% Pd/C (0.5 g) was added and the mixture stirred under hydrogen for 4 hours. The mixture was filtered through celite and evaporated to a brown oil. Column chromatography gave a clear oil, crystallised from ether/petrol to give a white powder. $\delta_C$ (DMSO, 62.9 MHz): 25.9, 29.6, 42.6, 60.3, 115.6, 116.8, 124.1, 126.8, 128.8, 129.3, 129.9, 138.6, 143.8 and 145.2.

Example 49

4'-Bromo-2'-fluorobiphenyl-4-sulfonic acid-(5-hydroxybutyl)-amide (ABD-266)

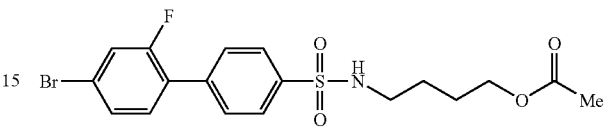

Using a method analogous to that described in Example 14, 4'-bromo-2'-fluorobiphenyl-4-sulfonic acid-(4-hydroxybutyl)-amide was acetylated with acetic anhydride and pyridine to give the title compound as a white solid. $\delta_C$ (CDCl$_3$, 62.9 MHz): 21.0, 25.7, 26.3, 42.9, 63.8, 120.0 (d, J26.4), 122.8 (d, J 9.8), 126.4 (d, J 13.7), 127.3, 128.2 (d, J 2.9), 129.6, 131.6 (d, J 2.9), 139.3, 139.3, 159.4 (d, J 254.0) and 171.2.

Example 50

2'-Methoxybiphenyl-4-sulfonic acid-(5-hydroxypentyl)-amide (ABD-267)

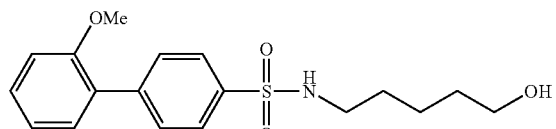

Using a method analogous to that described in Example 40, 4-bromophenyl-sulfonic acid-(5-hydroxypentyl)-amide and 2-methoxyphenyl boronic acid were reacted to give the title compound as a clear oil. $\delta_C$ (DMSO, 62.9 MHz): 22.7, 29.0, 32.0, 42.7, 55.6, 60.6, 115.5, 121.4, 125.3, 126.1, 128.2, 129.8, 130.2, 138.8, 142.1 and 156.1.

Example 51

4'-Carboxybiphenyl-4-sulfonic acid-(5-hydroxypentyl)-amide (ABD-271)

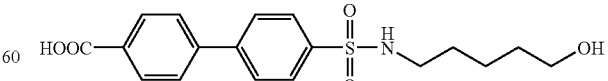

Using a method analogous to that described in Example 40, 4-bromophenyl-sulfonic acid-(5-hydroxypentyl)-amide and 4-carboxyphenyl boronic acid were reacted to give the title compound as a white solid. $\delta_C$ (DMSO, 62.9 MHz): 22.6, 28.9, 32.0, 42.6, 60.5, 127.2, 127.4, 127.7, 130.2, 130.5, 140.1, 142.7, 142.7 and 167.0.

Example 52

2'-Iodobiphenyl-4-sulfonic acid-(4-hydroxybutyl)-amide (ABD-275)

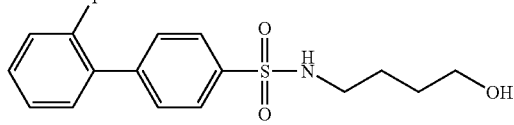

Using methods analogous to those described in Examples 18-20, the title compound was prepared as a white solid from 2-iodobiphenyl. $\delta_C$ (DMSO, 62.9 MHz): 25.9, 29.6, 42.6, 60.2, 98.2, 126.2, 126.3, 128.4, 129.7, 130.0, 139.8, 144.6 and 147.2.

Example 53

4'-Dimethylaminobiphenyl-4-sulfonic acid-(5-hydroxypentyl)-amide (ABD-276)

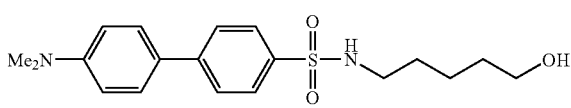

Using a method analogous to that described in Example 40, 4-bromophenyl-sulfonic acid-(5-hydroxypentyl)-amide and 4-dimethylaminophenyl boronic acid were reacted to give the title compound as a white solid. $\delta_C$ (DMSO, 62.9 MHz): 22.7, 28.9, 32.0, 39.9, 42.6, 60.5, 112.6, 125.5, 125.8, 127.1, 127.8, 137.5, 143.9 and 150.5.

Example 54

4'-Hydroxybiphenyl-4-sulfonic acid-(5-hydroxypentyl)-amide (ABD-277)

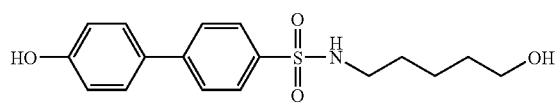

Using a method analogous to that described in Example 40, 4-bromophenyl-sulfonic acid-(5-hydroxypentyl)-amide and 4-hydroxyphenyl boronic acid were reacted to give the title compound as a white solid. $\delta_C$ (DMSO, 62.9 MHz): 22.6, 28.9, 32.0, 42.6, 60.5, 116.0, 126.4, 127.2, 128.2, 129.2, 138.1, 143.8 and 158.1.

Example 55

2',4'-Dichlorobiphenyl-4-sulfonic acid-(5-hydroxypentyl)-amide (ABD-278)

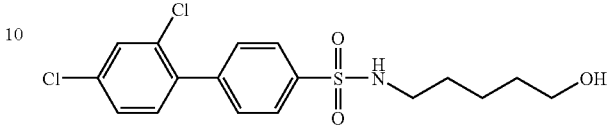

Using a method analogous to that described in Example 40, 4-bromophenyl-sulfonic acid-(5-hydroxypentyl)-amide and 2,4-dichlorophenyl boronic acid were reacted to give the title compound as a white solid. $\delta_C$ (DMSO, 62.9 MHz): 22.6, 29.0, 32.0, 42.7, 60.5, 126.5, 127.8, 129.5, 130.0, 132.3, 132.7, 133.7, 137.4, 140.3 and 141.3.

Example 56 p-Terphenyl-4-sulfonic acid-(5-hydroxypentyl)-amide (ABD-279)

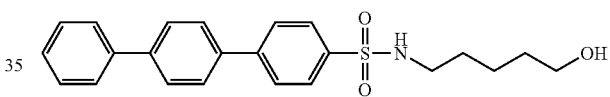

Using a method analogous to that described in Example 40, 4-bromobiphenyl-sulfonic acid-(5-hydroxypentyl)-amide (ABD-199) and phenyl boronic acid were reacted to give the title compound as a white solid. $\delta_C$ (DMSO, 62.9 MHz): MHz): 22.7, 29.0, 32.0, 42.7, 60.5, 126.7, 127.4, 129.1, 137.5, 139.4, 139.4, 140.1 and 143.2.

Example 57

3-Bromophenyl-sulfonic acid-(5-hydroxypentyl)-amide

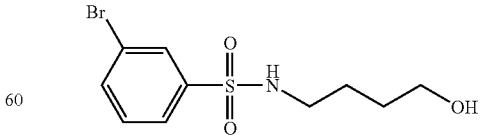

Using a method analogous to that described in Example 1, 3-bromophenyl sulphonyl chloride was reacted with 5-amnopentanol, and the title compound obtained as a white solid after recrystallisation from ether/petrol.

Example 58

4'-Trifluoromethylbiphenyl-3-sulfonic acid (4-hydroxy-butyl)-amide (ABD-283)

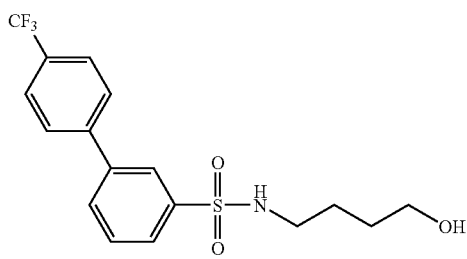

Using a method analogous to that described in Example 40, 3-bromophenyl-sulfonic acid-(4-hydroxybutyl)-amide and 4-trifluoromethylphenyl boronic acid were reacted to give the title compound as a white solid.

Example 59

2'-Trifluoromethylbiphenyl-4-sulfonic acid-(5-hydroxypentyl)-amide (ABD-284)

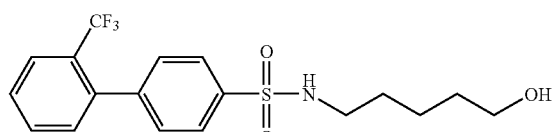

Using a method analogous to that described in Example 40, 4-bromophenyl-sulfonic acid-(5-hydroxypentyl)-amide and 2-trifluoromethylphenyl boronic acid were reacted to give the title compound as a white solid. $\delta_C$ (DMSO, 62.9 MHz): 22.6, 28.9, 32.0, 42.7, 60.5, 121.9, 126.2, 126.5, 127.1, 128.8, 129.8, 132.0, 132.6, 139.2, 140.2 and 143.1.

Example 60

4-Bromo-2-fluorophenyl-sulfonic acid-(4-hydroxybutyl)-amide

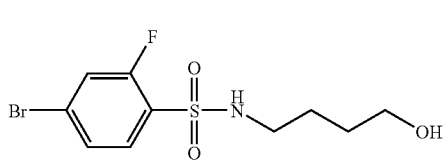

Using a method analogous to that described in Example 1, 4-bromo-2-fluorophenyl sulphonyl chloride was reacted with 4-aminobutanol, and the title compound obtained as a white solid after recrystallisation from ether/petrol.

Example 61

4-Bromo-3-fluorophenyl-sulfonic acid-(4-hydroxybutyl)-amide

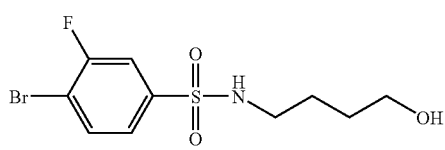

Using a method analogous to that described in Example 1, 4-bromo-3-fluorophenyl sulphonyl chloride was reacted with 4-aminobutanol, and the title compound obtained as a white solid after recrystallisation from ether/petrol. $\delta_C$ (CDCl$_3$, 62.9 MHz): 26.5, 29.4, 43.2, 62.2, 114.5 (d, J 20.5), 115.3 (d, J 25.4), 123.7 (d, 3.9), 134.5, 141.2 (d, 5.9) and 158.9 (d, J 252).

Example 62

4-Bromo-3-methylphenyl-sulfonic acid-(4-hydroxybutyl)-amide

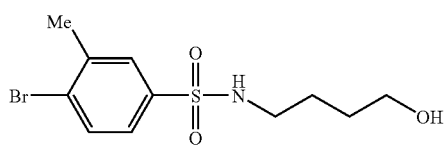

Using a method analogous to that described in Example 1, 4-bromo-3-methylphenyl sulphonyl chloride was reacted with 4-aminobutanol, and the title compound obtained as a white solid after recrystallisation from ether/petrol.

Example 63

4-Bromo-2-trifluoromethylphenyl-sulfonic acid-(4-hydroxybutyl)-amide

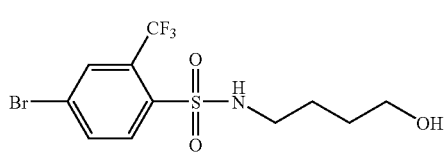

Using a method analogous to that described in Example 1, 4-bromo-2-trifluoromethylphenyl sulphonyl chloride was reacted with 4-aminobutanol, and the title compound obtained as a white solid after recrystallisation from ether/petrol. $\delta_C$ (CDCl$_3$, 62.9 MHz): 26.5, 29.4, 43.3, 62.1, 127.3, 131.7, 131.7, 133.1, 135.4 and 137.9.

Example 64

2-Fluoro-4'-trifluoromethylbiphenyl-4-sulfonic acid-(4-hydroxybutyl)-amide (ABD-294)

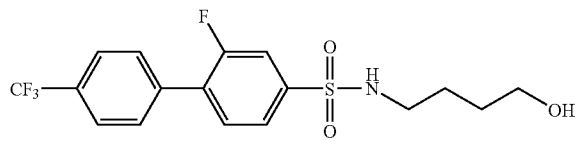

Using a method analogous to that described in Example 40, 4-bromo-3-fluorophenyl-sulfonic acid-(4-hydroxybutyl)-amide and 4-trifluoromethylphenyl boronic acid were reacted to give the title compound as a white solid. $\delta_C$ (DMSO, 62.9 MHz): 26.4, 29.5, 43.2, 62.2, 115.4 (d, J 25.4), 123.2, 125.7, 129.4, 130.8 (d, J 22.2), 131.6, 137.6, 141.5 (d, J 6.8) and 159.3 (d, J 253.9).

Example 65

2',4'-Difluoro-2-methylbiphenyl-4-sulfonic acid-(4-hydroxybutyl)-amide (ABD-295)

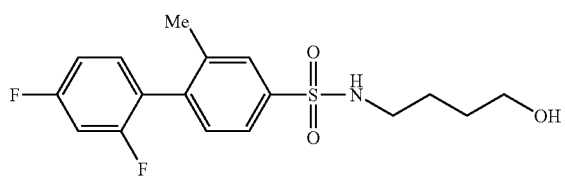

Using a method analogous to that described in Example 40, 4-bromo-3-methylphenyl-sulfonic acid-(4-hydroxybutyl)-amide and 2,4-difluorophenyl boronic acid were reacted to give the title compound as a thick oil. $\delta_C$ (DMSO, 62.9 MHz): 20.0, 26.4, 29.5, 43.1, 62.2, 104.2 (t, 25.4), 111.6 (d, J 21.5), 123.8 (d J 11.7), 124.4, 128.4, 131.7, 131.8 (m), 138.4, 139.4 (d, J 3.9), 159.4 (d J 250.0, 11.7) and 162.8 (dd 250.0, J 11.7).

Example 66

4'-Ethoxybiphenyl-4-sulfonic acid-(5-hydroxypentyl)-amide (ABD-297)

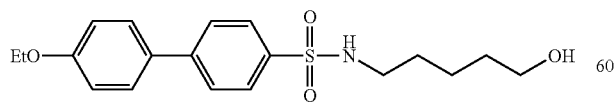

Using a method analogous to that described in Example 40, 4-bromophenyl-sulfonic acid-(5-hydroxypentyl)-amide and 4-ethoxyphenyl boronic acid were reacted to give the title compound as a white solid. $\delta_C$ (DMSO, 62.9 MHz): 14.7, 22.6, 28.9, 32.0, 42.6, 60.5, 63.2, 115.0, 126.6, 127.1, 128.2, 130.6, 138.4, 143.5 and 158.9.

Example 67

3-Fluoro-4'-trifluoromethylbiphenyl-4-sulfonic acid-(4-hydroxybutyl)-amide (ABD-302)

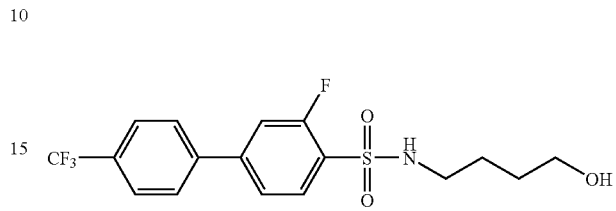

Using a method analogous to that described in Example 40, 4-bromo-2-fluorophenyl-sulfonic acid-(4-hydroxybutyl)-amide and 4-trifluoromethylphenyl boronic acid were reacted to give the title compound as a white solid. $\delta_C$ (DMSO, 62.9 MHz): 26.4, 29.5, 43.2, 62.2, 115.4 (d, J 25.4), 123.2, 125.7, 129.4, 130.8 (d, J 22.2), 131.6, 137.6, 141.5 (d, J 6.8) and 159.3 (d, J 253.9).

Example 68

4'-Trifluoromethoxybiphenyl-4-sulfonic acid-(4-hydroxybutyl)-amide (ABD-306)

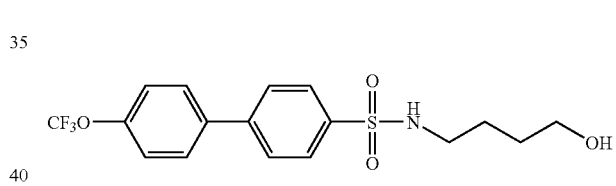

Using a method analogous to that described in Example 40, 4-bromophenyl-sulfonic acid-(4-hydroxybutyl)-amide and 4-trifluoromethoxyphenyl boronic acid were reacted to give the title compound as a white solid. $\delta_C$ (DMSO, 62.9 MHz): 25.9, 29.6, 42.6, 60.2, 121.7, 127.1, 127.4, 129.0, 137.9, 139.8, 142.3 and 148.5.

Example 69

3'-Methylbiphenyl-4-sulfonic acid-(4-hydroxybutyl)-amide (ABD-308)

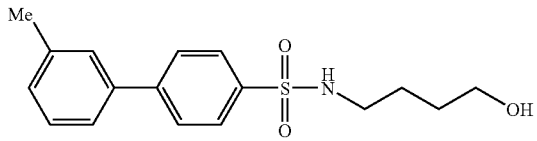

Using a method analogous to that described in Example 40, 4-bromophenyl-sulfonic acid-(4-hydroxybutyl)-amide and 3-methylphenyl boronic acid were reacted to give the title compound as a white solid. $\delta_C$ (DMSO, 62.9 MHz): 21.1, 25.8, 29.5, 42.6, 60.2, 124.1, 127.1, 127.3, 129.0, 138.4, 138.6, 139.2 and 143.9.

Example 70

3-Trifluoromethylbiphenyl-4-sulfonic acid-(4-hydroxybutyl)-amide (ABD-310)

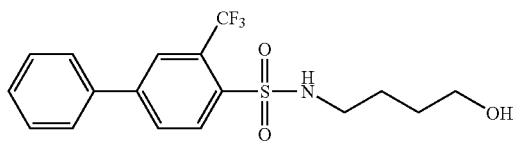

Using a method analogous to that described in Example 40, 4-bromo-2-trifluoromethylphenyl-sulfonic acid-(4-hydroxybutyl)-amide and phenyl boronic acid were reacted to give the title compound as a white solid. $\delta_C$ (DMSO, 62.9 MHz): 26.1, 29.5, 42.8, 60.2, 125.1, 126.6, 127.2, 127.4, 129.2, 130.8, 132.5, 137.1, 138.3 and 144.0.

Example 71

4'-Fluoro-2-methylbiphenyl-4-sulfonic acid-(4-hydroxybutyl)-amide (ABD-320)

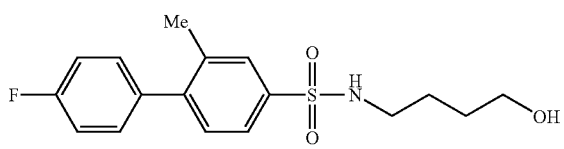

Using a method analogous to that described in Example 40, 4-bromo-3-methylphenyl-sulfonic acid-(4-hydroxybutyl)-amide and 4-fluorophenyl boronic acid were reacted to give the title compound as a thick oil. $\delta_C$ (CDCl$_3$, 62.9 MHz): 20.6, 26.4, 29.6, 43.1, 62.2, 115.4 (d, J 21.5), 124.5, 128.8, 130.5, 130.6, 136.1 (d, J 2.9), 136.9, 138.6, 145.3 and 162.4 (d, J 247.1).

Example 72

4-Bromo-2-chloromethylphenyl-sulfonic acid-(4-hydroxybutyl)-amide

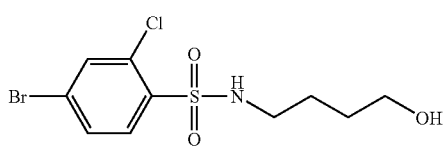

Using a method analogous to that described in Example 1, 4-Bromo-2-chlorophenyl sulphonyl chloride was reacted with 4-aminobutanol, and the title compound obtained as a white solid after recrystallisation from ether/petrol. $\delta_C$ (CDCl$_3$, 62.9 MHz): 26.5, 29.4, 43.3, 62.1, 127.3, 131.7, 131.7, 133.1, 135.4 and 137.9.

Example 73

3-Chloro-2',4'-difluoro-biphenyl-4-sulfonic acid-(4-hydroxybutyl)-amide (ABD-325)

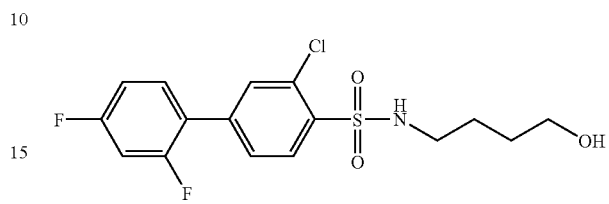

Using a method analogous to that described in Example 40, 4-bromo-2-chlorophenyl-sulfonic acid-(4-hydroxybutyl)-amide and 2,4-difluorophenyl boronic acid were reacted to give the title compound as a white solid. $\delta_C$ (CDCl$_3$, 62.9 MHz): 26.4, 29.5, 41.2, 62.1, 104.9 (t, J 26.0), 112.3 (dd, J 21.3, 2.9), 122.3 (dd, J 12.7, 3.9), 127.5, 131.3, 131.5, 131.5, 131.7 (d, J 2.0), 136.2, 140.6, 159.9 (dd, J 252.0, 11.7) and 163.3 (dd, J 252.0, 11.7).

Example 74

4-Bromo-2-trifluoromethoxyphenyl-sulfonic acid-(4-hydroxybutyl)-amide

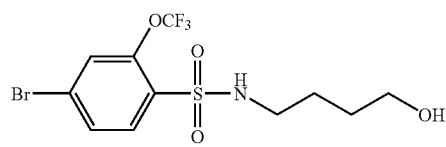

Using a method analogous to that described in Example 1, 4-bromo-2-trifluoromethoxyphenyl sulphonyl chloride was reacted with 4-aminobutanol, and the title compound obtained as a white solid after recrystallisation from ether/petrol. $\delta_C$ (CDCl$_3$, 62.9 MHz): 26.5, 29.4, 43.3, 62.1, 127.3, 131.7, 131.7, 133.1, 135.4 and 137.9.

Example 75

2',4'-Difluoro-3-trifluoromethoxybiphenyl-4-sulfonic acid-(4-hydroxybutyl)-amide (ABD-360)

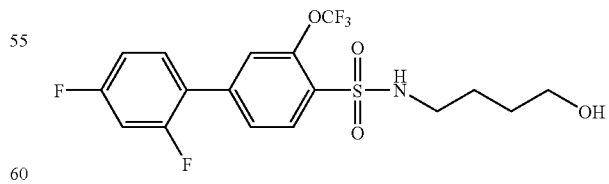

Using a method analogous to that described in Example 40, 4-bromo-2-trifluoromethoxyphenyl-sulfonic acid-(4-hydroxybutyl)-amide and 2,4-difluorophenyl boronic acid were reacted to give the title compound as a white powder. $\delta_C$ (CDCl$_3$, 62.9 MHz): 26.4, 29.5, 41.2, 62.1, 104.9 (t, J 26.0), 112.3 (dd, J 21.3, 2.9), 122.3 (dd, J 12.7, 3.9), 127.5, 131.3, 131.5, 131.5, 131.7 (d, J 2.0), 136.2, 140.6, 159.9 (dd, J 252.0, 11.7) and 163.3 (dd, J 252.0, 11.7).

Example 76

2'-Nitro-3-trifluoromethylbiphenyl-4-sulfonic acid-(4-hydroxybutyl)-amide (ABD-365)

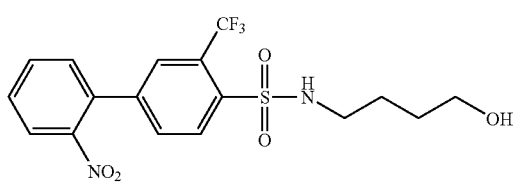

Using a method analogous to that described in Example 40, 4-bromo-2-trifluoromethylphenyl-sulfonic acid-(4-hydroxybutyl)-amide and 2-nitrophenyl boronic acid were reacted to give the title compound as a thick oil. $\delta_C$ (DMSO, 62.9 MHz): 26.1, 29.5, 42.8, 60.2, 128.2, 124.9, 120.7, 128.7, 130.2, 132.6, 133.1, 133.5, 139.3, 139.8, 141.8 and 147.9.

Example 77

4'Trifluoromethylbiphenyl-4-sulfonic acid-(4-hydroxybutyl)-methyl-amide (ABD-259)

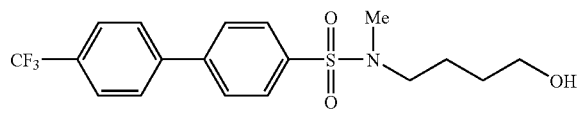

Using a method analogous to that described in Example 4, 4'-trifluoromethylbiphenyl-4-sulfonic acid-(4-hydroxypentyl)-amide and methyl iodide were reacted to give the title compound as a white solid.

Example 78

4'-Bromobiphenyl-4-sulfonic acid (4-isopropylamino-butyl) amide (ABD-255)

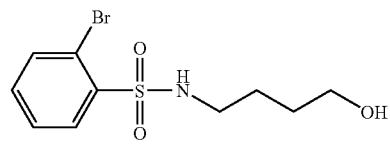

4'-Bromobiphenyl-4-sulfonic acid (4-amino-butyl) amide (0.6 g) was dissolved in DMF (30 mL). K₂CO₃ (1 g) was added followed by 2-iodo-propane (0.3 mL). The mixture was stirred for 3 hrs, poured into water, extracted with ether and dried. Addition of petrol and evaporation caused the title compound to precipitate as a white solid.

Example 79

2'-Fluorobiphenyl-4-sulfonic acid-(4-hydroxybutyl)-amide (ABD-269)

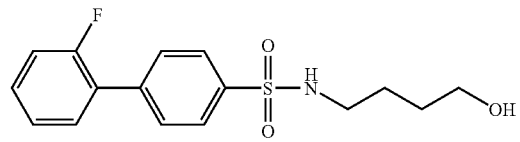

Using a method analogous to that described in Example 40, 4-bromophenyl-4-sulfonic acid-(4-hydroxybutyl)-amide and 2-fluorophenyl boronic acid were reacted to give the title compound as a white solid.

Example 80

2-Bromophenyl-N-(4-hydroxybutyl)-benzenesulfonamide

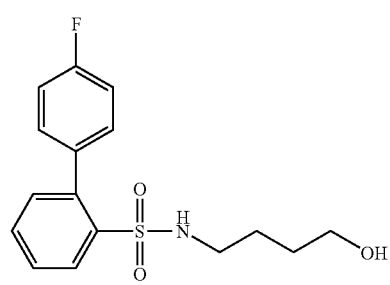

Using a method analogous to that described in Example 1, 2-bromophenyl sulphonyl chloride was reacted with 4-aminobutanol, and the title compound obtained as a clear oil.

Example 81

4'-Fluorobiphenyl-2-sulfonic acid (4-hydroxybutyl)-amide (ABD-282)

Using a method analogous to that described in Example 40, 2-bromophenyl-4-sulfonic acid-(4-hydroxybutyl)-amide and 4-fluorophenyl boronic acid were reacted to give the title compound as a clear oil.

Example 82

1',2',3',4',5',6'-Pentafluorobiphenyl-4-sulfonic acid-(4-hydroxybutyl)-amide (ABD-289)

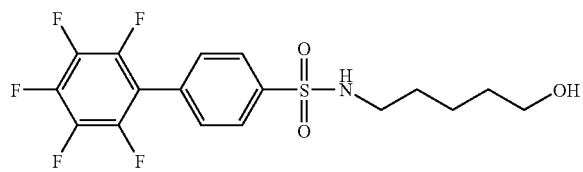

Using a method analogous to that described in Example 40, 4-bromophenyl-4-sulfonic acid-(4-hydroxybutyl)-amide and pentafluorophenyl boronic acid were reacted to give the title compound as a white solid.

Biological Studies

Initial screening of candidate compounds was performed using viability assays, on cultures of the macrophage cell line J774, which have been used before as a model system for osteoclast survival (see, e.g., Luckman et al., 1998). The assays are based on the survival of the J774 macrophage cell line; macrophages are closely related to osteoclasts, and contain similar high levels of esterase activity.

Alamar Blue Macrophage J774 Viability Assay

J774 cells were plated at $10^4$ cells per well in 150 µL αMEM (α Modified Eagle Medium) in 96-well plates and grown overnight. The next day, compounds were added to the cultures, and culture was continued for another 72 hours. At the end of the culture period cell survival was determined using an Alamar Blue assay as previously described (see, e.g., Nociari et al., 1998).

Alamar Blue is an oxidation-reduction sensitive indicator. The dye itself is in the oxidised state, which is blue and non-fluorescent. The dye can accept electrons from reducing species, such as NADPH and FADH, to form a reduced dye species, which is red and fluorescent. Thus the transformation from oxidised form to reduced form can be measured by fluorimetric or colourimetric means. For fluorescence measurements, 530-560 nm excitation and 590 nm emission wavelengths are typically used. For colourimetric measurements, absorbance is measured at 570 nm (reduced form) and 600 nm (oxidised form) and a simple calculation performed to determine the relative quantities of the two species.

A high ratio of the reducing species, NADPH and FADH, to the corresponding oxidised species, NADP and FAD, is an indicator that cells are proliferating and viable. A low ratio indicates cells that are quiescent or non-viable.

Briefly, Alamar Blue (Biosource International) was added undiluted to the each well (1:10 v/v, 15 µL). The plate was incubated at 37° C. for 3-4 hours and the fluorescence was measured at 570 nm, with a 25 nm bandwidth. A high reading indicated cells with normal viability, and a low reading indicates cells that have been damaged and are no longer proliferating normally. The controls gave a high fluorescence reading, indicating a high number of live, healthy cells. A potent test compound gave a low fluorescence reading. The average results for each test compound (n=5) were expressed as a percent (%) of the average control value.

Addition of Compounds. All of the compounds studied were made up as 100 mM solutions in DMSO. These stock solutions were then diluted 100 or 1000× in culture medium (αMEM). From these 1 mM or 100 µM solutions, convenient quantities (3-15 µL) were added directly to the wells so as to give the desired final compound concentration.

This assay offers numerous advantages over other assays, including MTT assays: it permits a higher throughput; it is more sensitive; it is non-damaging to the cells; it is faster; it generally gives an identical result to MTT assay.

Alamar Blue Mouse Osteoblast Assay

Osteoblasts were isolated as described above and plated at $10^4$ cells/well in 96-well plates in 100 µL of □MEM supplemented with 10% FCS and antibiotics. Test compounds were added after 24 hours and left for 72 hours. Cell viability was assessed using the Alamar Blue assay as described for J774 macrophages. Alamar Blue (Biosource International) was added undiluted to each well (1:10 v/v, 10 µL). The plate was incubated at 37° C. for 3 to 4 hours and the fluorescence was measured at 570 nm, with a 25 nm bandwidth.

Additional Studies

Some compounds were further evaluated in a model system of true osteoclasts: the murine co-culture system.

Murine Co-Culture System

The first model system, the murine co-culture system, studies the formation of osteoclasts from precursors present in the bone marrow. The number of osteoclasts and the amount of dentine resorption was measured.

Osteoclast formation and activity was studied using an adaptation (see, e.g., van't H of & Ralston, 1997) of the osteoblast-bone marrow co-culture assay originally described by Takahashi et al., 1988.

Co-Culture Methods. Co-culture (see, e.g., Van't H of et al., 1997) is a method to study the formation of osteoclasts from their precursors. In this assay, osteoblasts were obtained from the calvaria of 2-3 day old neonatal mice. These were plated on dentine, stimulated with 1,25-dihydroxy vitamin $D_3$ to stimulate RANKL and M-CSF expression. Early osteoclast precursors were present in the bone marrow of adult mice. The bone marrow suspension was purified to remove the red blood cells and the remainder cultured on top of the osteoblast layer. The stimulatory factors then allowed the osteoclast precursors to differentiate into mature osteoclasts. At the end of the culture osteoclasts were identified by TRAcP staining and the resorption activity was measured in the same manner as for rabbit osteoclasts.

Although it is possible to generate osteoclasts from bone marrow cells alone by treating the cultures with RANKL and M-CSF, the co-culture system is still regarded as one of the most reliable and reproducible available. It is useful for studying the effects of drugs on both osteoclast progenitors and mature osteoclasts.

Preparation of Dentine. the Dentine was Elephant Ivory, Preferred to Bone Because of its uniform surface, which facilitates easy visualisation of resorption pits. It was cut into slices of approximately 200 µm thickness using a Buehler Isomet low speed saw with a diamond wafering blade (series 15 HC). These slices were polished by hand, to a high degree, until one side was shiny. Out of these slices, discs were punched that fit the wells of a 96 well plate, using a paper puncher. Excess residues from the polish were removed by sonication. The discs were then stored in 70% ethanol until required. These discs were then dried and placed shiny side up in the wells of a 96 well plate. Cells were seeded onto the dentine. Following completion of the culture, these dentine slices were carefully removed from the plate and studied under the microscope.

Osteoblast Isolation. Briefly, osteoblasts were isolated from the calvarial bones of 2-day-old mice by sequential collagenase digestion (type I collagenase, Sigma) and cultured in αMEM supplemented with 10% FCS (foetal calf serum) and penicillin and streptomycin at 37° C. in 5% $CO_2$.

More specifically, osteoblasts were obtained from a collagenase digestion of the calvaria (skull bones) of 2-3 day old neo-natal C57/bl6 mice. At this stage in their development these are soft and easily removed. The calvaria from 5-6 mice were carefully dissected and washed in HBSS (Hank's balanced saline solution). The calvaria were placed in a 15 mL tube and shaken at 37° C. in 4 mL collagenase (10 mg/ml) for 10 minutes. This removes the excess unwanted tissue. The liquid was disposed of and a further 4 mL collagenase (10 mg/ml) added to the tube. The calvaria were then digested for a further 30 minutes. After this the supernatant (F1) was removed and retained. The calvaria were washed with a 2×4 mL PBS and this was added to F1. 4 mL EDTA (ethylene diamine tetraacetic acid) (4 mM in PBS) was then added to complex the calcium and allow further extraction of osteoblasts. This was shaken for 10 minutes at 37° C. The supernatant was removed and retained (F2). The calvaria were again washed with 2×4 mL HBSS and this was added to F2. The final 4 mL of collagenase (10 mg/ml) was added to the tube and this was again shaken at 37° C. for 30 minutes. Whilst this was being done, F1 and F2 were spun down at 300 g for 3 minutes, brake 3. The pellets were re-suspended in 1 mL medium (αMEM supplemented with 10% FCS (foetal calf serum) and penicillin and streptomycin), combined and added to 10 mL medium in two 75 $cm^2$ flasks. The liquid from the final collagenase digestion was collected (F3), the calvaria washed and the combined liquid extracts spun down in the centrifuge. The pellet was re-suspended in 1 mL medium and added in equal proportions to the flasks containing F1 and F2. The flasks were left for 4-6 hours at 37° C. and then the medium was changed to remove any non-adherent cells. These flasks may be left for up to 4 days at 37° C., 5% $CO_2$.

Osteoblast Plating. The medium was removed from the flasks and the cells washed with PBS. 2 mL Trypsin was added to the cells and these were incubated at 37° C. for 2 minutes. The flasks usually required gentle agitation to fully loosen the cells. 4 mL medium supplemented with 10% FCS was added to stop the enzymatic action. The cells were removed and the flask washed out with medium. The cell suspension was spun down at 300 g for 3 minutes, the medium removed and the pellet re-suspended in 1 mL medium. The cells were counted and then seeded in a 96 well plated containing dentine slices, at $8 \times 10^3$ cells per well in 100 µl medium containing 1000× dilution of stock 1,25-dihydroxyvitamin $D_3$ (final conc. 10 nM/well) to stimulate the expression of RANKL and cultured overnight.

Isolation of Bone Marrow Cells. Briefly, bone marrow cell populations containing osteoclast precursors were isolated from the long bones of 3-5 month old mice and erythrocytes were removed by Ficoll Hypaque density gradient centrifugation. The resulting bone marrow cells were washed with PBS (phosphate buffered saline) and re-suspended in culture medium.

More specifically, the femurs and tibia were dissected from 2-3 adult C57/bl6 mice (3-6 months old) and the surrounding tissue was removed. The bones were trimmed to allow access to the bone marrow. The marrow was flushed out using a 25G needle and HBSS+10% FCS. A single cell suspension is obtained by repeatedly squeezing the cell suspension through needles of decreasing size (start with 19G, end with 25G). 5 mL Ficoll was added to a 15 mL tube and the cell suspension carefully placed on top of this with the minimum amount of mixing between the layers. The density centrifugation was performed at 600 g, 25 minutes, brake off. This was sufficient to allow the red blood cells to congregate at the bottom of the tube, fats to remain at the top of the liquid and the desired bone marrow cells to collect at the interface. The cloudy layer from the interface was collected with a pipette, placed in a fresh 15 mL tube and made up to 12 mL with HBSS. The cell suspension was spun down at 300 g for 3 minutes. The pellet was collected and re-suspended in 1 mL medium. The bone marrow cells were counted and then added to the 96 well plate containing the osteoblasts at $2 \times 10^5$ cells/well in 50 µL medium.

Osteoclast Precursor Studies. To investigate the effects of a drug on osteoclast precursors the timetable was as follows:
Day 0—Plate osteoblasts.
Day 1—Plate bone marrow cells
Day 2—Add test compound.
Day 4—100% medium refresh+1,25-dihydroxyvitamin $D_3$ (final conc. 10 nm/well)
Day 6—Add IL1 (10 u/ml) and 1,25-dihydroxyvitamin $D_3$ (final conc. 10 nm/well)
Day 10—Fix cells.

Mature Osteoclast Studies. To investigate the effects of a drug on mature osteoclasts the timetable was as follows:
Day 0—Plate osteoblasts.
Day 1—Plate bone marrow cells.
Day 6—50% medium refresh+10 nM IL1 and 1,25-dihydroxyvitamin $D_3$.
Day 7—Add drugs and remove and fix day 7 control slices.
Day 10—Fix cells.

At the conclusion of a study, the cells were fixed in 4% formaldehyde for 10 minutes and washed in PBS. Fixed cells were either stained and kept in 70% ethanol or refrigerated in water or PBS. The 50% medium refresh involved the addition of 150 µL fresh medium containing a 500× dilution of 1,25-dihydroxyvitamin $D_3$ and a 250× dilution of IL1 (interleukin 1). This was left for 15 minutes and then 150 µL medium carefully removed. The medium refresh must be done very carefully, because the confluent layer of osteoblasts can be quite easily disturbed, and detached. This would result in a total absence of osteoclasts. Usually the first osteoclasts and resorption pits appeared on day 6. Reasonable numbers of osteoclasts were present between day 7-10.

At the end of the culture, the osteoclasts were identified by staining for tartrate-resistant acid phosphatase (TRAcP) staining and resorption pit area was quantified by reflected light microscopy as described previously (see, e.g., van't Hof & Ralston, 1997).

TRAcP Staining. Osteoclasts express very high levels of the enzyme tartrate resistant acid phosphatase (TRAcP) and can therefore be easily visualised by staining for this enzyme, for example, by the following method. Two staining solutions, (1) and (2), were made up freshly as follows:

| Solution 1. | 300 µL | Naphthol-AS-BI-phosphate stock. |
|---|---|---|
| | 1.5 mL | Veronal buffer. |
| | 1.8 mL | Acetate buffer. |
| | 1.8 mL | Acetate buffer with 100 mM tartrate. |
| Solution 2. | 240 µL | Pararosaniline. |
| | 240 µL | $NaNO_2$ (4% stock solution). |

Naphthol-AS-BI-phosphate stock: 10 mg/ml Naphthol-AS-BI-phosphate in dimethylformamide.

Veronal buffer: 1.17 g anhydrous Sodium Acetate; 2.94 g Veronal (sodium barbiturate); dissolved in 100 mL distilled water.

Acetate buffer 0.1 M, pH 5.2: solution (a): 0.82 g Sodium Acetate anhydrous dissolved in 100 mL distilled water; solution (b): 0.6 mL Acetic acid glacial made up to 100 mL with distilled water; pH of solution (a) adjusted to pH 5.2 with solution (b).

Pararosaniline: 1 g Pararosaniline in 20 mL distilled water. 5 mL concentrated hydrochloric acid was added, the solution was heated carefully in a water bath while stirring. The solution was allowed to cool and then filtered. Solutions (1) and (2) were mixed and filtered to give the staining solution. The PBS from the wells was removed and at least 50 μL of staining solution added. The cells were incubated at 37° C. for about 45 minutes, or until the dentine slices appeared sufficiently red. To determine what passes as sufficient it was necessary to remove the dentine slice and check under a light microscope that the osteoclasts were suitably stained. The staining solution was then removed and replaced with 70% ethanol. The dentine slices were stored in a refrigerator.

Osteoclast Counting. This was done using a light microscope to determine the number of TRAcP positive multinucleated cells on each dentine slice. The slices were carefully removed from the 96-well plate, avoiding disturbance of the cell layer, and placed on a glass slide. A few drops of 70% ethanol were put on each slice followed by a glass coverslip. Working across the dentine the number of multinucleated, red-stained cells were counted. There were usually a large number of small red mononucleated cells. These were osteoclast precursors and these were not counted. The numbers of osteoclasts on the control slices can range from 300 up to 1000. For each compound or concentration studied, the average of the values for the 5 slices was taken and expressed as a percent (%) of the average value for the controls. Any obvious outlying values were ignored. The most common reason for this was when there were no cells of any kind, usually indicating that the osteoblast layer has detached during handling.

Additional biological methods that may be suitable in the assessment and use of the compounds of the present invention are described, for example, in Ralston et al., 2003 and Ralston et al., 2004.

Biological Data

Examples of the claimed compounds were synthesized and tested for their biological activity using methods as described above.

For example, $IC_{50}$ values were determined for many biphenyl compounds using the Alamar Blue macrophage J774 viability assay described above. The results are summarised in the following table.

TABLE 1

Alamar Blue Macrophage J774 Viability Assay Results

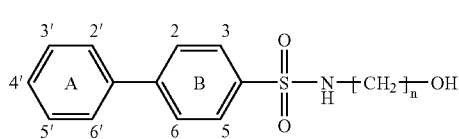

| Compound | Ring A Substituents | Ring B Substituents | n | $IC_{50}$ (J774) (μM) |
|---|---|---|---|---|
| ABD-365 | 2'-Nitro | 3-Trifluoromethyl | 4 | 0.3 ± 0.1 |
| ABD-295 | 2',4'-Difluoro | 2-Methyl | 4 | 0.8 ± 0.1 |
| ABD-360 | 2',4'-Difluoro | 3-Trifluoromethoxy | 4 | 1 ± 0.3 |
| ABD-227 | 2'-Nitro | H | 4 | 2 ± 0.5 |
| ABD-320 | 4'-Fluoro | 2-Methyl | 4 | 2.5 ± 0.2 |
| ABD-325 | 2',4'-Dichloro | H | 5 | 2.5 ± 0.5 |
| ABD-265 | 4'-Bromo-2'-fluoro | H | 4 | 3 ± 1 |
| ABD-325 | 2',4'-Difluoro | 3-Chloro | 4 | 3.5 ± 0.5 |
| ABD-248 | 2',4'-Difluoro | H | 5 | 4.5 ± 1 |

TABLE 1-continued

Alamar Blue Macrophage J774 Viability Assay Results

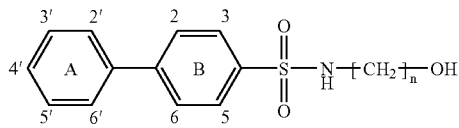

| Compound | Ring A Substituents | Ring B Substituents | n | $IC_{50}$ (J774) (μM) |
|---|---|---|---|---|
| ABD-310 | H | 3-Trifluoromethyl | 4 | 4.5 ± 1 |
| ABD-246 | 4'-Trifluoromethyl | H | 4 | 5 ± 1 |
| ABD-294 | 4'-Trifluoromethyl | 2-Fluoro | 4 | 5 ± 1 |
| ABD-302 | 4'-Trifluoromethyl | 3-Fluoro | 4 | 5.5 ± 1.5 |
| ABD-275 | 2'-Iodo | H | 4 | 5.5 ± 1.5 |
| ABD-284 | 2'-Trifluoromethyl | H | 5 | 6 ± 1.5 |
| ABD-306 | 2'-Trifluoromethoxy | H | 4 | 8 ± 1 |
| ABD-200 | 4'-Fluoro | H | 4 | 8 ± 2.5 |
| ABD-199 | 4'-Bromo | H | 4 | 8 ± 2 |
| ABD-201 | 4'-Bromo | H | 5 | 9 ± 2 |
| ABD-261 | 4'-Acetyl | H | 5 | 11 ± 2 |
| ABD-262 | 4'-Cyano | H | 5 | 12 ± 2 |
| ABD-260 | 4'-Methyl | H | 5 | 12 ± 2 |
| ABD-257 | 3',4'-Difluoro | H | 5 | 16 ± 3 |
| ABD-155 | H | H | 4 | 18 ± 3 |
| ABD-180 | H | H | 5 | 20 ± 3 |
| ABD-277 | 4'-Hydroxy | H | 5 | 21 ± 3 |
| ABD-263 | 2'-Amino | H | 4 | 24 ± 3 |
| ABD-308 | 3'-Methyl | H | 4 | 28 ± 3 |
| ABD-267 | 2'-Methoxy | H | 5 | 31 ± 4 |
| ABD-276 | 4'-Dimethylamino | H | 5 | 32 ± 3 |
| ABD-226 | 3'-Nitro | H | 4 | 33 ± 3 |
| ABD-271 | 4'-Carboxy | H | 5 | 33 ± 3 |
| ABD-279 | 4'-Phenyl | H | 5 | 33 ± 5 |
| ABD-297 | 4'-Ethoxy | H | 5 | 35 ± 5 |
| ABD-258 | 4'-Methylthio | H | 4 | 35 ± 6 |

Of the compounds tested, the most potent are those that have electron-withdrawing groups at the 2 and 4 positions of Ring A. In many cases, these groups are also hydrophobic. However, in one particularly potent compound, the substituent is a nitro group. The data also show that additional increases in potency are possible by the presence of alkyl, haloalkyl, and/or haloalkoxy substituents on Ring B.

FIG. 1 is a graph of J774 macrophage viability ("J774") (solid diamonds, ♦) as measured by the Alamar Blue macrophage J774 viability assay; and osteoblast survival ("OB") (open squares, □) as measured by the Alamar Blue mouse osteoblast assay; expressed as percent (%) of control, after 72 hours exposure to biphenyl-4-sulfonic acid-(4-hydroxybutyl)-amide (ABD-155) as a function of compound concentration.

FIG. 1 shows that ABD-155 is highly potent against J774 macrophages ($IC_{50}$<20 μM) but shows little activity against osteoblasts ($IC_{50}$>100 μM). This demonstrates that ABD-155 has the potential to be an effective drug for the treatment of diseases involving excess bone loss, such as osteoporosis; and the treatment of diseases with an inflammatory or autoimmune component, such as rheumatoid arthritis.

Figure 2:
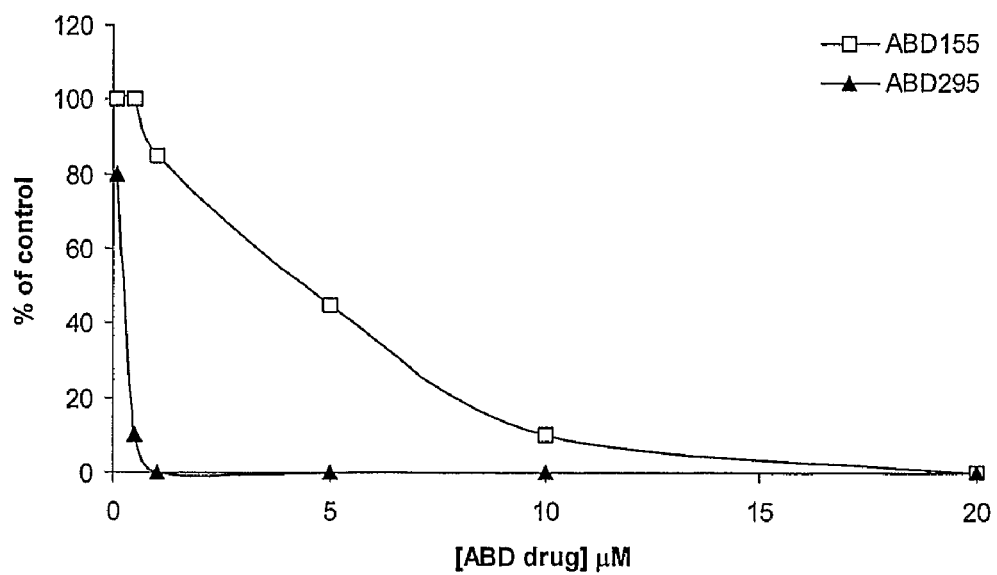
FIG. 2 is a graph of osteoclast number as measured by TRAcP staining, as a function of drug concentration, and shows the effects of ABD-155 and ABD-295 on osteoclast formation in the murine co-culture system; expressed as percent (%) of control, after 72 hours exposure to biphenyl-4-sulfonic acid-(4-hydroxybutyl)-amide (ABD-155) (open squares, □) or 2',4'-difluoro, 3-methyl biphenyl-4-sulfonic acid-(4-hydroxybutyl)-amide (ABD-295) (solid triangles, ▲).

FIG. 2 is a graph of osteoclast number as measured by TRAcP staining, as a function of drug concentration, and shows the effects of ABD-155 and ABD-295 on osteoclast formation in the murine co-culture system; expressed as percent (%) of control, after 72 hours exposure to biphenyl-4-sulfonic acid-(4-hydroxybutyl)-amide (ABD-155) (open squares, □) or 2',4'-difluoro, 3-methyl biphenyl-4-sulfonic acid-(4-hydroxybutyl)-amide (ABD-295) (solid triangles, ▲).

FIG. 2 shows that ABD-295 is highly potent against osteoclast precursors (IC$_{50}$ 200 nM) and that the increase in potency over the parent compound (ABD-155) shown in the J774 macrophage studies is also translated into higher potency against osteoclasts. This demonstrates that ABD-295 has the potential to be an effective drug for the treatment of diseases involving excess bone loss, such as osteoporosis.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The present invention is not limited to those embodiments which are encompassed by the appended claims, which claims pertain to only some of many preferred groups of embodiments, and which claims are included at this time primarily for initial search purposes.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Armour, K. J., et al., 2001, "Inhibition of bone resorption in vitro and prevention of ovariectomy-induced bone loss in vivo by flurbiprofen nitroxybutylester (HCT1026)," *Arthritis Rheum.*, Vol. 44, No. 9, pp. 2185-2192.

Augstein, J., Austin, W. C., Boscott, R. J., Green, S. M., Worthing, C. R., 1965, "Some Cardiovascular Effects of a Series of Aryloxyalkylamines 1," *J. Med. Chem.*, Vol. 8, pp. 356-367.

Coxon, F. P., Helfrich, M. H., Van't H of, R., Sebti, S., Ralston, S. H., Hamilton, A., and Rogers, M. J., 2000, "Protein geranylgeranylation is required for osteoclast formation, function, and survival: inhibition by bisphosphonates and GGTI-298," *J.Bone Miner.Res.*, Vol. 15, pp. 1467-1476.

Degenhardt and Burdsall, 1986, "Synthesis of Ethenylidenebis (phosphonic acid) and its Tetraalkyl Esters," *J. Org. Chem.*, Vol. 51, pp. 3488-3490.

Eberhard and Westheimer, 1965, "Hydrolysis of Phostonates," *J. Amer. Chem. Soc.*, Vol. 87, pp. 252-260.

Ha-Duong N-T., Dijols S., Marques-Soares C., Minoletti C., Dansette P M. and Masuy D., 2001, "Synthesis of Sulfaphenazole Derivatives and Their Use as Inhibitors and Tools for Comparing the Active Sites of Human Liver Cytochromes P450 of the 2C Subfamily," *J. Med. Chem.*, Vol. 44, pp. 3622-3631.

Herczegh et al, 2002, "Osteoadsorptive Bisphosphonate Derivatives of Fluoroquinolone Antibacterials," *J. Med. Chem., Vol.* 45, pp. 2338-2341.

Hughes, D. E., Boyce, B. F., 1997, "Apoptosis in bone physiology and disease," Molecular *Pathology*, Vol. 50, pp. 132-137.

Kong, Y. Y., Yoshida, H., Sarosi, I., Tan, H. L., Timms, E., Capparelli, C., et al, 1999, "OPGL is a key regulator of osteoclastogenesis, lymphocyte development and lymph-node organogenesis," *Nature*, Vol. 397, pp. 315-323.

Luckman, S. P., Coxon, F. P., Ebetino, F. H., Russell, R. G., and Rogers, M. J., 1998, "Heterocycle-containing bisphosphonates cause apoptosis and inhibit bone resorption by preventing protein prenylation: evidence from structure-activity relationships in J774 macrophages," *J. Bone Miner.Res.*, Vol. 13, pp. 1668-1678.

MacPherson, H; Noble, B. S.; Ralston, S. H., 1999, "Expression and functional role of nitric oxide synthase isoforms in human osteoblast-like cells," *Bone*, Vol. 24, pp. 179-185.

Mundy, G. R., 1996, *Bone Remodelling and its disorders* (2nd edition), London: Martin Dunitz.

Nociari, M. N., et al., 1998, "A Novel one-step, highly sensitive fluorimetric assay to evaluate cell-mediated cytotoxicity," *Journal of Immunological Methods*, Vol. 213, pp. 157-167.

Raisz, L. G., 1988, "Local and systemic factors in the pathogenesis of osteoporosis," *N. Engl. J. Med.*, Vol. 318, pp. 818-828.

Ralston, S. H., 1997, "Science, Medicine and the Future: Osteoporosis," *Br. Med. J., Vol.* 315, pp. 469-472.

Ralston, S. H., et al., 2003, "Alkane Diol Derivatives as Therapeutic Agents for the Treatment of Bone Conditions," published international (PCT) patent application publication no. WO 03/037321, (PCT/GB02/04933) published 8 May 2003.

Ralston, S. H., et al., 2003, "Ketones and Reduced Ketones as Therapeutic Agents for the Treatment of Bone Conditions," published international (PCT) patent application publication no. WO 2004/098582 A2, (PCT/GB02004/001958) published 18 Nov. 2004.

Rodan, G. A., Harada, S., 1997, "The missing bone," *Cell*, Vol. 89, pp. 677-680.

Takahashi, N.; Akatsu, T.; Udagawa, N.; Sasaki, T.; Yamaguchi, A.; Moseley, J. M.; Martin, T. J.; Suda, T., 1988, "Osteoblastic cells are involved in osteoclast formation," *Endocrinology*, Vol. 123, pp. 2600-2602, 1988.

Takasuka, M., Yamakawa, M., Ohtani, M., 1991, "FTIR Spectral Study of Intramolecular Hydrogen Bonding in Thromboxane A$_2$ Receptor Antagonist S-145 and Related Compounds. 3. Conformation and Activity of S-145 Analogues," *J. Med. Chem.*, Vol. 34, pp. 1885-1891.

van't H of, R. J., and Ralston, S. H., 1997, "Cytokine-induced nitric oxide inhibits bone resorption by inducing apoptosis of osteoclast progenitors and suppressing osteoclast activity," *J. Bone Miner. Res.*, Vol. 12, pp. 1797-804.

Yasuda, H., Shima, N., Nakagawa, N., Mochizuki, S. I., Yano, K., Fujise, N., et al, 1998, "Identity of osteoclastogenesis inhibitory factor (OCIF) and osteoprotegerin (OPG): a mechanism by which OPG/OCIF inhibits osteoclastogenesis in vitro," *Endocrinology*, Vol. 139, pp. 1329-1337.

The invention claimed is:

1. A compound selected from compounds of the following formula and pharmaceutically acceptable salts thereof:

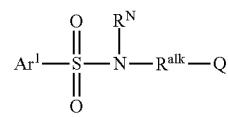

wherein Ar$^1$ is independently:

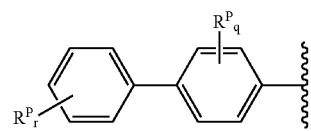

r is independently an integer from 0 to 3;
q is independently an integer from 0 to 2; and each $R^P$ is independently: —C(=O)OH, —C(=O)OMe, —C(=O)OEt, —C(=O)O(iPr), —C(=O)O(tBu), —C(=O)O(cPr), —C(=O)OCH$_2$CH$_2$OH, —C(=O)OCH$_2$CH$_2$OMe, —C(=O)OCH$_2$CH$_2$OEt, —C(=O)OPh, —C(=O)OCH$_2$Ph, —(C=O)NH$_2$, —(C=O)NMe$_2$, —(C=O)NEt$_2$, —(C=O)N(iPr)$_2$, —(C=O)N(CH$_2$CH$_2$OH)$_2$, —(C=O)-morpholino, —(C=O)NHPh, —(C=O)NHCH$_2$Ph, —(C=O)Me, —(C=O)Et, —(C=O)(tBu), —(C=O)-cHex, —(C=O)Ph, —(C=O)CH$_2$Ph, —F, —Cl, —Br, —I, —CN, —NO$_2$, —OH, —OMe, —OEt, —O(iPr), —O(tBu), —OPh, —OCH$_2$Ph, —OCF$_3$, —OCH$_2$CF$_3$, —OCH$_2$CH$_2$OH, —OCH$_2$CH$_2$OMe, —OCH$_2$CH$_2$OEt, —OCH$_2$CH$_2$NH$_2$, —OCH$_2$CH$_2$NMe$_2$, —OCH$_2$CH$_2$N(iPr)$_2$, —OPh-Me, —OPh-OH, —OPh-OMe, —OPh-F, —OPh-Cl, —OPh-Br, —OPh-I, —SH, —SMe, —SEt, —SPh, —SCH$_2$Ph, —OC(=O)Me, —OC(=O)Et, —OC(=O)(iPr), —OC(=O)(tBu), —OC(=O)(cPr), —OC(=O)CH$_2$CH$_2$OH, —OC(=O)CH$_2$CH$_2$OMe, —OC(=O)CH$_2$CH$_2$OEt, —OC(=O)Ph, —OC(=O)CH$_2$Ph, —NH$_2$, —NHMe, —NHEt, —NH(iPr), —NMe$_2$, —NEt$_2$, —N(iPr)$_2$, —N(CH$_2$CH$_2$OH)$_2$, —NHPh, —NHCH$_2$Ph, piperidino, piperazino, morpholino, —NH(C=O)Me, —NH(C=O)Et, —NH(C=O)Ph, —NHC(=O)CH$_2$Ph, —NMe(C=O)Me, —NMe(C=O)Et, —NMe(C=O)Ph, —NMeC(=O)CH$_2$Ph, —NH(C=O)NH$_2$, —NH(C=O)NHMe, —NH(C=O)NHEt, —NH(C=O)NPh, —NH(C=O)NHCH$_2$Ph, —NH(C=S)NH$_2$, —NH(C=S)NHMe, —NH(C=S)NHEt, —NH(C=S)NPh, —NH(C=S)NHCH$_2$Ph, —NHSO$_2$Me, —NHSO$_2$Et, —NHSO$_2$Ph, —NHSO$_2$PhMe, —NHSO$_2$CH$_2$Ph, —NMeSO$_2$Me, —NMeSO$_2$Et, —NMeSO$_2$Ph, —NMeSO$_2$PhMe, —NMeSO$_2$CH$_2$Ph, —SO$_2$Me, —SO$_2$CF$_3$, —SO$_2$Et, —SO$_2$Ph, —SO$_2$PhMe, —SO$_2$CH$_2$Ph, —OSO$_2$Me, —OSO$_2$CF$_3$, —OSO$_2$Et, —OSO$_2$Ph, —OSO$_2$PhMe, —OSO$_2$CH$_2$Ph, —SO$_2$NH$_2$, —SO$_2$NHMe, —SO$_2$NHEt, —SO$_2$NMe$_2$, —SO$_2$NEt$_2$, —SO$_2$-morpholino, —SO$_2$NHPh, —SO$_2$NHCH$_2$Ph, —CH$_2$Ph, —CH$_2$Ph-Me, —CH$_2$Ph-OH, —CH$_2$Ph-F, —CH$_2$Ph-Cl, -Ph, -Ph-Me, -Ph-OH, -Ph-OMe, -Ph-F, -Ph-Cl, -Ph-Br, -Ph-I, pyridyl, pyrazinyl, pyrimidinyl, pyridazinyl, furanyl, thiophenyl, pyrrolyl, imidazolyl, pyrazolyl, oxazolyl, thiazolyl, pyrrolidinyl, piperidinyl, azepinyl, tetrahydropyranyl, morpholinyl, azetidinyl, piperazinyl, imidazolinyl, piperazinedionyl, and oxazolinonyl, -Me, -Et, -nPr, -iPr, -nBu, -iBu, -sBu, -tBu, -nPe, -cPr, -cHex, —CH=CH$_2$, —CH$_2$—CH=CH$_2$, —CF$_3$, —CHF$_2$, —CH$_2$F, —CCl$_3$, —CBr$_3$, —CH$_2$CH$_2$F, —CH$_2$CHF$_2$, and —CH$_2$CF$_3$, —CH$_2$OH, —CH$_2$OMe, —CH$_2$OEt, —CH$_2$NH$_2$, —CH$_2$NMe$_2$, —CH$_2$CH$_2$OH, —CH$_2$CH$_2$OMe, —CH$_2$CH$_2$OEt, —CH$_2$CH$_2$CH$_2$NH$_2$, and —CH$_2$CH$_2$NMe$_2$;

and wherein $R^N$ is independently —H or C$_{1-7}$alkyl;

and wherein $R^{alk}$ is a fully saturated aliphatic C$_{4-10}$alkylene group;

and wherein Q is independently —OH, —O—$R^{E1}$, or —O—C(=O)—$R^{E2}$;

wherein:

$R^{E1}$ is independently C$_{1-7}$alkyl; and $R^{E2}$ is independently C$_{1-7}$alkyl.

2. A compound according to claim 1, wherein Q is independently —OH.

3. A compound according to claim 2, wherein $R^{alk}$ is —(CH$_2$)$_n$— where n is an integer from 4 to 7.

4. A compound according to claim 2, wherein $R^{alk}$ is —(CH$_2$)$_n$— where n is 4 or 5.

5. A compound according to claim 2, wherein $R^N$ is independently —H or -Me.

6. A compound according to claim 3, wherein $R^N$ is independently —H or -Me.

7. A compound according to claim 4, wherein $R^N$ is independently —H or -Me.

8. A compound according to claim 2, wherein $R^N$ is independently —H.

9. A compound according to claim 3, wherein $R^N$ is independently —H.

10. A compound according to claim 4, wherein $R^N$ is independently —H.

11. A compound according to claim 2, wherein each $R^P$ is independently: —C(=O)OH, —C(=O)OMe, —C(=O)OEt, —C(=O)O(tBu), —C(=O)OPh, —C(=O)NH$_2$, —C(=O)NHMe, —C(=O)NMe$_2$, —C(=O)NHPh, —C(=O)Me, —F, —Cl, —Br, —I, —CN, —NO$_2$, —OH, —OMe, —OEt, —O(iPr), —O(nPr), —O(tBu), —OPh, —OBn, —OCF$_3$, —SMe, —OC(C=O)Me, —OC(C=O)Et, —OC(C=O)(tBu), —OC(C=O)Ph, —NH$_2$, —NHMe, —NMe$_2$, —NHEt, —NEt$_2$, —NHC(=O)Me, —NHC(=O)Et, —NHC(=O)Ph, —S(=O)$_2$Me, —S(=O)$_2$Et, —S(=O)$_2$Ph, —SO$_2$NH$_2$, -Ph, -Me, -Et, -iPr, -nPr, -cPr, -tBu, or —CF$_3$.

12. A compound according to claim 4, wherein each $R^P$ is independently: —C(=O)OH, —C(=O)OMe, —C(=O)OEt, —C(=O)O(tBu), —C(=O)OPh, —C(=O)NH$_2$, —C(=O)NHMe, —C(=O)NMe$_2$, —C(=O)NHPh, —C(=O)Me, —F, —Cl, —Br, —I, —CN, —NO$_2$, —OH, —OMe, —OEt, —O(iPr), —O(nPr), —O(tBu), —OPh, —OBn, —OCF$_3$, —SMe, —OC(C=O)Me, —OC(C=O)Et, —OC(C=O)(tBu), —OC(C=O)Ph, —NH$_2$, —NHMe, —NMe$_2$, —NHEt, —NEt$_2$, —NHC(=O)Me, —NHC(=O)Et, —NHC(=O)Ph, —S(=O)$_2$Me, —S(=O)$_2$Et, —S(=O)$_2$Ph, —SO$_2$NH$_2$, -Ph, -Me, -Et, -iPr, -nPr, -cPr, -tBu, or —CF$_3$.

13. A compound according to claim 8, wherein each $R^P$ is independently: —C(=O)OH, —C(=O)OMe, —C(=O)OEt, —C(=O)O(tBu), —C(=O)OPh, —C(=O)NH$_2$, —C(=O)NHMe, —C(=O)NMe$_2$, —C(=O)NHPh, —C(=O)Me, —F, —Cl, —Br, —I, —CN, —NO$_2$, —OH, —OMe, —OEt, —O(iPr), —O(nPr), —O(tBu), —OPh, —OBn, —OCF$_3$, —SMe, —OC(C=O)Me, —OC(C=O)Et, —OC(C=O)(tBu), —OC(C=O)Ph, —NH$_2$, —NHMe, —NMe$_2$, —NHEt, —NEt$_2$, —NHC(=O)Me, —NHC(=O)Et, —NHC(=O)Ph, —S(=O)$_2$Me, —S(=O)$_2$Et, —S(=O)$_2$Ph, —SO$_2$NH$_2$, -Ph, -Me, -Et, -iPr, -nPr, -cPr, -tBu, or —CF$_3$.

14. A compound according to claim 10, wherein each $R^P$ is independently: —C(=O)OH, —C(=O)OMe, —C(=O)OEt, —C(=O)O(tBu), —C(=O)OPh, —C(=O)NH$_2$, —C(=O)NHMe, —C(=O)NMe$_2$, —C(=O)NHPh, —C(=O)Me, —F, —Cl, —Br, —I, —CN, —NO$_2$, —OH, —OMe, —OEt, —O(iPr), —O(nPr), —O(tBu), —OPh, —OBn, —OCF$_3$, —SMe, —OC(C=O)Me, —OC(C=O)Et, —OC(C=O)(tBu), —OC(C=O)Ph, —NH$_2$, —NHMe, —NMe$_2$, —NHEt, —NEt$_2$, —NHC(=O)Me, —NHC(=O)Et, —NHC(=O)Ph, —S(=O)$_2$Me, —S(=O)$_2$Et, —S(=O)$_2$Ph, —SO$_2$NH$_2$, -Ph, -Me, -Et, -iPr, -nPr, -cPr, -tBu, or —CF$_3$.

15. A compound according to claim 2, wherein each $R^P$ is independently: -Me, -Et, —F, —Cl, —Br, —OH, —OMe, —OEt, —NH$_2$, —NHMe, —NMe$_2$, —NHEt, —NEt$_2$, —NO$_2$, —CN, —CF$_3$, —OCF$_3$, —C(=O)Me, —C(=O)OH, —C(=O)OMe, —C(=O)OEt, —C(=O)O(tBu), or —SMe.

16. A compound according to claim 4, wherein each $R^P$ is independently: -Me, -Et, —F, —Cl, —Br, —OH, —OMe, —OEt, —NH$_2$, —NHMe, —NMe$_2$, —NHEt, —NEt$_2$, —NO$_2$, —CN, —CF$_3$, —OCF$_3$, —C(=O)Me, —C(=O)OH, —C(=O)OMe, —C(=O)OEt, —C(=O)O(tBu), or —SMe.

17. A compound according to claim 8, wherein each $R^P$ is independently: -Me, -Et, —F, —Cl, —Br, —OH, —OMe, —OEt, —NH$_2$, —NHMe, —NMe$_2$, —NHEt, —NEt$_2$, —NO$_2$, —CN, —CF$_3$, —OCF$_3$, —C(=O)Me, —C(=O)OH, —C(=O)OMe, —C(=O)OEt, —C(=O)O(tBu), or —SMe.

18. A compound according to claim 10, wherein each $R^P$ is independently: -Me, -Et, —F, —Cl, —Br, —OH, —OMe, —OEt, —NH$_2$, —NHMe, —NMe$_2$, —NHEt, —NEt$_2$, —NO$_2$, —CN, —CF$_3$, —OCF$_3$, —C(=O)Me, —C(=O)OH, —C(=O)OMe, —C(=O)OEt, —C(=O)O(tBu), or —SMe.

19. A compound according to claim 2, wherein each $R^P$ is independently selected from: -Me, -Et, —F, —Cl, —Br, —OMe, —OEt, —CN, —CF$_3$, and —OCF$_3$.

20. A compound according to claim 4, wherein each $R^P$ is independently selected from: -Me, -Et, —F, —Cl, —Br, —OMe, —OEt, —CN, —CF$_3$, and —OCF$_3$.

21. A compound according to claim 8, wherein each $R^P$ is independently selected from: -Me, -Et, —F, —Cl, —Br, —OMe, —OEt, —CN, —CF$_3$, and —OCF$_3$.

22. A compound according to claim 10, wherein each $R^P$ is independently selected from: -Me, -Et, —F, —Cl, —Br, —OMe, —OEt, —CN, —CF$_3$, and —OCF$_3$.

23. A compound according to claim 2, wherein $Ar^1$ is independently:

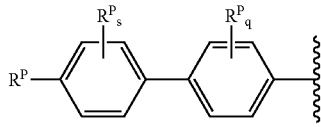

wherein:
q is independently 0 or 1; and
s is independently 0 or 1.

24. A compound according to claim 10, wherein $Ar^1$ is independently:

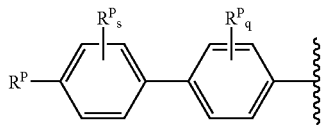

wherein:
q is independently 0 or 1; and
s is independently 0 or 1.

25. A compound according to claim 2, wherein $Ar^1$ is independently:

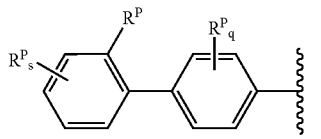

wherein:
q is independently 0 or 1; and
s is independently 0 or 1.

26. A compound according to claim 10, wherein $Ar^1$ is independently:

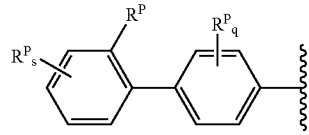

wherein:
q is independently 0 or 1; and
s is independently 0 or 1.

27. A compound according to claim 2, wherein $Ar^1$ is independently:

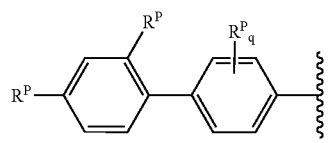

wherein:
q is independently 0 or 1.

28. A compound according to claim 10, wherein $Ar^1$ is independently:

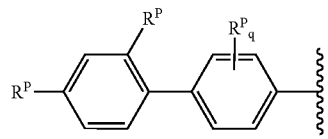

wherein:
q is independently 0 or 1.

29. A compound selected from the following compounds, and pharmaceutically acceptable salts thereof:

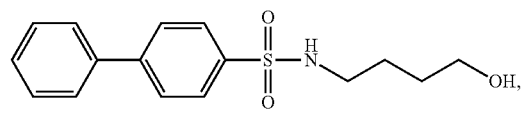

ABD-155

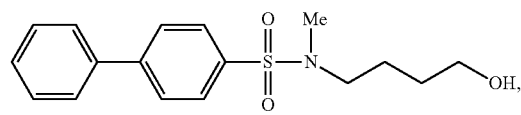

ABD-156

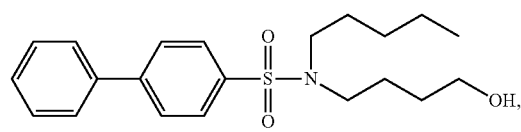

ABD-164

ABD-180
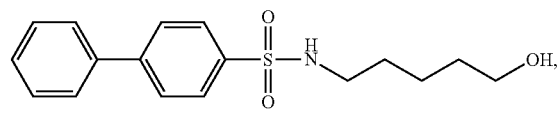
ABD-185
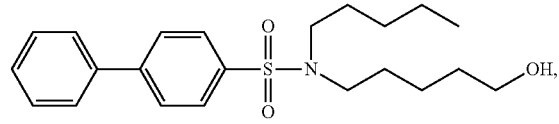
ABD-186
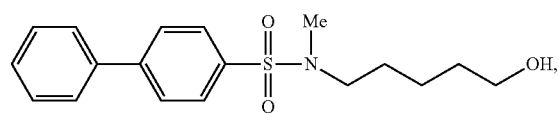
ABD-180
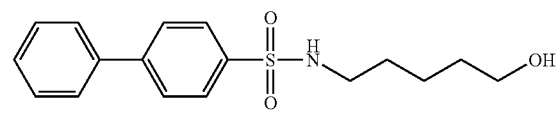
ABD-185
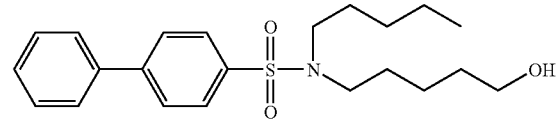
ABD-186
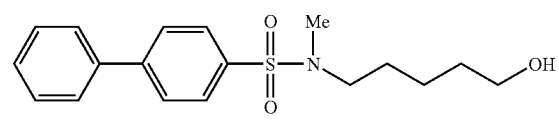
ABD-199
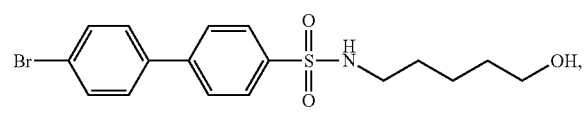
ABD-200
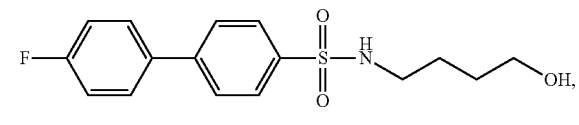
ABD-201
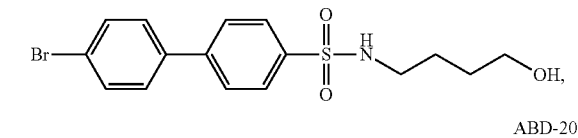
ABD-203
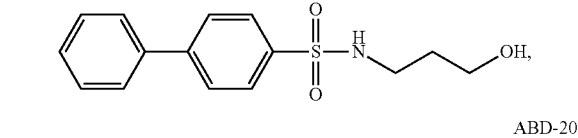
ABD-205
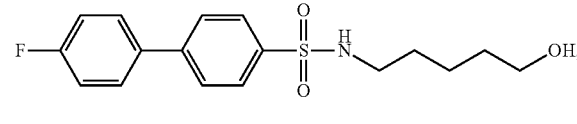
ABD-226
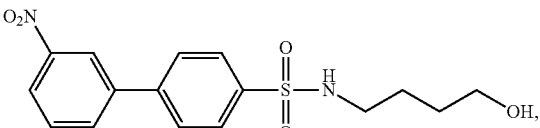
ABD-227
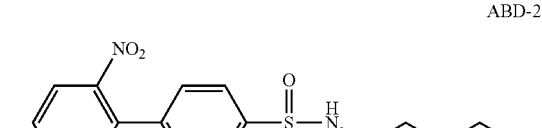
ABD-234
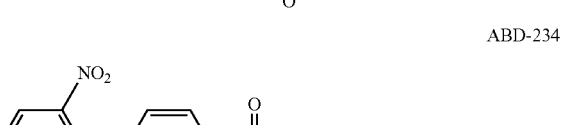
ABD-246
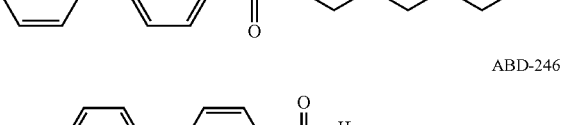
ABD-248
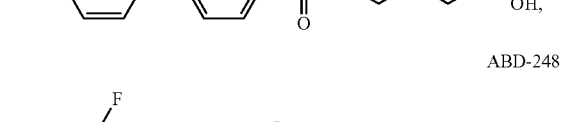
ABD-256
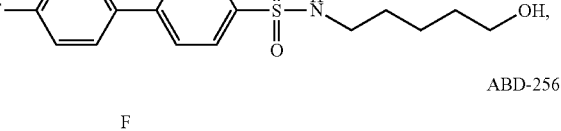
ABD-257
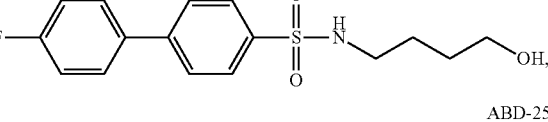
ABD-258
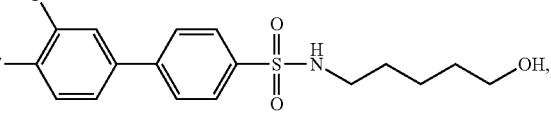
ABD-259
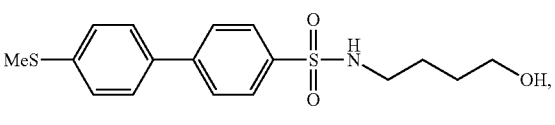
ABD-260
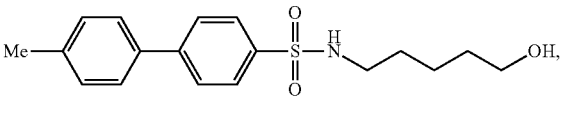

-continued

ABD-261: Me-C(O)-C6H4-C6H4-S(O)2-NH-(CH2)5-OH,

ABD-262: NC-C6H4-C6H4-S(O)2-NH-(CH2)5-OH,

ABD-263: 2-NH2-C6H4-C6H4-S(O)2-NH-(CH2)4-OH,

ABD-265: 4-Br-2-F-C6H3-C6H4-S(O)2-NH-(CH2)4-OH,

ABD-267: 2-OMe-C6H4-C6H4-S(O)2-NH-(CH2)5-OH,

ABD-269: 2-F-C6H4-C6H4-S(O)2-NH-(CH2)4-OH,

ABD-271: HOOC-C6H4-C6H4-S(O)2-NH-(CH2)5-OH,

ABD-275: 2-I-C6H4-C6H4-S(O)2-NH-(CH2)4-OH,

ABD-276: Me2N-C6H4-C6H4-S(O)2-NH-(CH2)5-OH,

ABD-277: HO-C6H4-C6H4-S(O)2-NH-(CH2)5-OH,

-continued

ABD-278: 2,4-Cl2-C6H3-C6H4-S(O)2-NH-(CH2)5-OH,

ABD-279: Ph-C6H4-C6H4-S(O)2-NH-(CH2)5-OH,

ABD-282: 2-(4-F-C6H4)-C6H4-S(O)2-NH-(CH2)4-OH,

ABD-284: 2-CF3-C6H4-C6H4-S(O)2-NH-(CH2)5-OH,

ABD-289: C6F5-C6H4-S(O)2-NH-(CH2)5-OH,

ABD-294: 4'-CF3-2-F-C6H3-C6H4-S(O)2-NH-(CH2)4-OH,

ABD-295: 2-Me-2',4'-F2-C6H3-C6H3-S(O)2-NH-(CH2)4-OH,

ABD-297: EtO-C6H4-C6H4-S(O)2-NH-(CH2)5-OH,

ABD-302: 4'-CF3-3-F-C6H3-C6H3-S(O)2-NH-(CH2)4-OH,

-continued

ABD-306
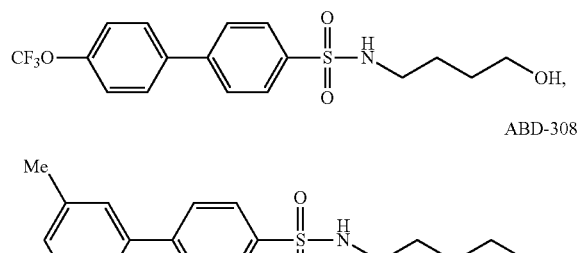

ABD-308
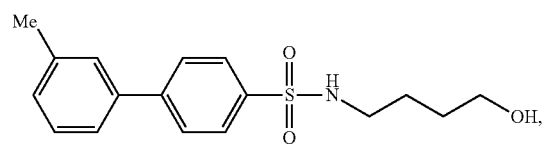

ABD-310
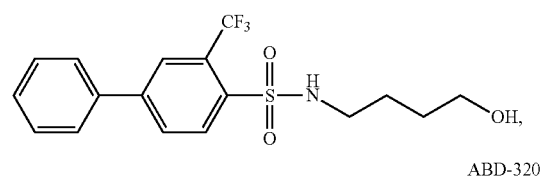

ABD-320
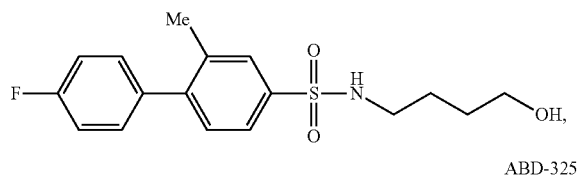

ABD-325
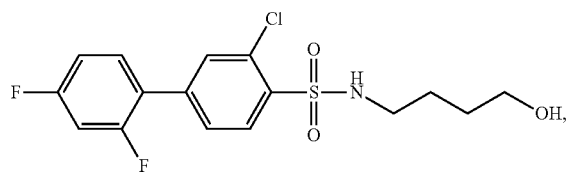

ABD-360
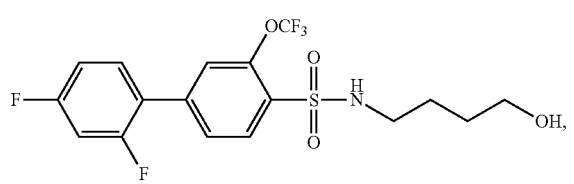

and

-continued

ABD-365
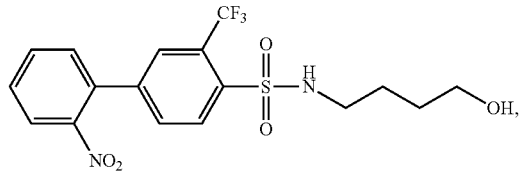

30. A compound selected from the following compound and pharmaceutically acceptable salts thereof:

(ABD-295)
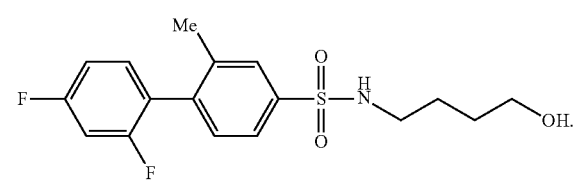

31. A composition comprising a compound according to claim 1 and a pharmaceutically acceptable carrier or diluent.

32. A compound according to claim 1, which is selected from the following compounds, and pharmaceutically acceptable salts thereof:

(ABD-192)
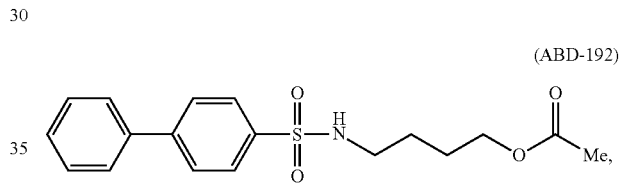

and (ABD-266)
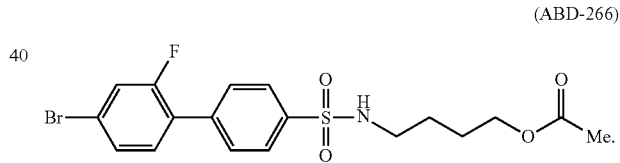

* * * * *